US012630645B2

(12) United States Patent
Herbel et al.

(10) Patent No.: US 12,630,645 B2
(45) Date of Patent: May 19, 2026

(54) COMPOSITIONS AND METHODS FOR TREATING CANCER EXPRESSING CD90 AND CD326

(71) Applicant: Miltenyi Biotec B.V. & Co. KG, Bergisch Gladbach (DE)

(72) Inventors: Christoph Herbel, Bergisch Gladbach (DE); Dominik Eckardt, Bergisch Gladbach (DE); Vera Dittmer, Bergisch Gladbach (DE); Manuel Martinez-Osuna, Bergisch Gladbach (DE); Jutta Kollet, Bergisch Gladbach (DE); Thorsten Olaf Hardt, Bergisch Gladbach (DE); Andreas Bosio, Bergisch Gladbach (DE)

(73) Assignee: Miltenyi Biotec B.V. & Co. KG, Bergisch Gladbach (DE)

( * ) Notice: Subject to any disclaimer, the term of this patent is extended or adjusted under 35 U.S.C. 154(b) by 698 days.

(21) Appl. No.: 17/925,883

(22) PCT Filed: May 19, 2021

(86) PCT No.: PCT/EP2021/063306
§ 371 (c)(1),
(2) Date: Nov. 17, 2022

(87) PCT Pub. No.: WO2021/234006
PCT Pub. Date: Nov. 25, 2021

(65) Prior Publication Data
US 2023/0183372 A1     Jun. 15, 2023

(30) Foreign Application Priority Data
May 20, 2020    (EP) ..................................... 20175589

(51) Int. Cl.
| | |
|---|---|
| *C07K 16/30* | (2006.01) |
| *A61K 40/11* | (2025.01) |
| *A61K 40/31* | (2025.01) |
| *A61K 40/42* | (2025.01) |
| *C07K 14/725* | (2006.01) |
| *C07K 16/28* | (2006.01) |

(52) U.S. Cl.
CPC .............. *C07K 16/30* (2013.01); *A61K 40/11* (2025.01); *A61K 40/31* (2025.01); *A61K 40/421* (2025.01); *A61K 40/4254* (2025.01); *C07K 14/7051* (2013.01); *C07K 16/2803* (2013.01); *A61K 2239/29* (2023.05); *A61K 2239/59* (2023.05); *C07K 2319/02* (2013.01); *C07K 2319/03* (2013.01); *C07K 2319/20* (2013.01)

(58) Field of Classification Search
None
See application file for complete search history.

(56) References Cited

U.S. PATENT DOCUMENTS

| | | | |
|---|---|---|---|
| 9,233,125 B2 | 1/2016 | Davila et al. | |
| 11,173,179 B2 * | 11/2021 | Ma .......................... | A61P 35/02 |
| 2015/0132217 A1 | 5/2015 | Chang et al. | |
| 2019/0330300 A1 | 10/2019 | Scholler et al. | |
| 2023/0183351 A1 * | 6/2023 | Ehninger ........... | C07K 16/2803 |
| | | | 424/134.1 |

FOREIGN PATENT DOCUMENTS

| | | |
|---|---|---|
| CN | 105246504 A | 1/2016 |
| CN | 105505869 A | 4/2016 |
| WO | WO 2014/127261 | 8/2014 |
| WO | WO 2017/091546 | 6/2017 |

OTHER PUBLICATIONS

Yamashita, et al. (2013) "Discrete Nature of EpCAM+ and CD90+ Cancer Stem Cells in Human Heptaocellular Carcinoma", Heptaology, 57(4): 1484-97. (Year: 2013).*
Feldmann, et al. (2017) Retargeting of T lymphocytes to PSCA- or PSMA positive prostate cancer cells using the novel modular chimeric antigen receptor platform technology 'UniCAR', Oncotarget, 8(19) 31368-85. (Year: 2017).*
Connor et al., "Thy-1 predicts poor prognosis and is associated with self-renewal in ovarian cancer," Journal of Ovarian Research, Dec. 2019, 12(1), 11 pages.
Lamers et al., "Treatment of metastatic renal cell carcinoma with CAIX CAR-engineered T cells: clinical evaluation and management of on-target toxicity," Molecular Therapy, Apr. 1, 2013, 21(4):904, 20 pages.
Lanitis et al., "Chimeric Antigen Receptor T Cells with Dissociated Signaling Domains Exhibit Focused Antitumor Activity with Reduced Potential for Toxicity In Vivo Trans-Signaling CAR-T Cells for Focused Tumor Targeting," Cancer Immunology Research, Jul. 1, 2013, 1(1):43-53.
Matulonis et al., "Ovarian Cancer," Nature Reviews Disease Primers, Aug. 25, 2016, 2(1), 48 pages.
PCT International Preliminary Report on Patentability in International Appln. No. PCT/EP2021/063306, dated Dec. 1, 2022, 9 pages.

(Continued)

*Primary Examiner* — Robert M Kelly
(74) *Attorney, Agent, or Firm* — Fish & Richardson P.C.

(57) ABSTRACT

The present invention provides a combination comprising a) an antigen binding domain specific for CD90, and b) an antigen binding domain specific for CD326, for use in treatment of human cancer comprising cancerous cells that co-express CD90 and CD326. In one embodiment of the invention the combination comprises a) an immune cell comprising a CAR comprising an antigen binding domain specific for a tag of a first and a second polypeptide, b) said tagged first polypeptide that has an antigen binding domain specific for CD90, and c) said tagged second polypeptide that has an antigen binding domain specific for CD326, wherein the tag of the first polypeptide and the tag of the second polypeptide are identical. In a further embodiment the concentrations used for said first and that second polypeptide are below the activation threshold of said CAR, respectively, but the sum of both concentrations is above the activation threshold of said CAR.

15 Claims, 55 Drawing Sheets

Specification includes a Sequence Listing.

(56)         References Cited

OTHER PUBLICATIONS

PCT International Search Report and Written Opinion in International Appln. No. PCT/EP2021/063306, dated Aug. 3, 2021, 13 pages.

Zhao et al., "Clinical trials of dual-target CAR T cells, donor-derived CAR T cells, and universal CAR T cells for acute lymphoid leukemia," Journal of Hematology & Oncology, Dec. 2019, 12(1):1-1.

Chames, "Bispecific antibodies for cancer therapy: the light at the end of the tunnel?," Mabs, Nov. 2009, 1(6):539-47.

Liu et al., "Biological features of CD90+ tumor stem cells in ovarian cancer," Chinese Journal of Tissue Engineering Research, Mar. 2016, 20(10):1468, 1 page (English abstract only).

Shufang et al., "The Expression of CD90 and EpCAM in Human Hepatocellular Carcinoma Cell Lines and Characteristics Analysis of EpCAM~+ Cells," Chinese Journal of Cell Biology, Jan. 2015, 37(1):47, 1 page (English abstract only).

You et al., "Advances in the treatment of prostate cancer by chimeric antigen receptor modified T cells," Tianjin Medical Journal, Oct. 15, 2020, 48(10), 5 pages (with English abstract).

* cited by examiner

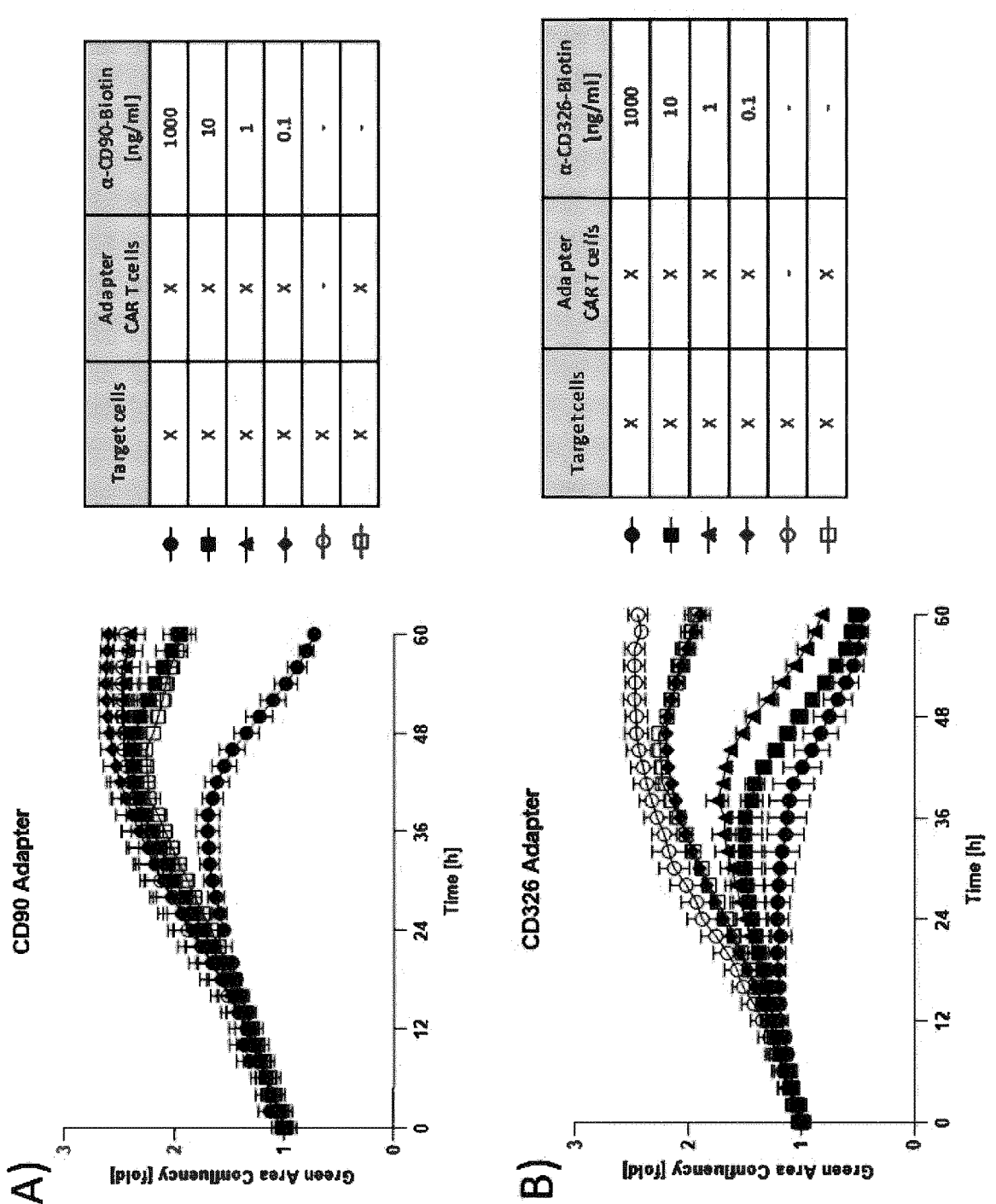
Figure 4 A, B

| Target cells | Adapter CAR T cells | Adapter |
|---|---|---|
| x | - | α-CD90-Biotin, 1000 ng/ml |
| x | - | α-CD326-Biotin, 1000 ng/ml |
| x | - | α-CD19-Biotin, 1000 ng/ml |
| x | x | α-CD19-Biotin, 1000 ng/ml |
| x | - | - |
| x | x | - |

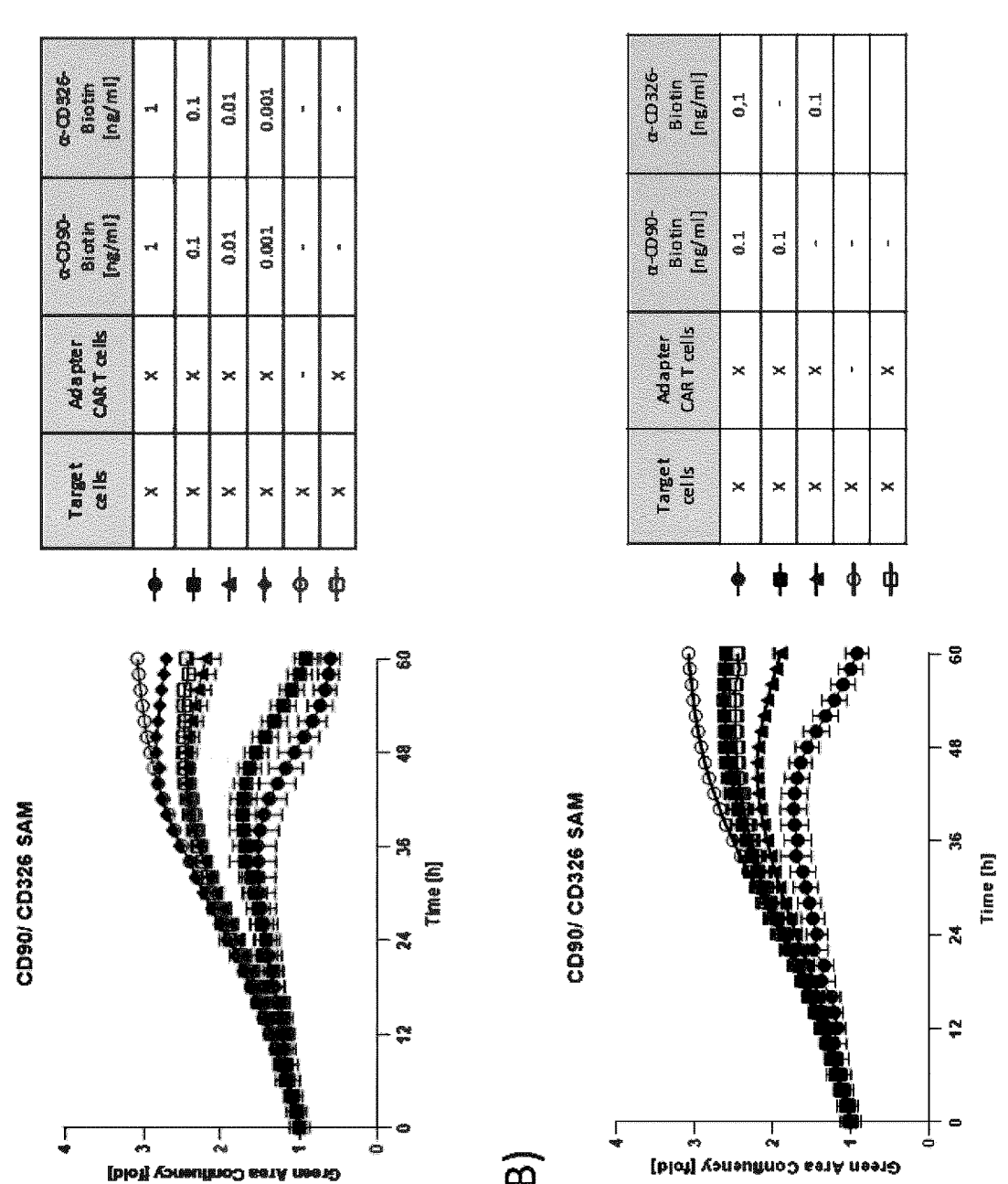
Figure 5 A, B

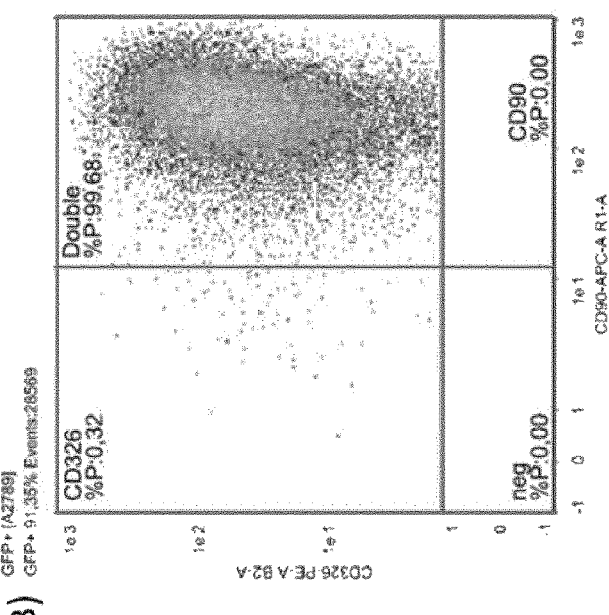
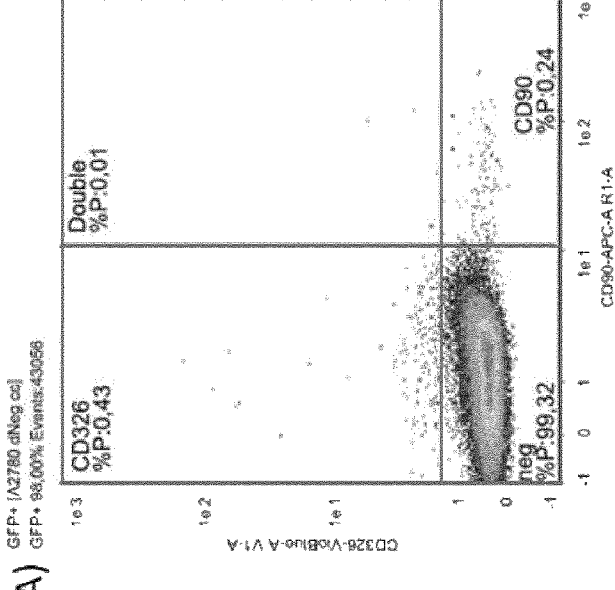
Figure 6 A, B

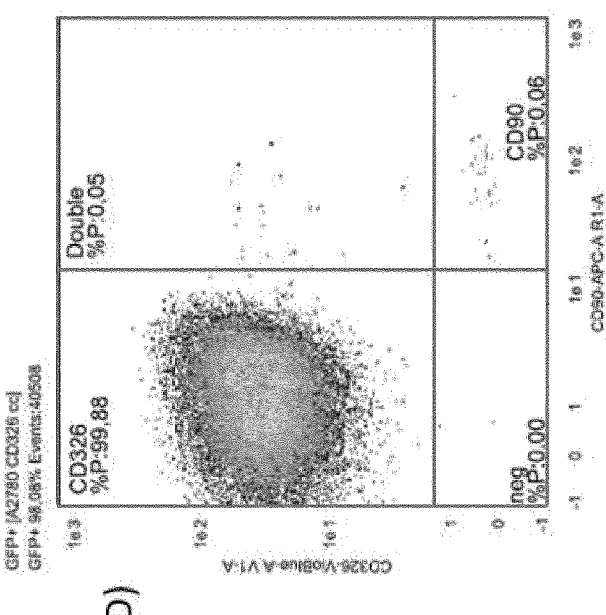
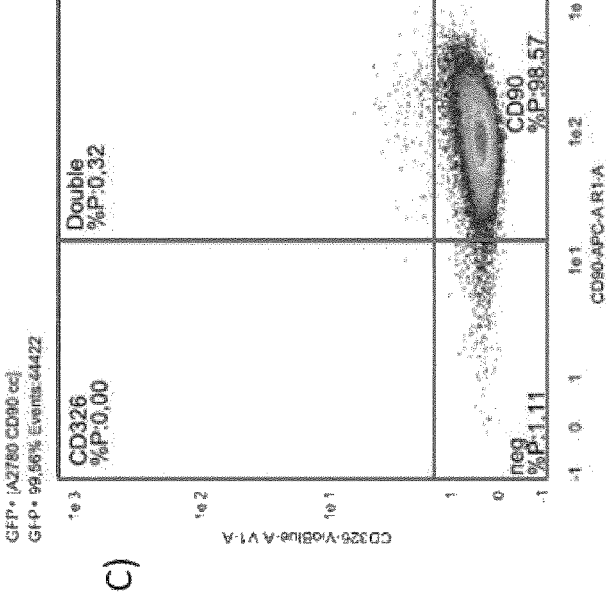
Figure 6 C, D

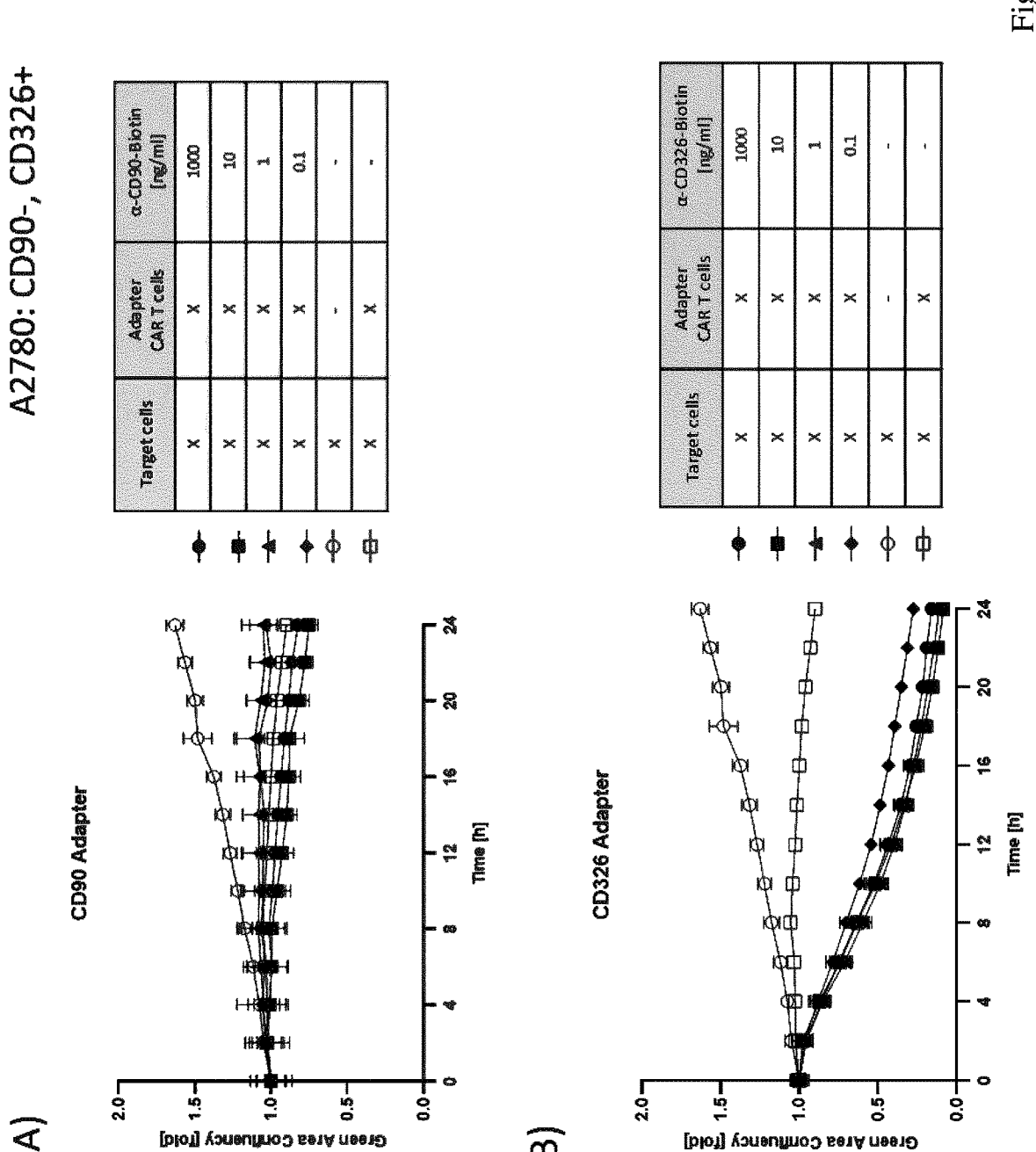
Figure 7 A, B

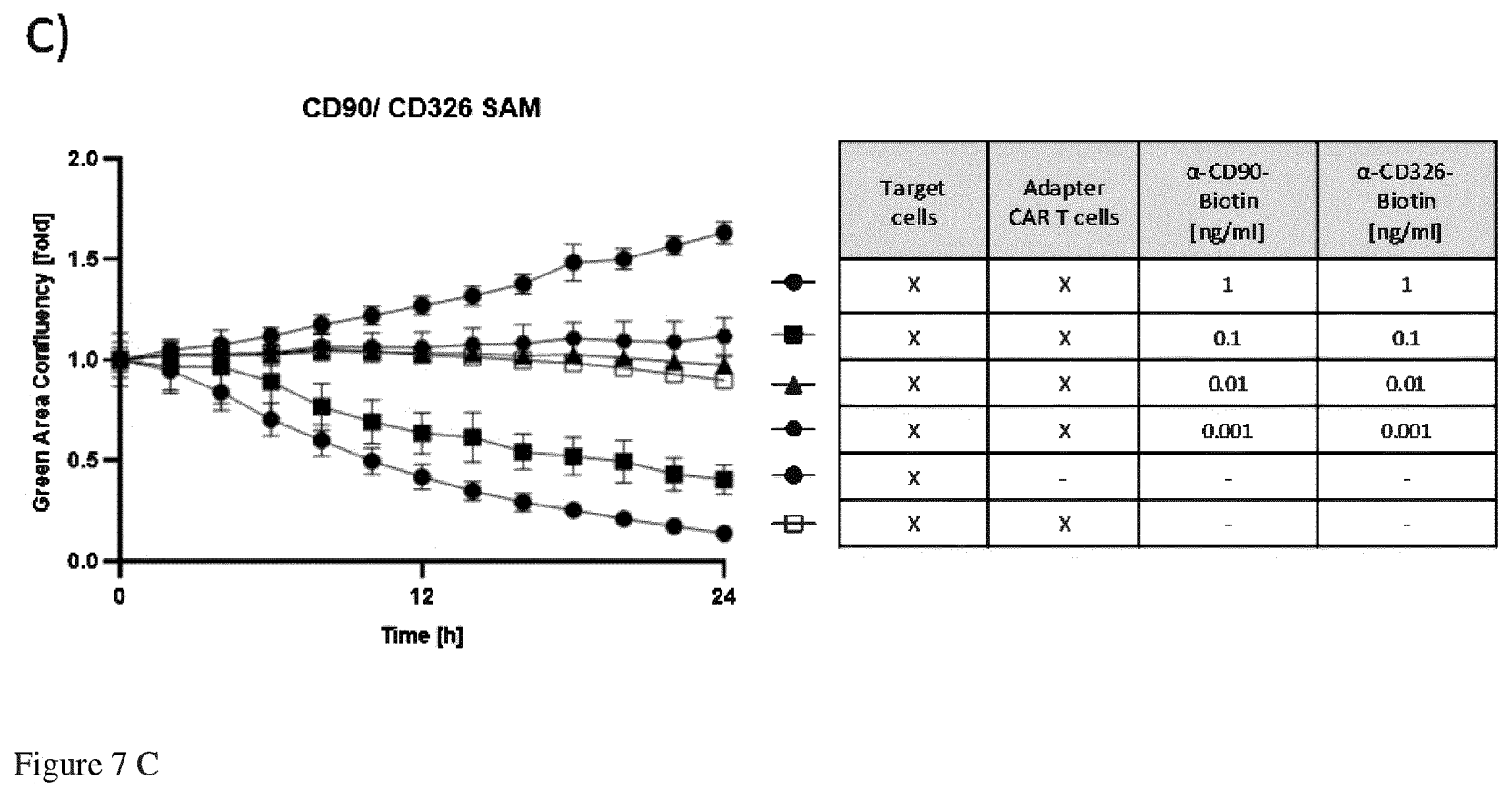

C)

CD90/ CD326 SAM

| Target cells | Adapter CAR T cells | α-CD90-Biotin [ng/ml] | α-CD326-Biotin [ng/ml] |
|---|---|---|---|
| X | X | 1 | 1 |
| X | X | 0.1 | 0.1 |
| X | X | 0.01 | 0.01 |
| X | X | 0.001 | 0.001 |
| X | - | - | - |
| X | X | - | - |

Figure 7 C

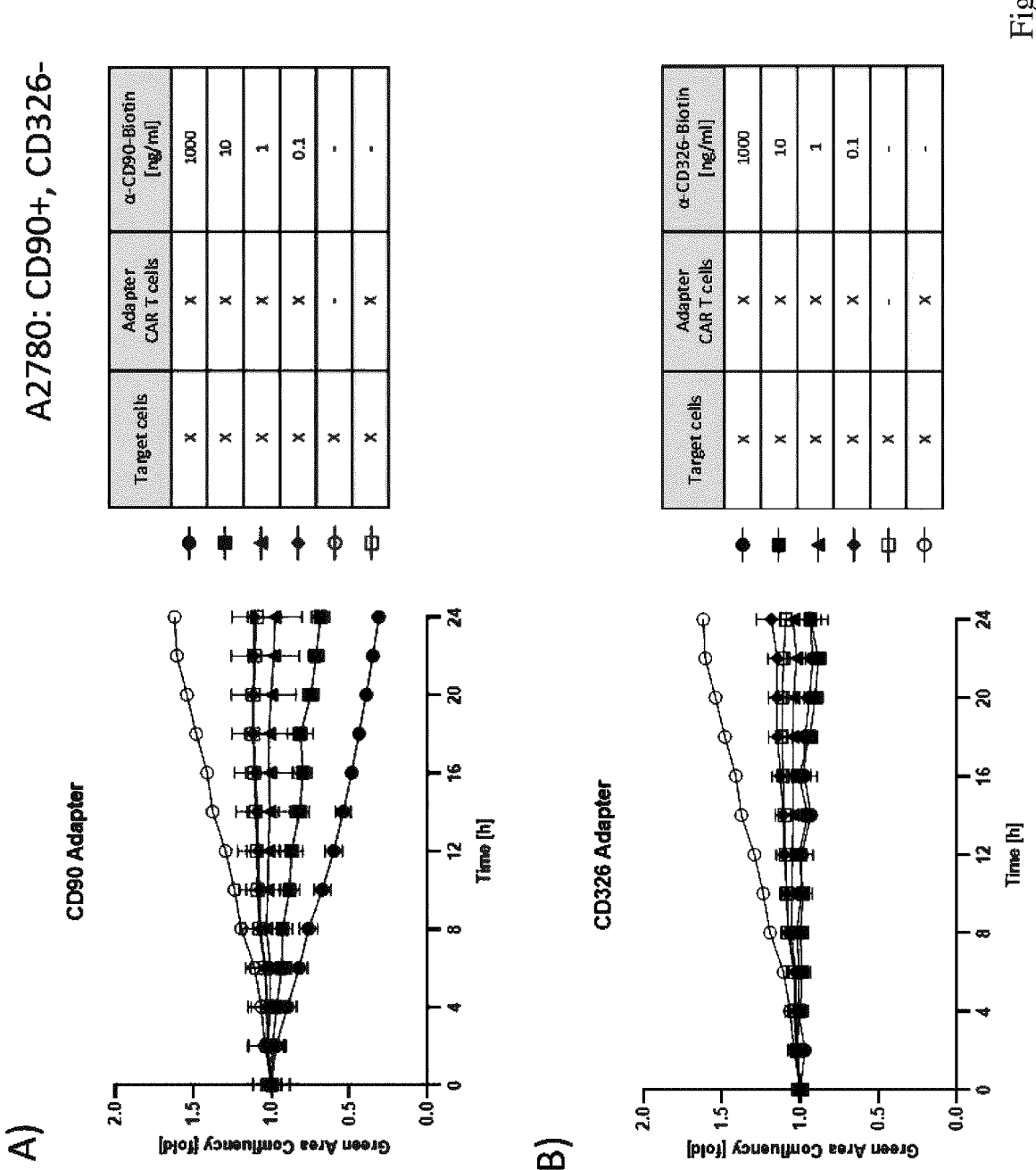
Figure 8 A, B

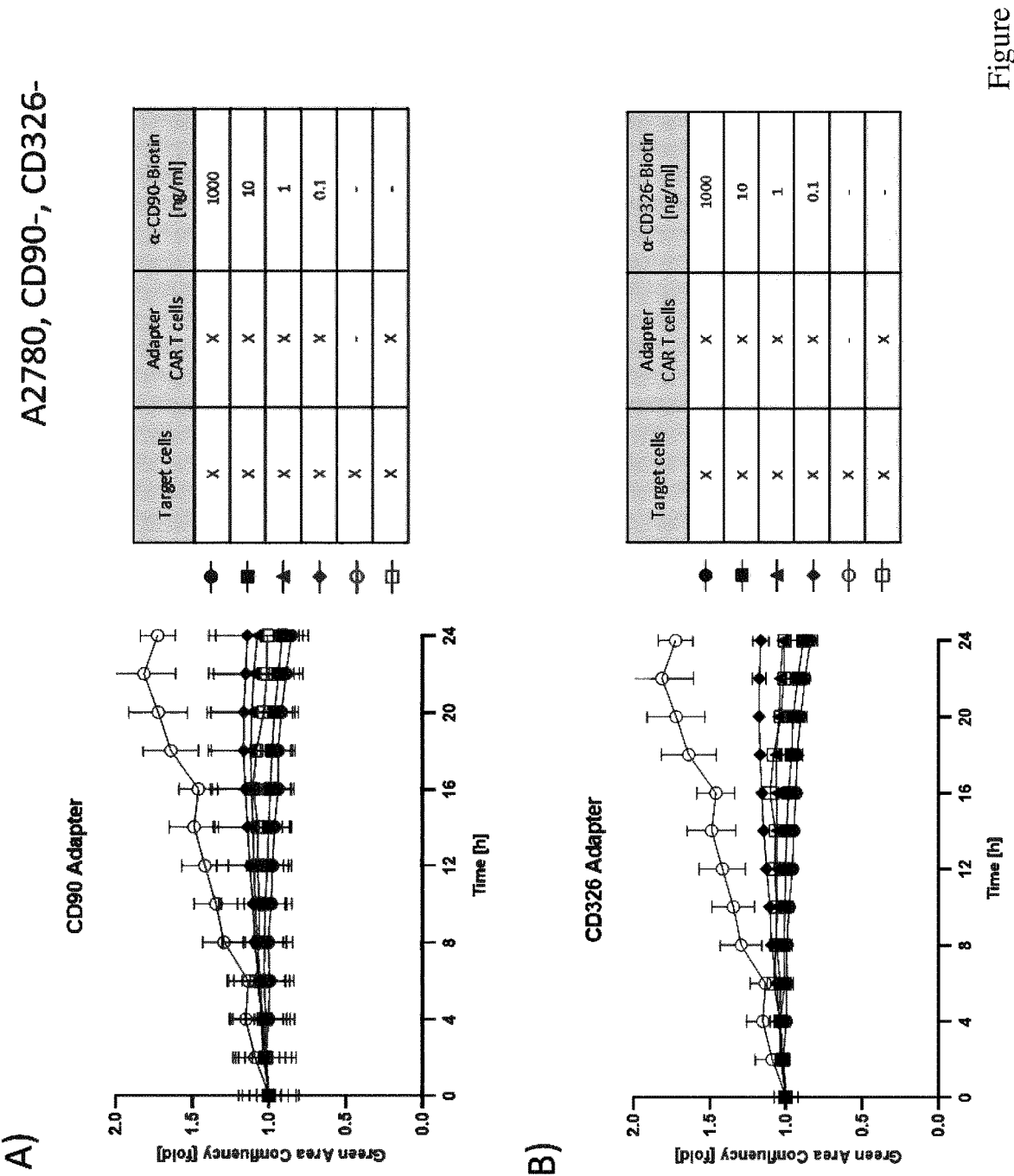
Figure 9 A, B

Figure 9C:
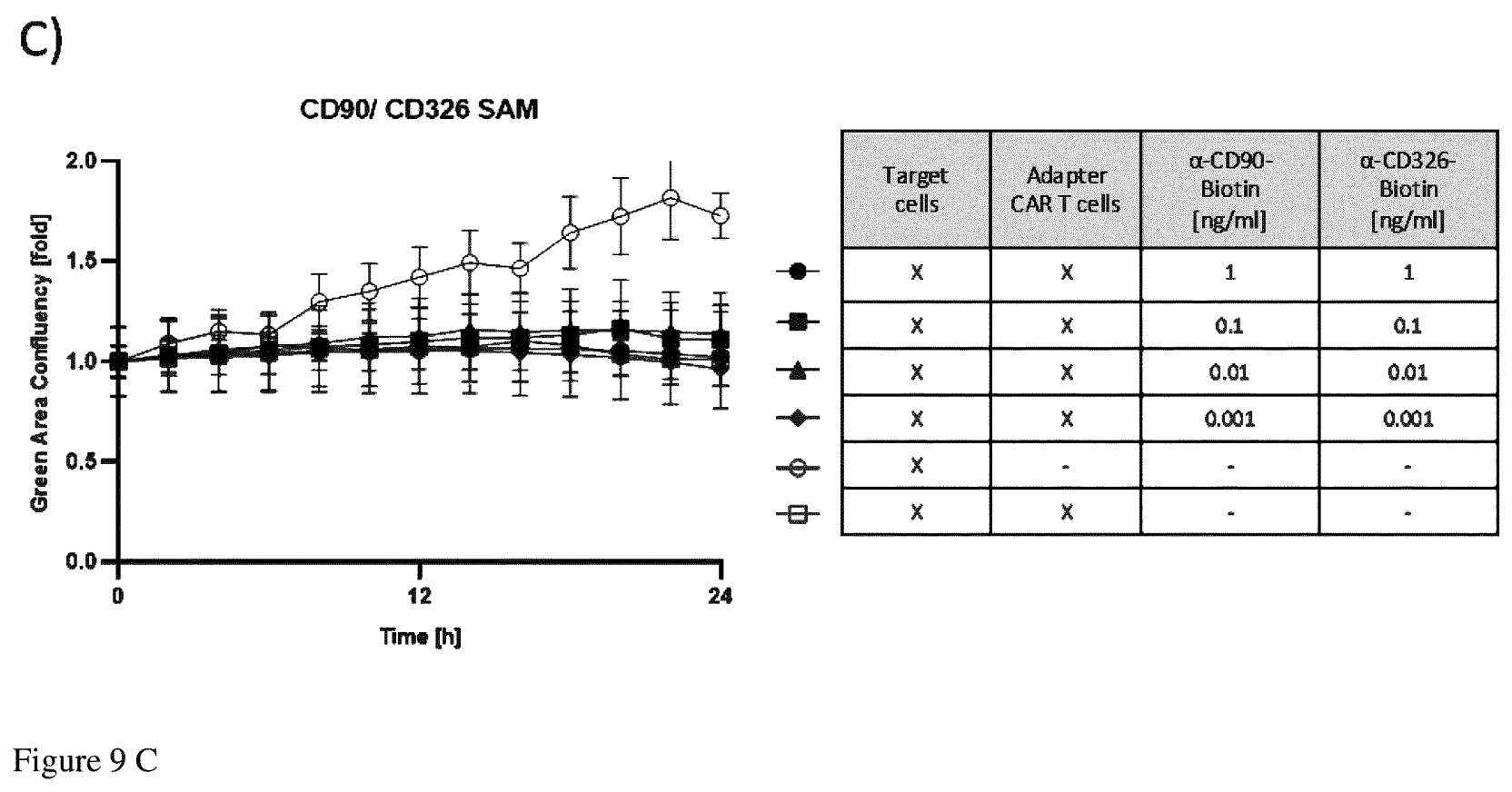

| Target cells | Adapter CAR T cells | α-CD90-Biotin [ng/ml] | α-CD326-Biotin [ng/ml] |
|---|---|---|---|
| X | X | 1 | 1 |
| X | X | 0.1 | 0.1 |
| X | X | 0.01 | 0.01 |
| X | X | 0.001 | 0.001 |
| X | - | - | - |
| X | X | - | - |

CD90/ CD326 SAM

Green Area Confluency [fold]

Time [h]

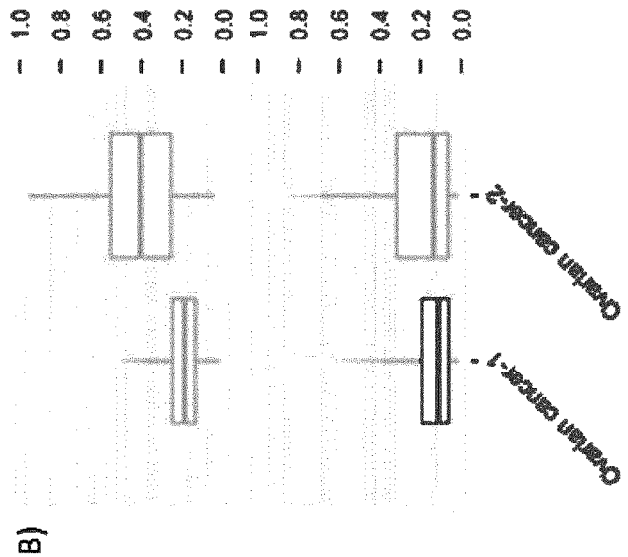
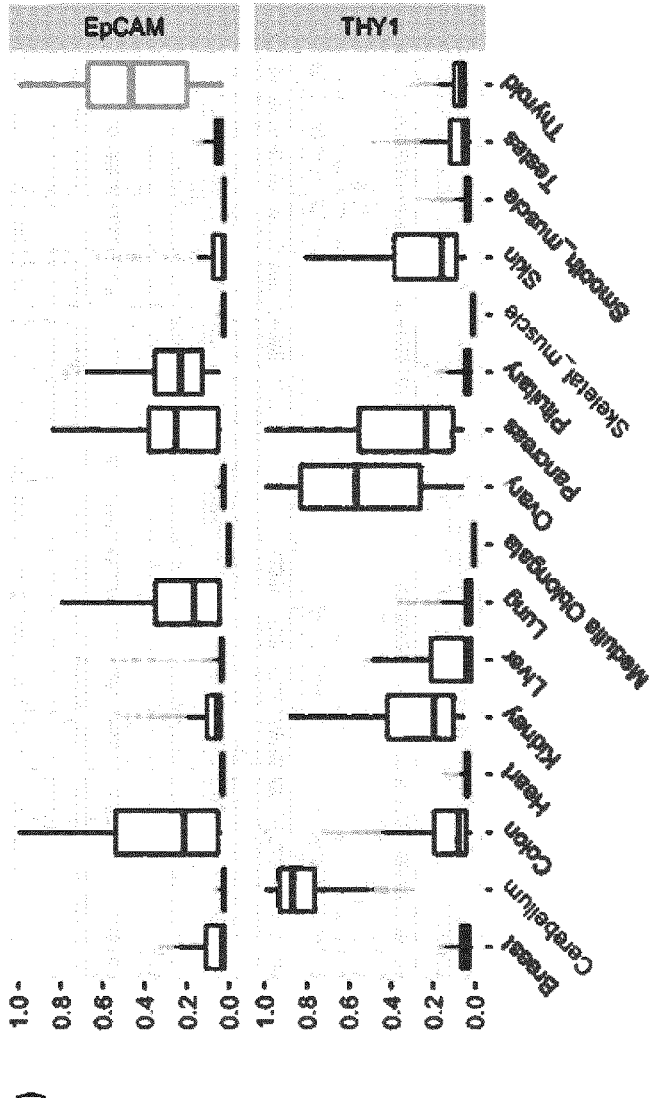
Figure 11

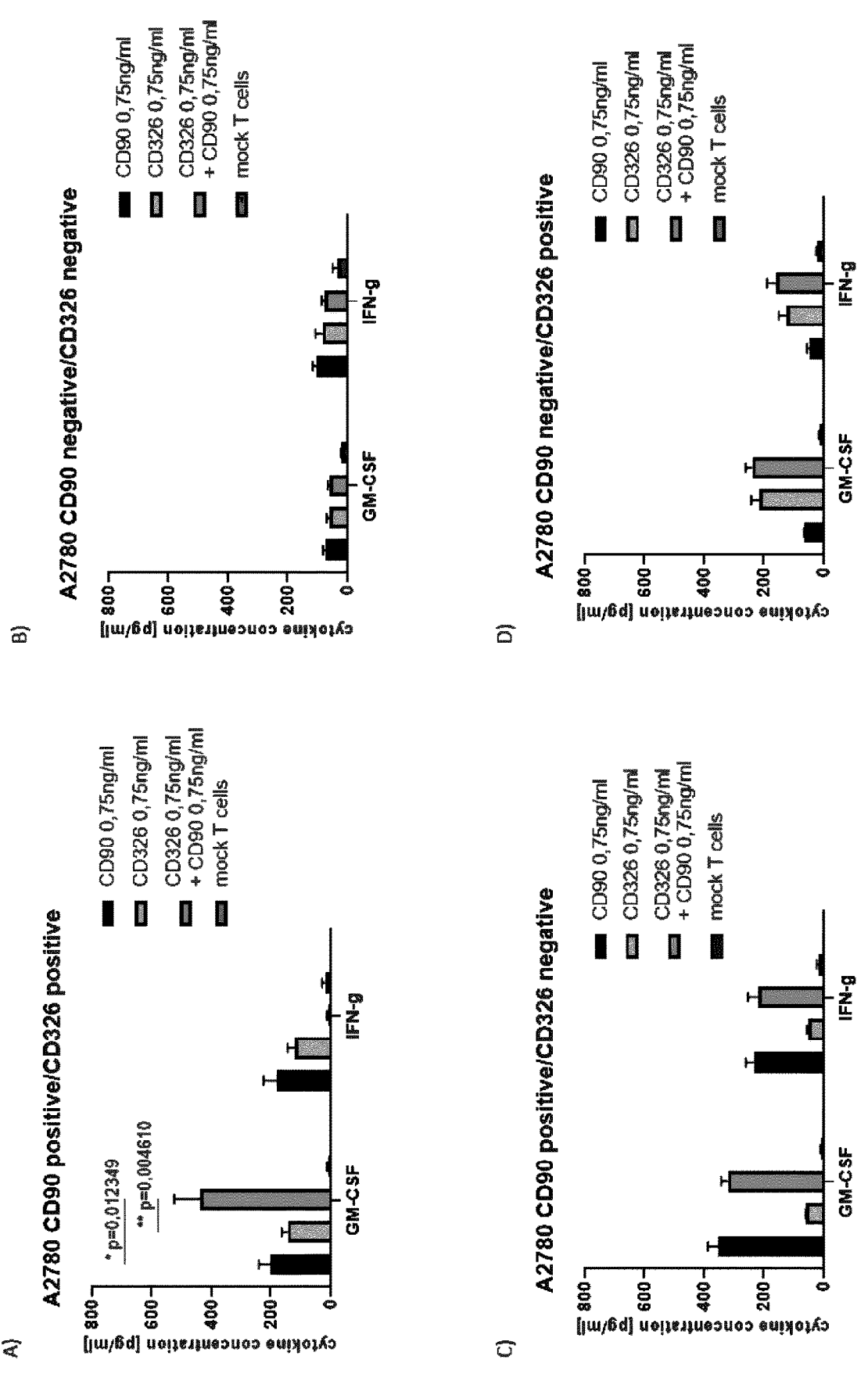
Figure 23 A-D

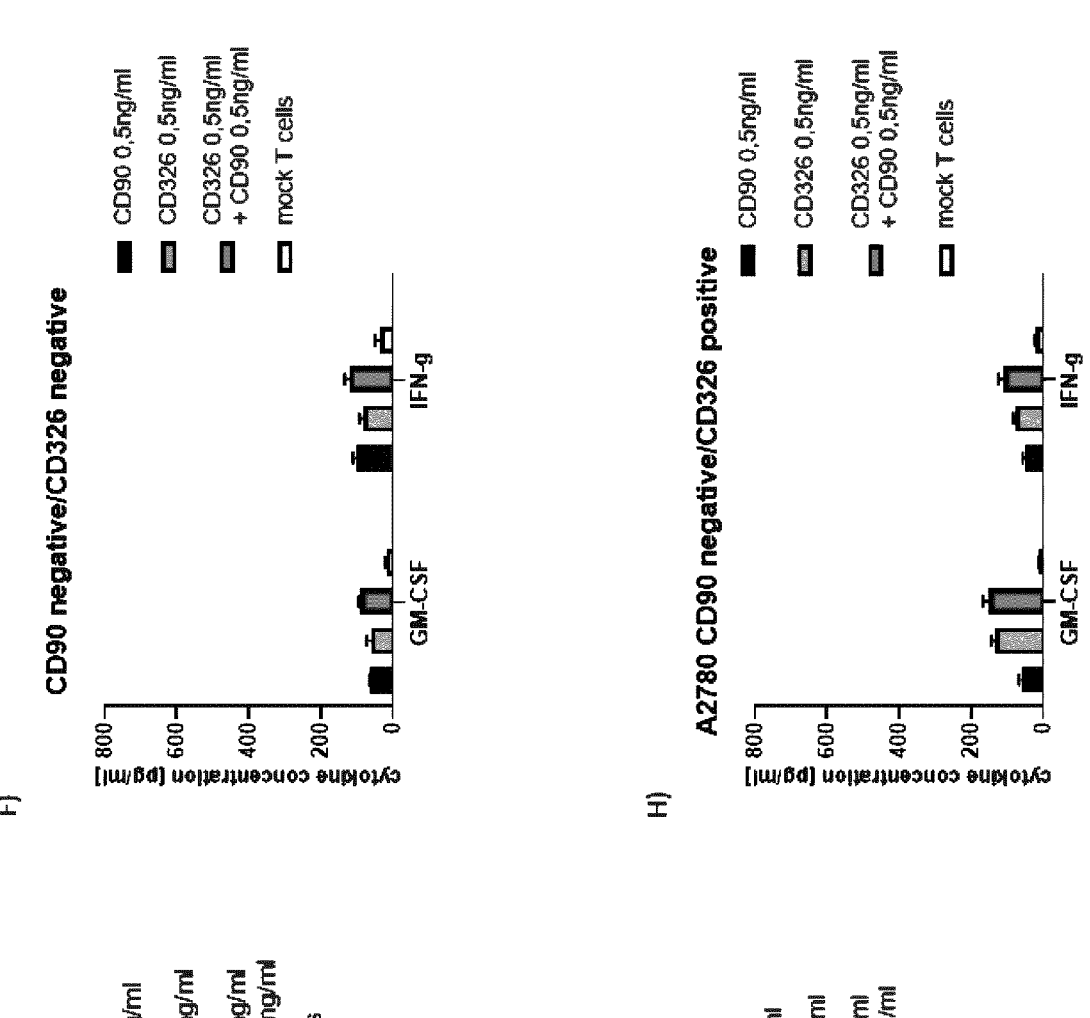
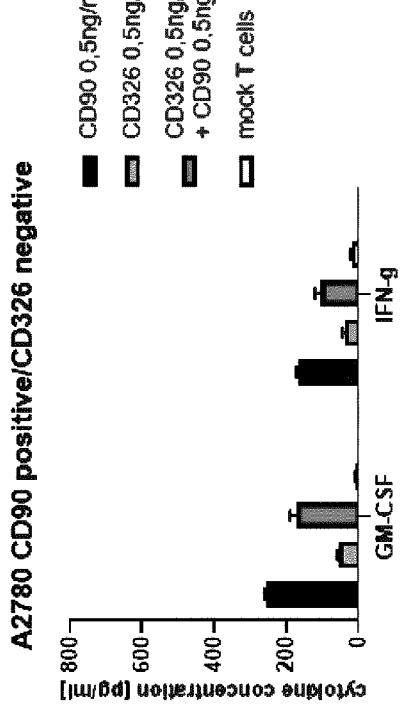
Figure 23 E-H

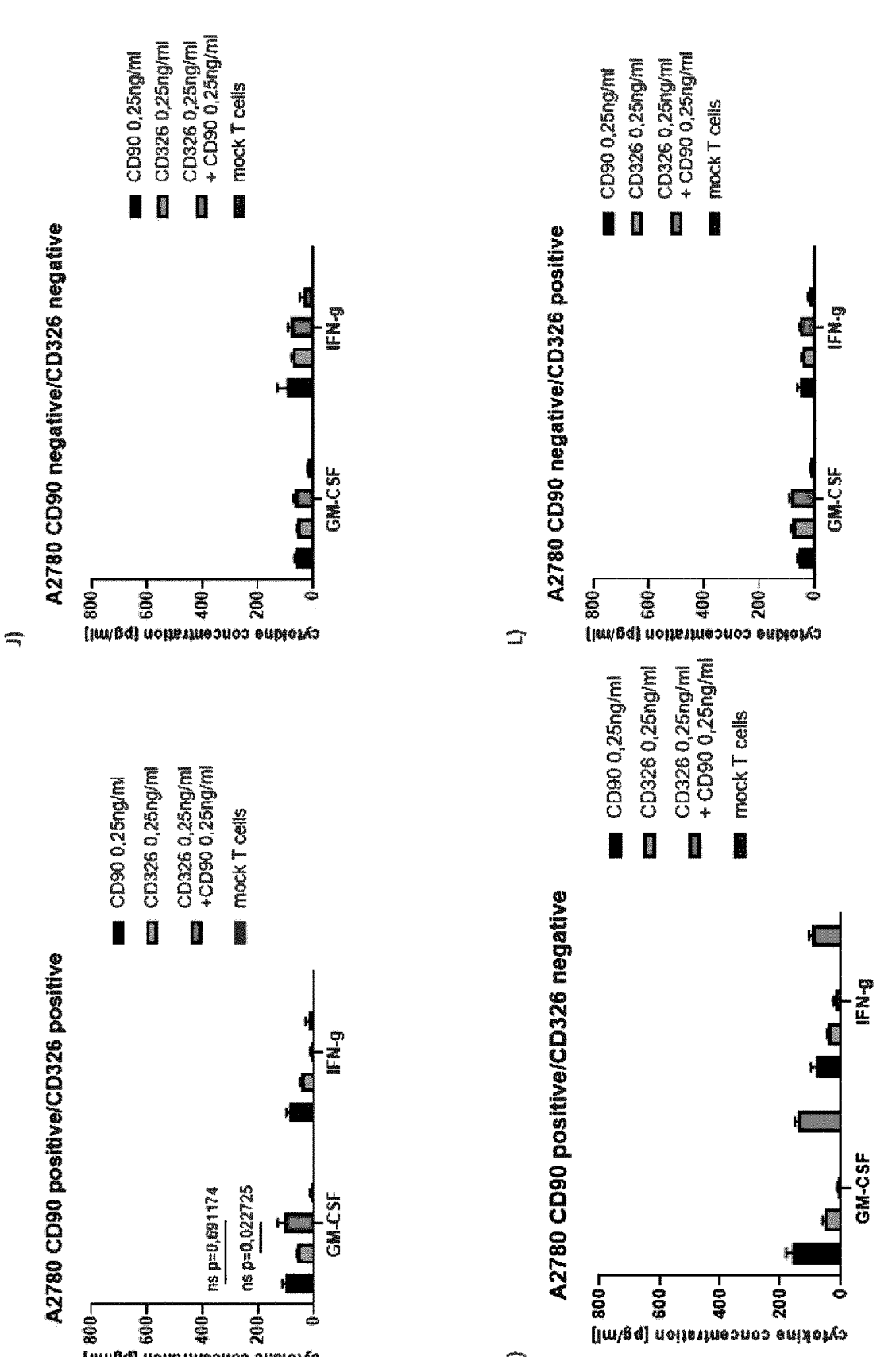
Figure 23 I-L

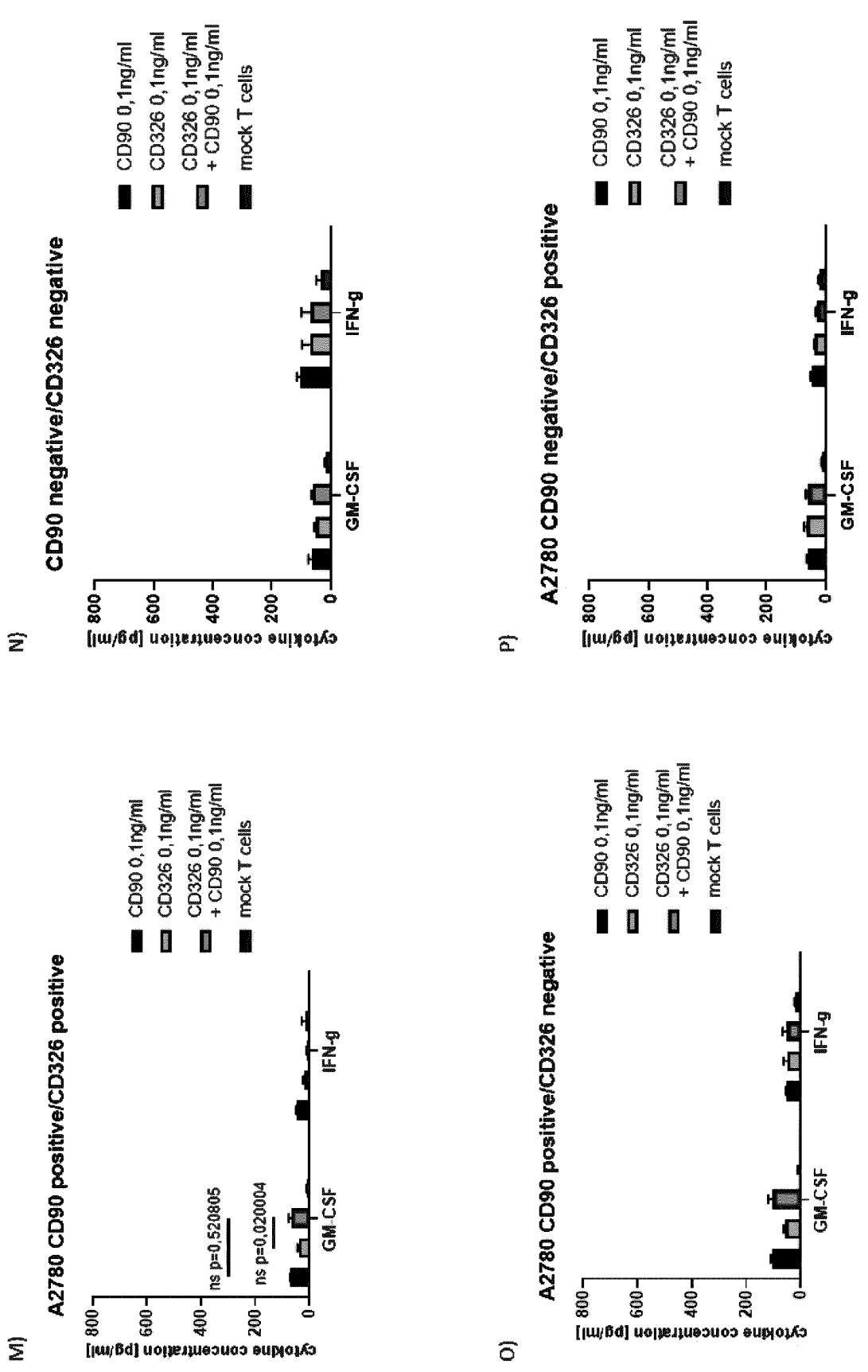
Figure 23 M-P

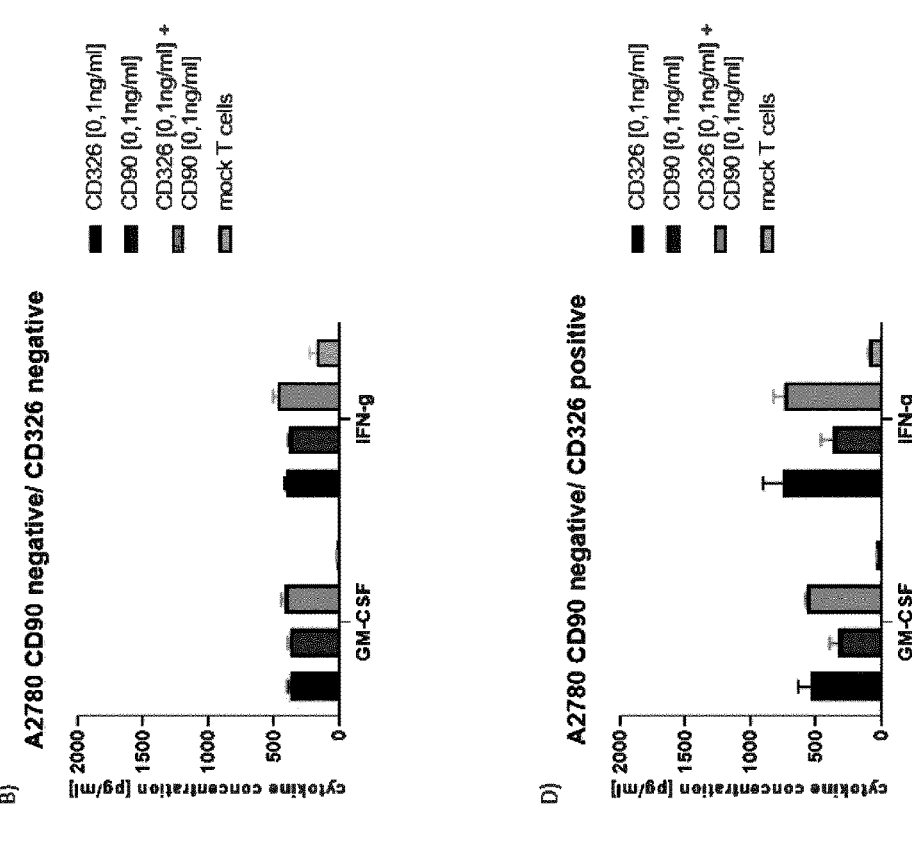
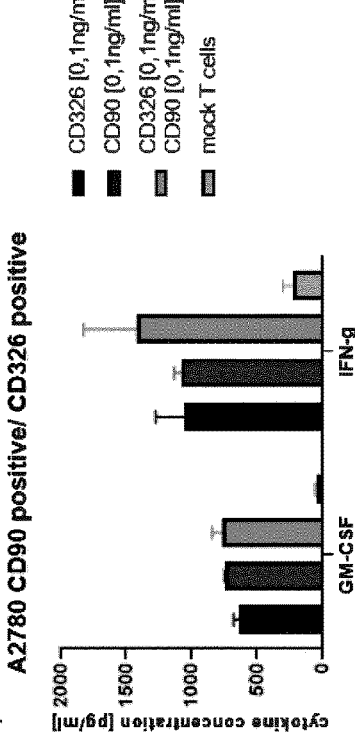
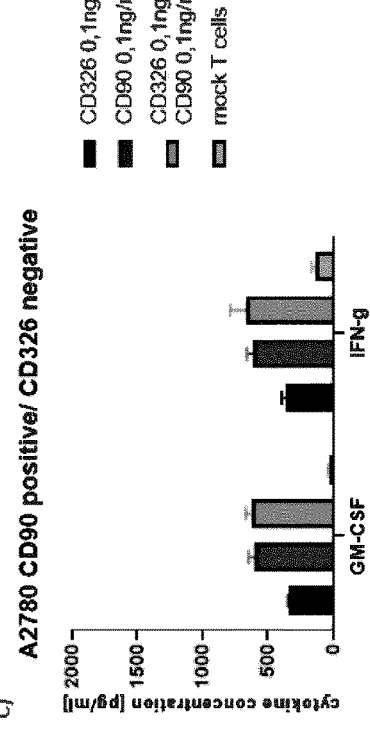
Figure 24 A-D

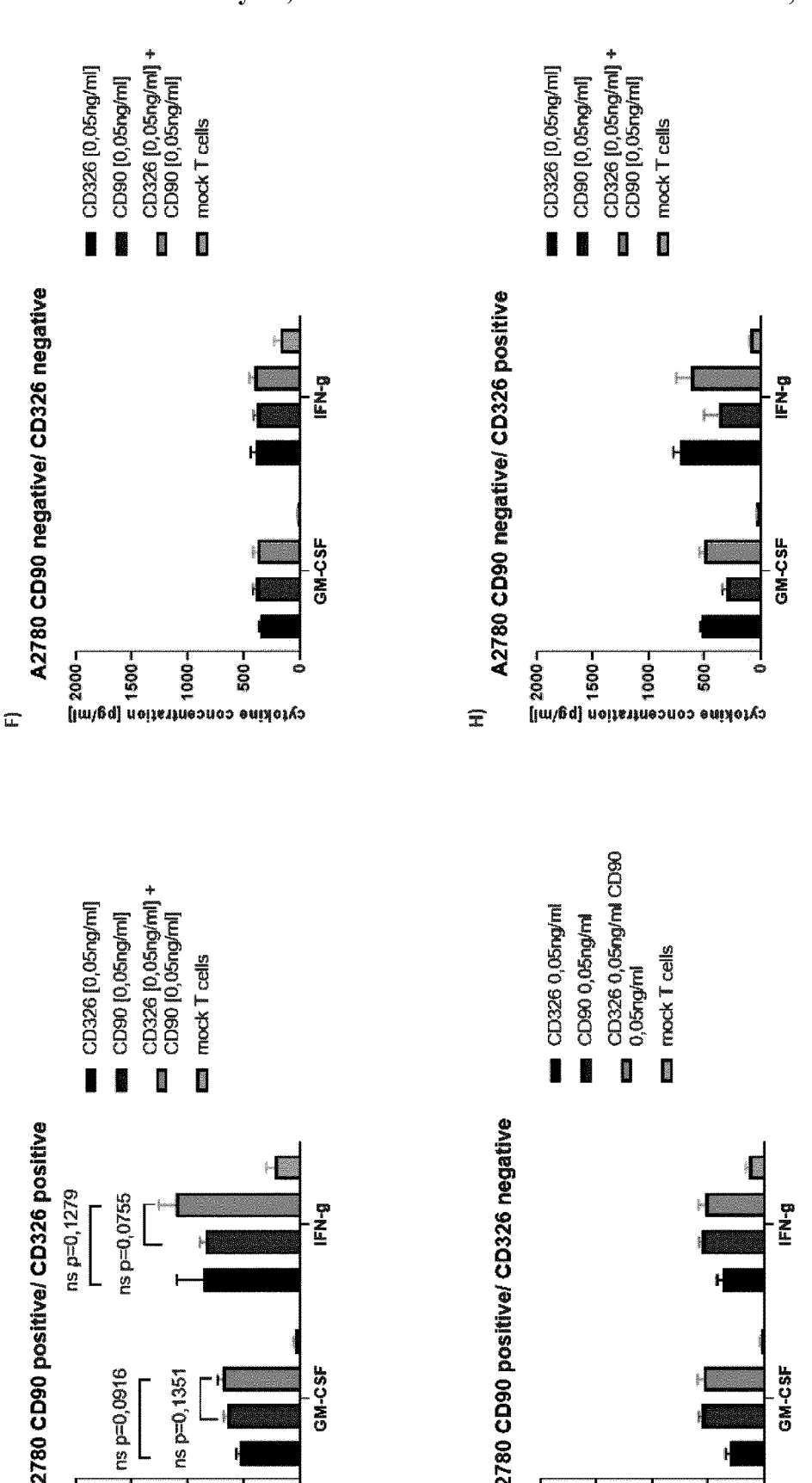
Figure 24 E-H

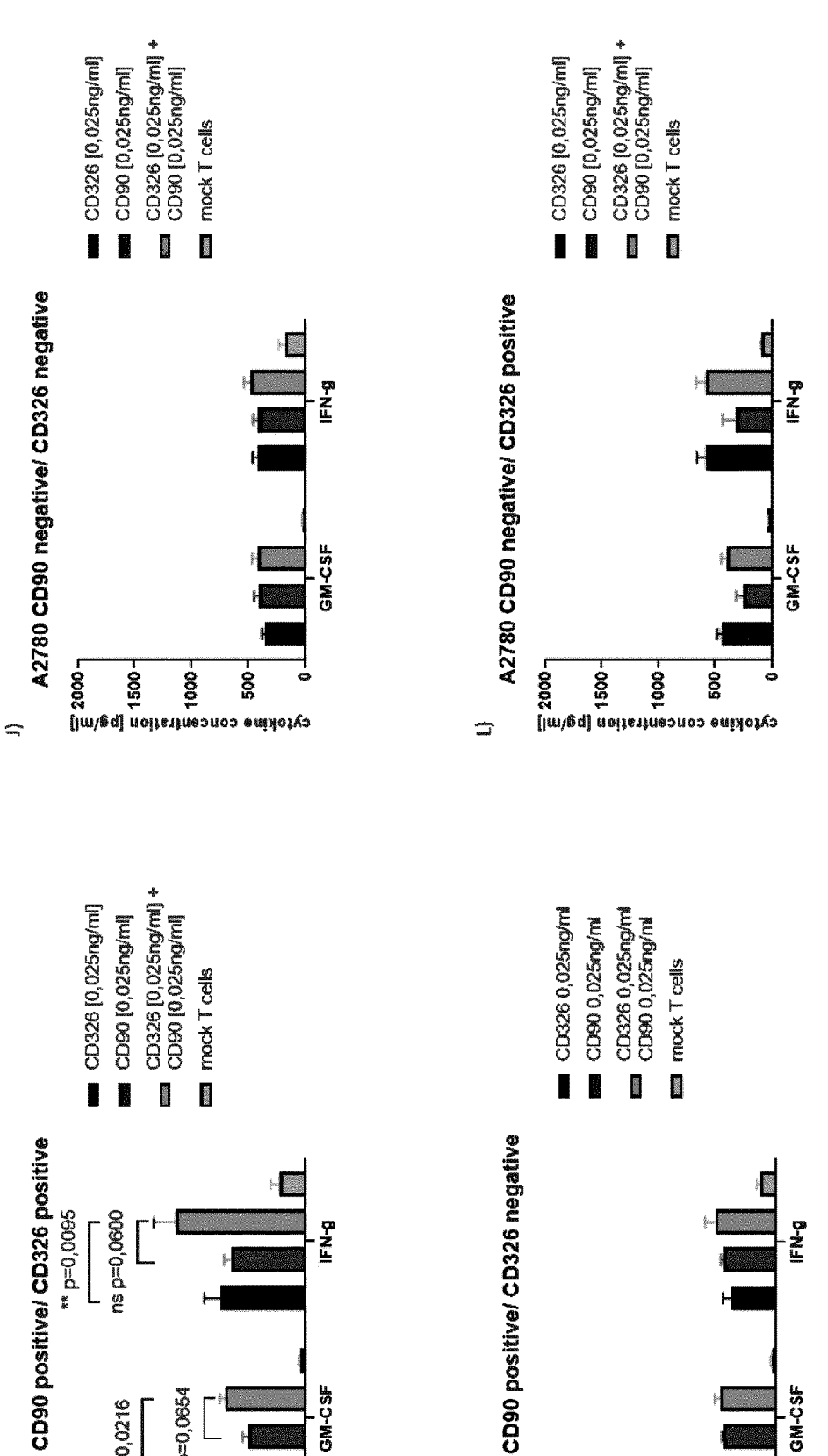
Figure 24 I-L

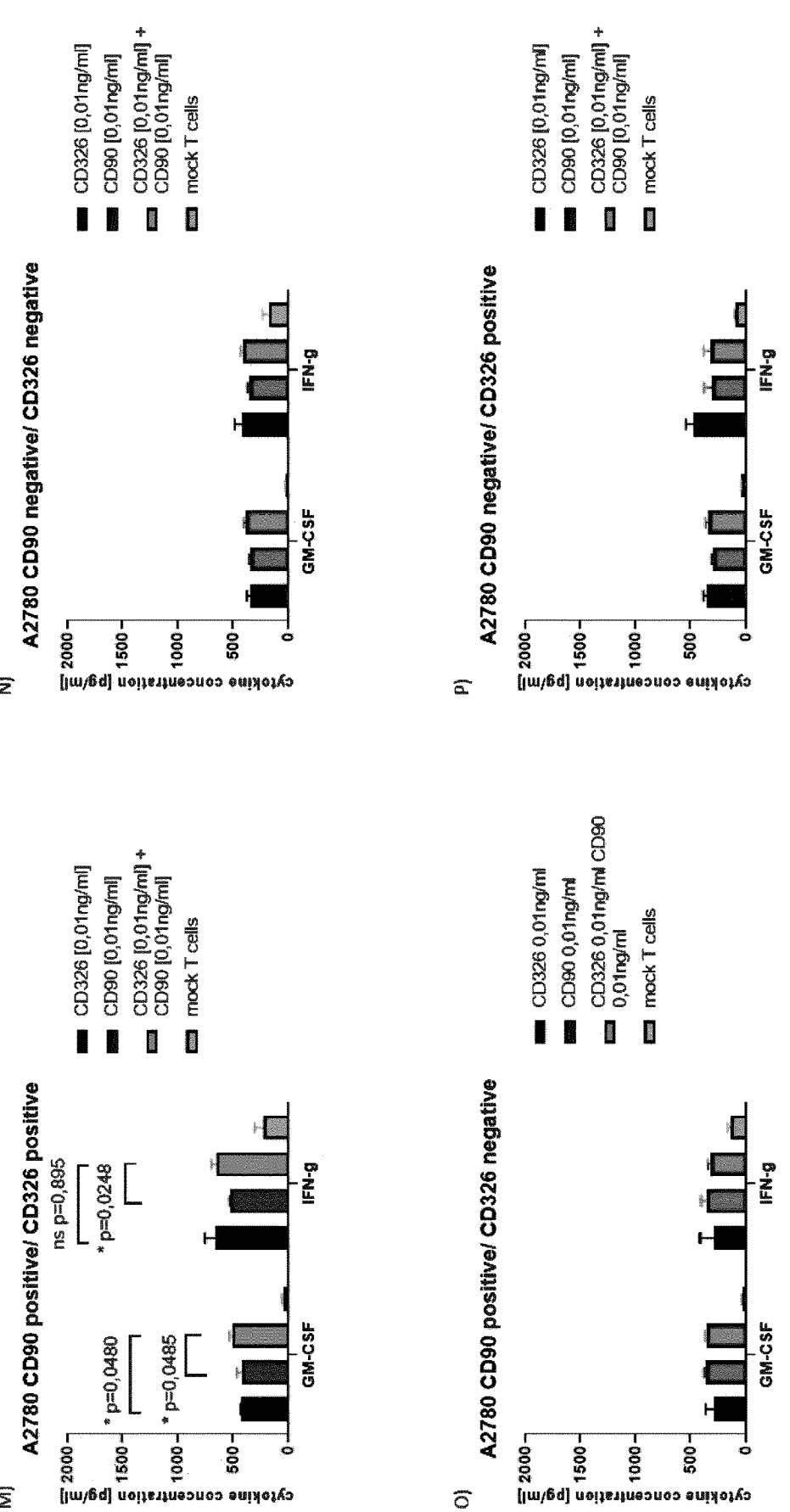
Figure 24 M-P

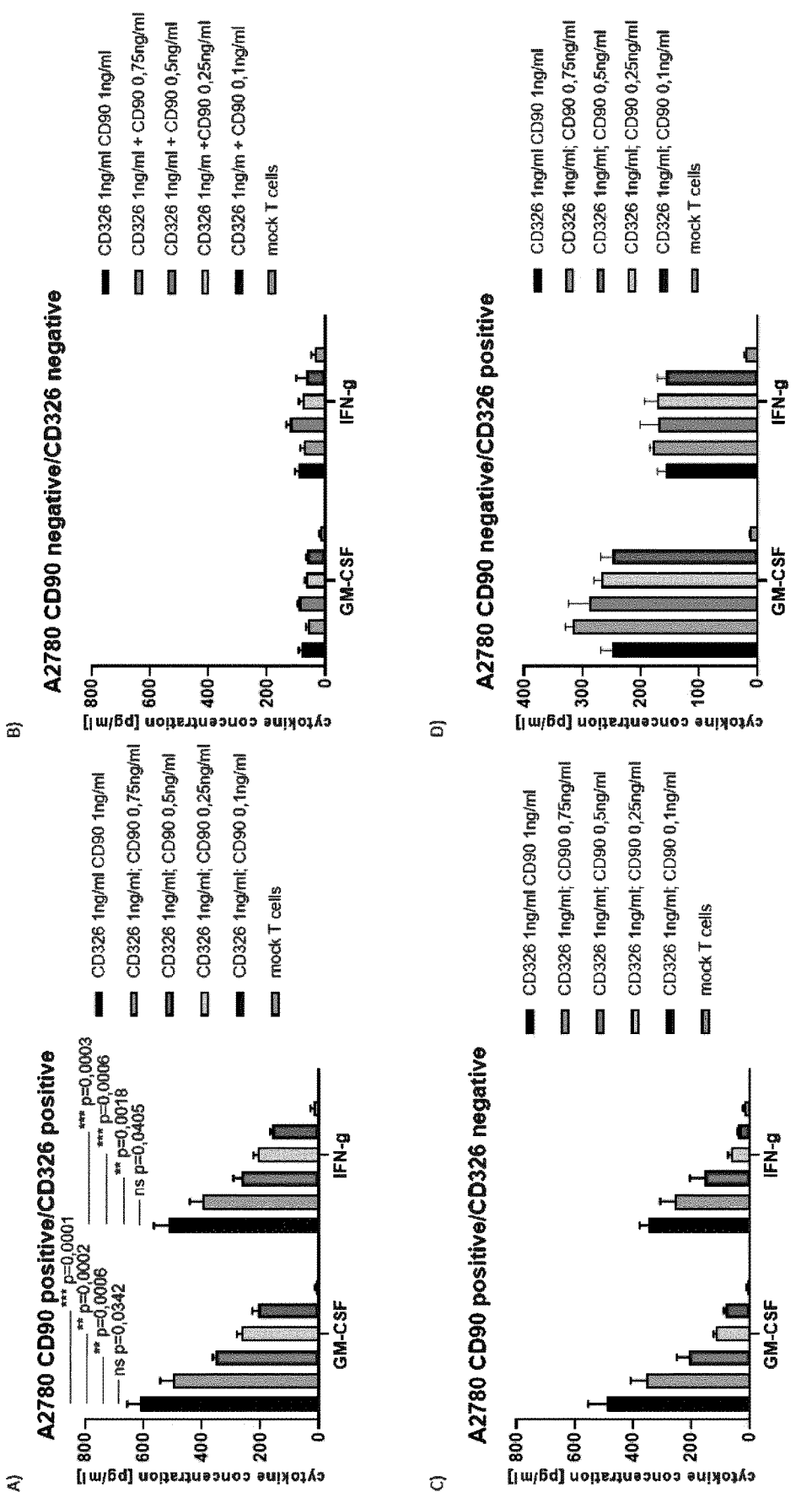
Figure 25 A-D

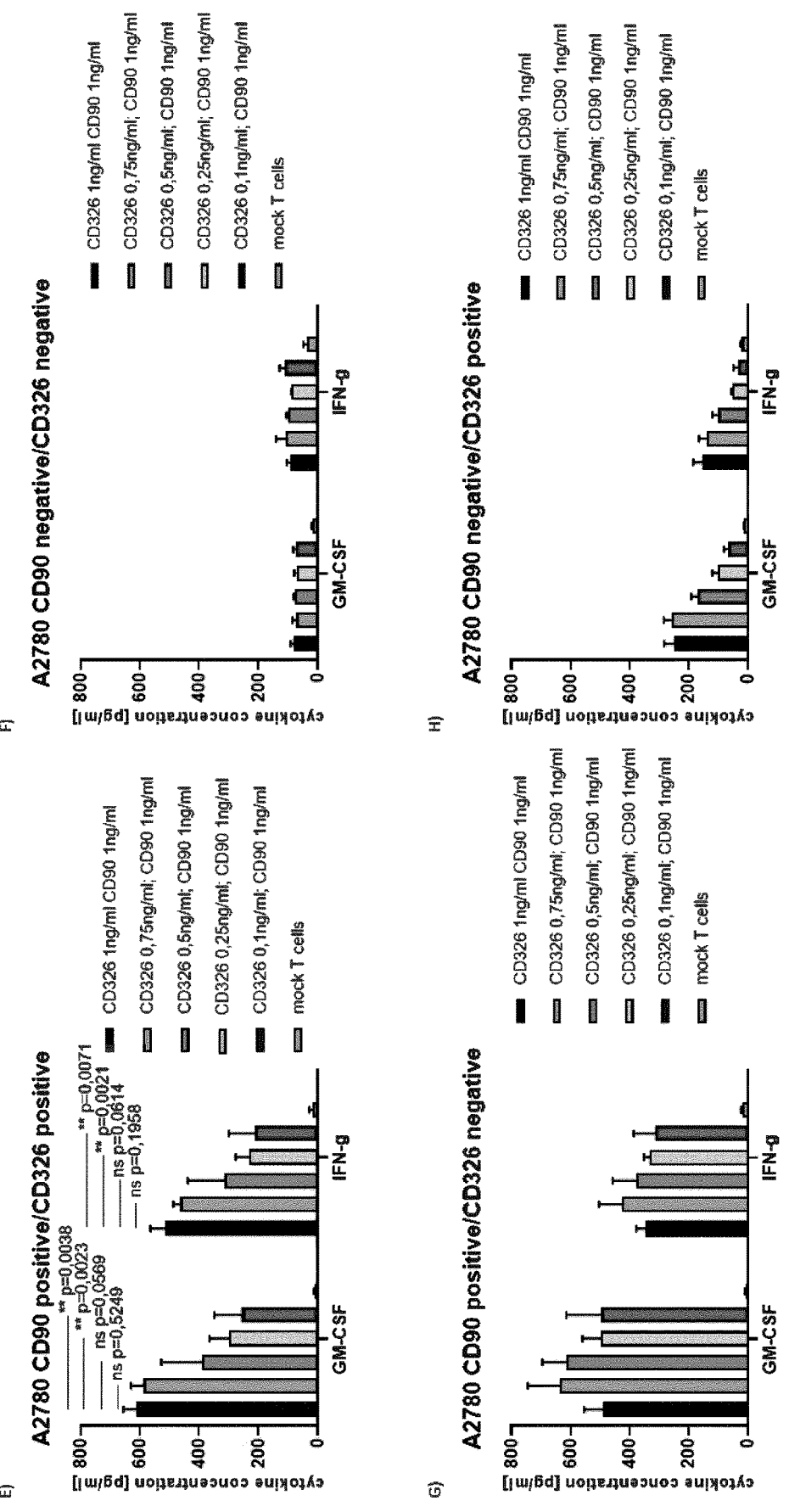
Figure 25 E-H

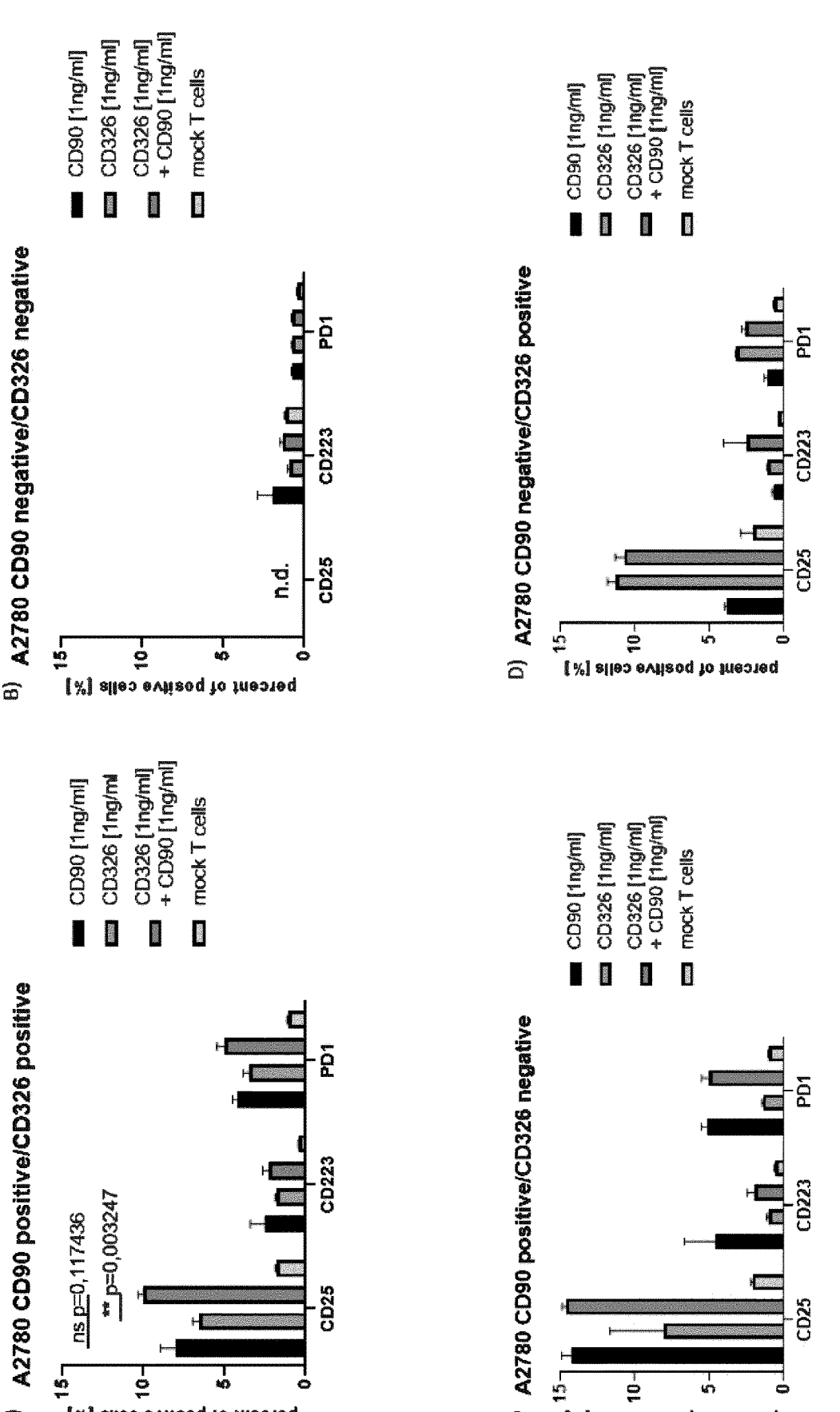
Figure 26 A-D

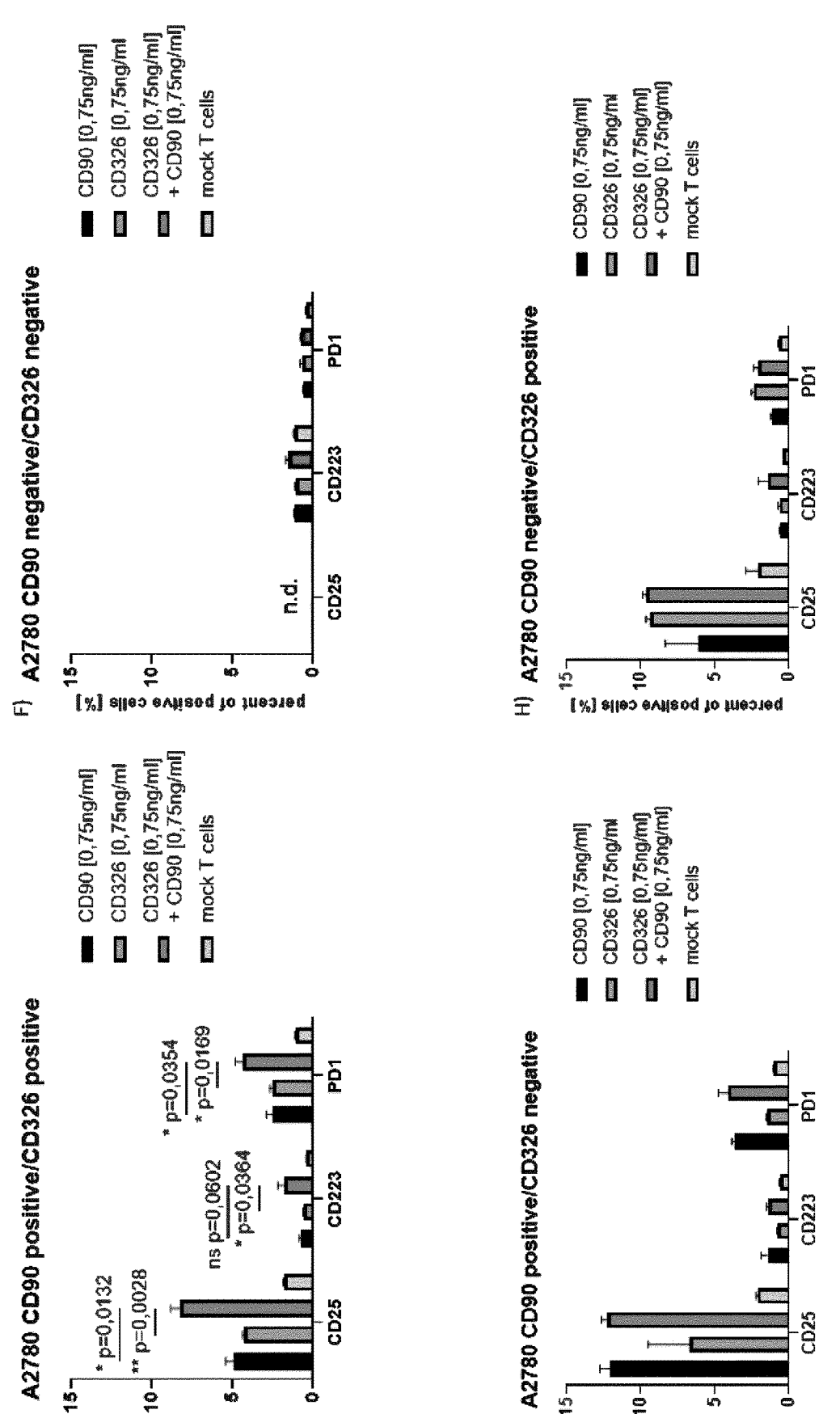
Figure 26 E-H

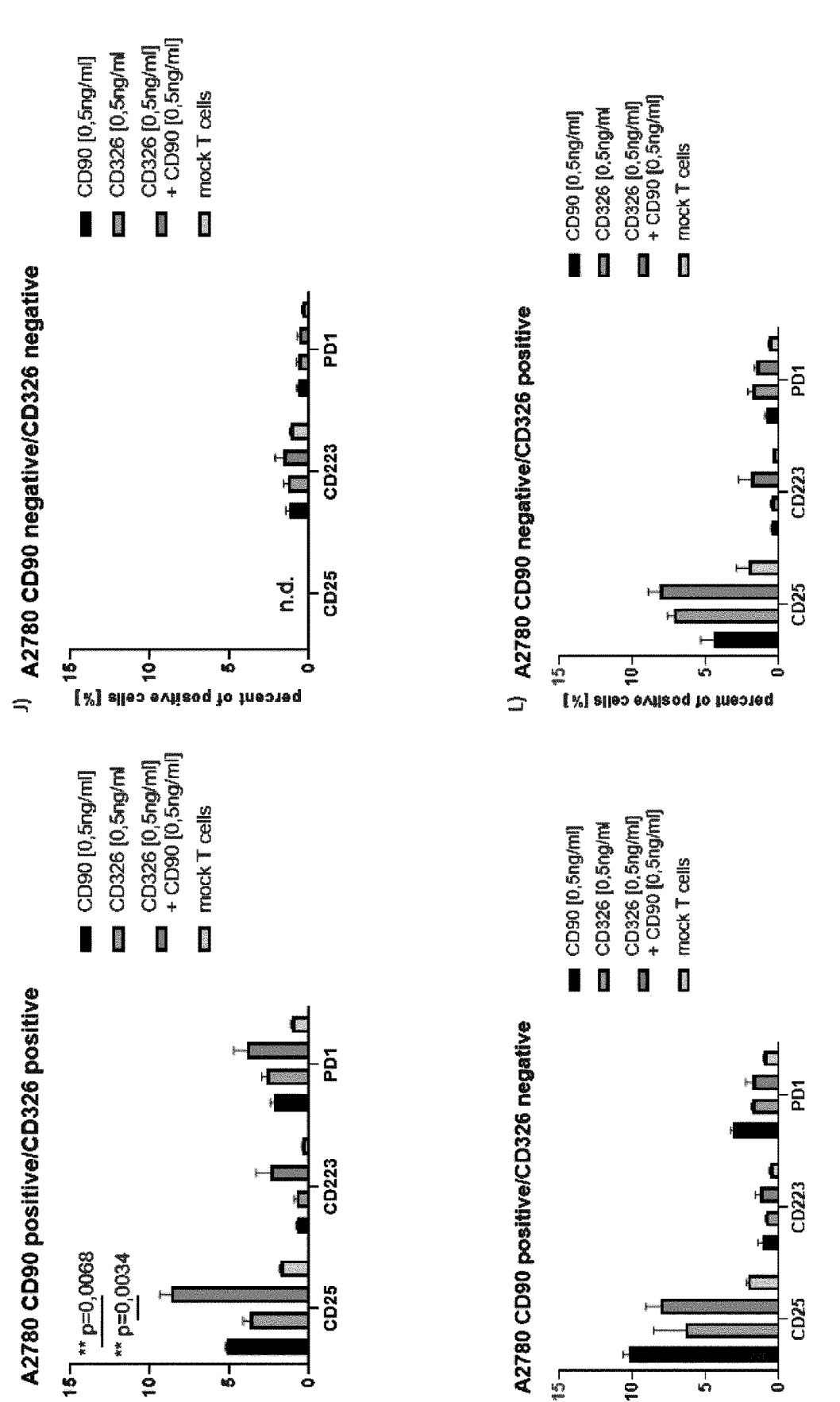
Figure 26 I-L

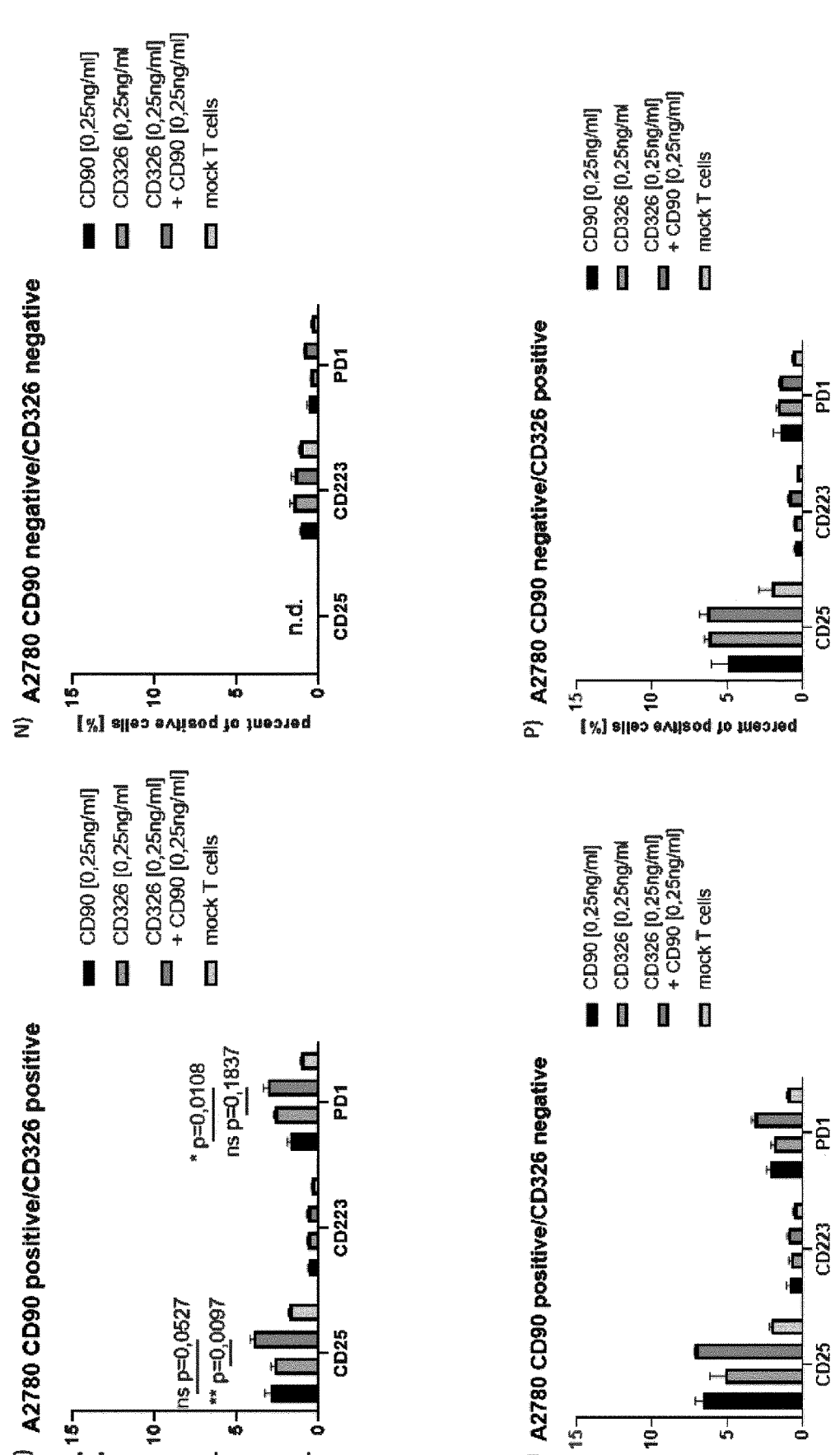
Figure 26 M-P

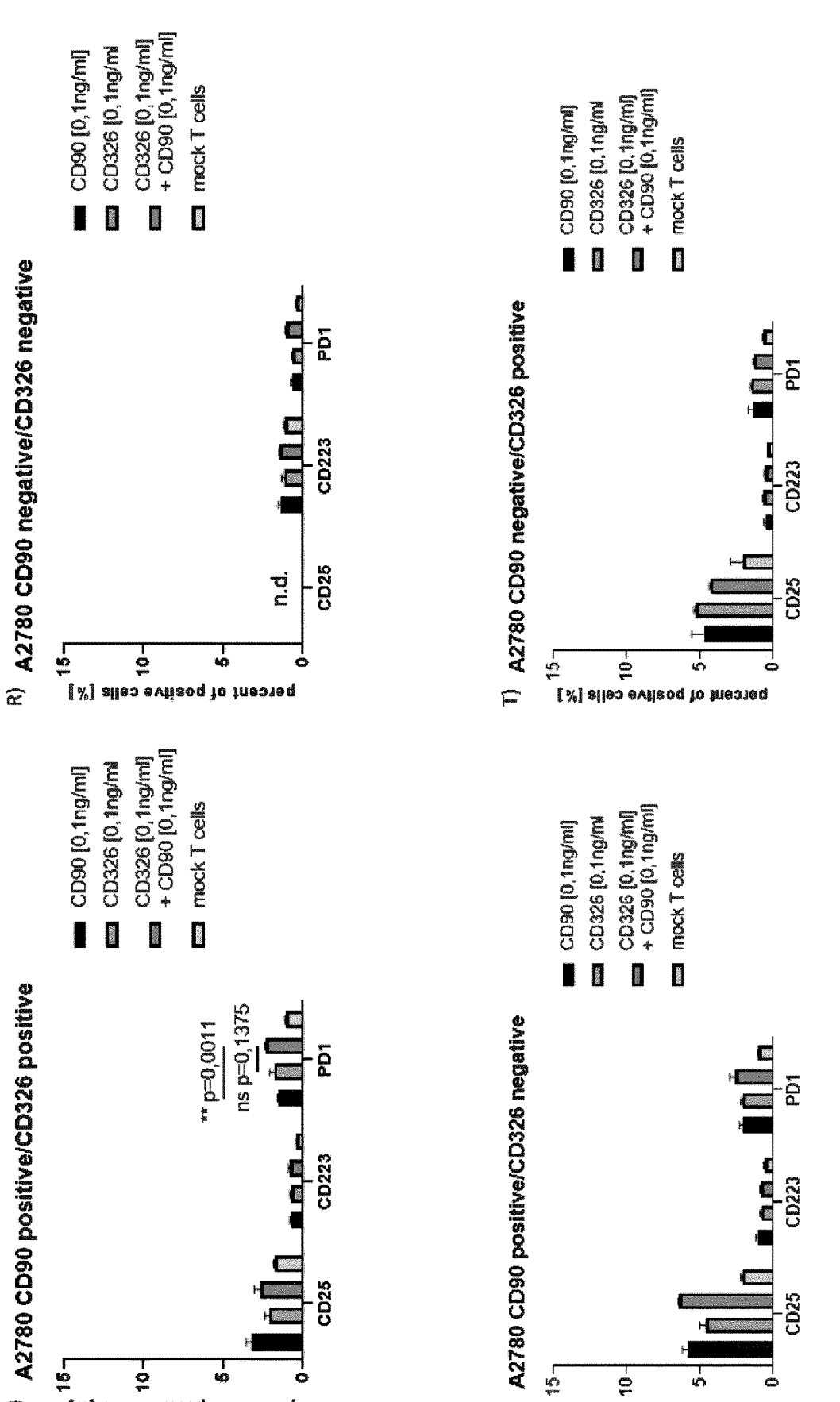
Figure 26 Q-T

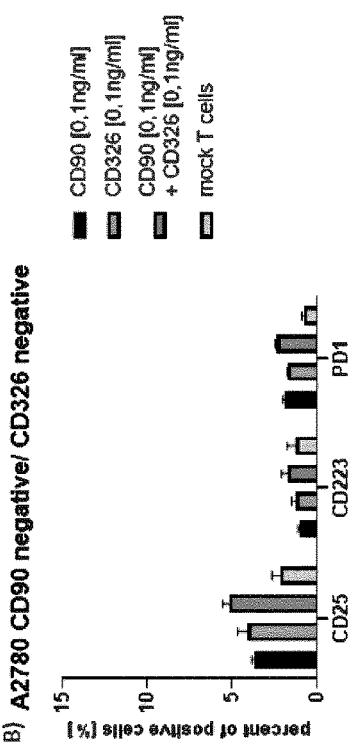
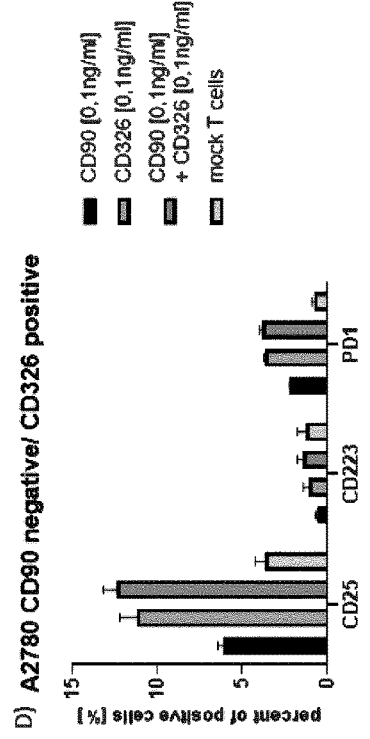
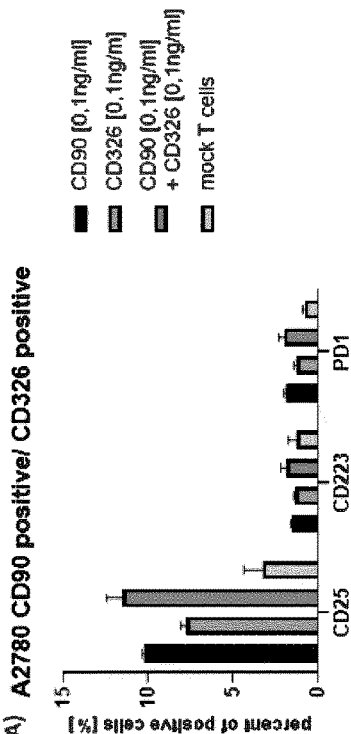
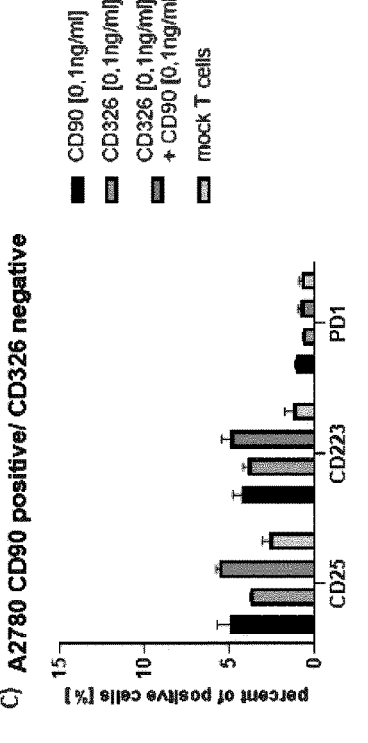
Figure 27 A-D

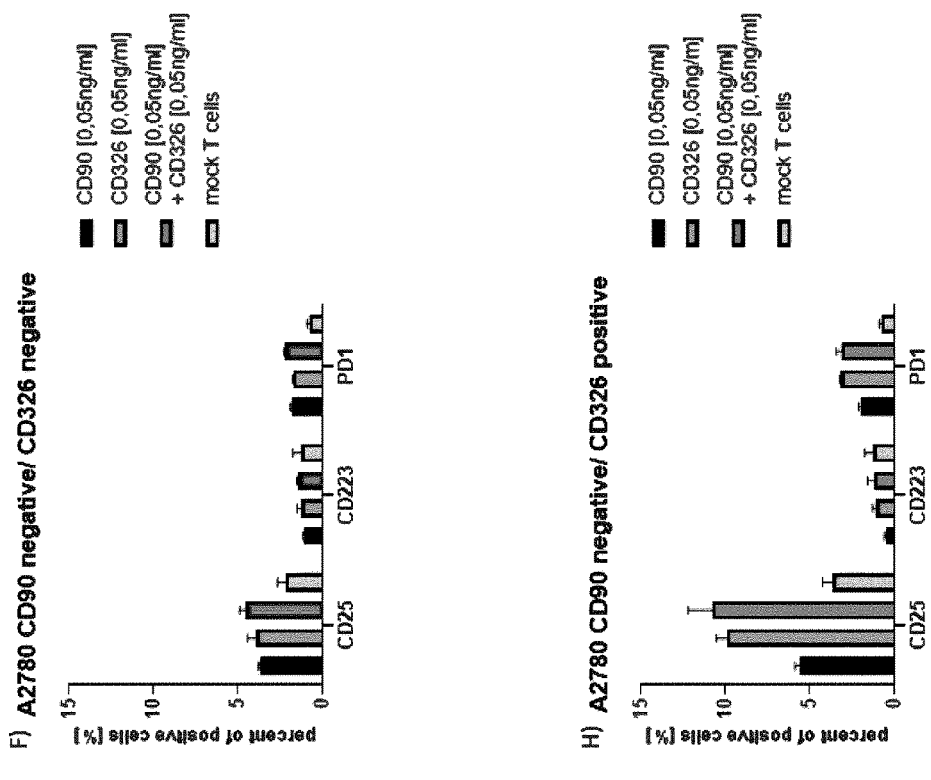
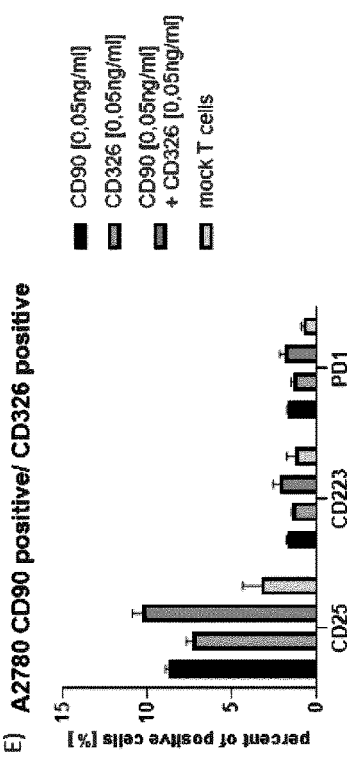
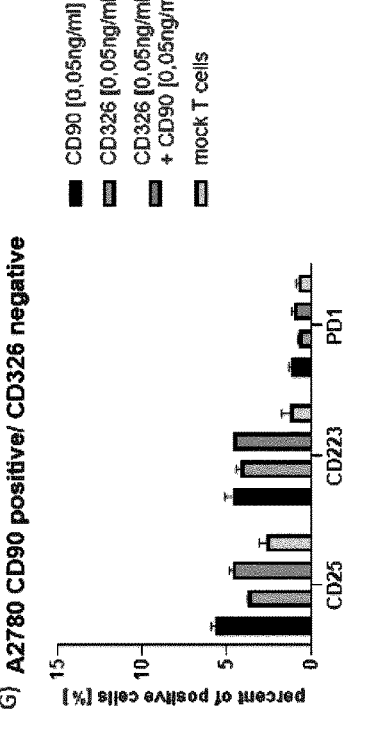
Figure 27 E-H

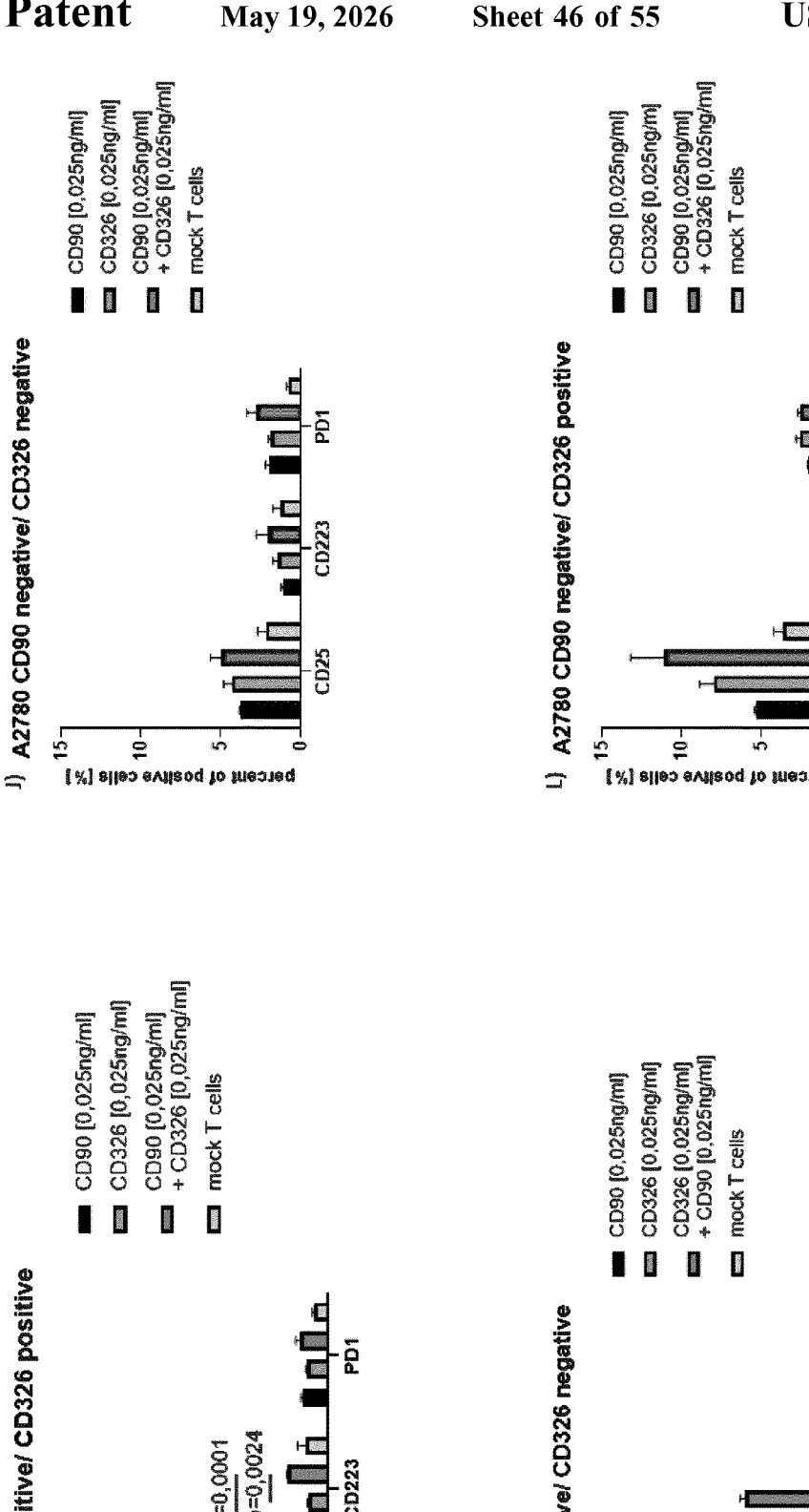
Figure 27 I-L

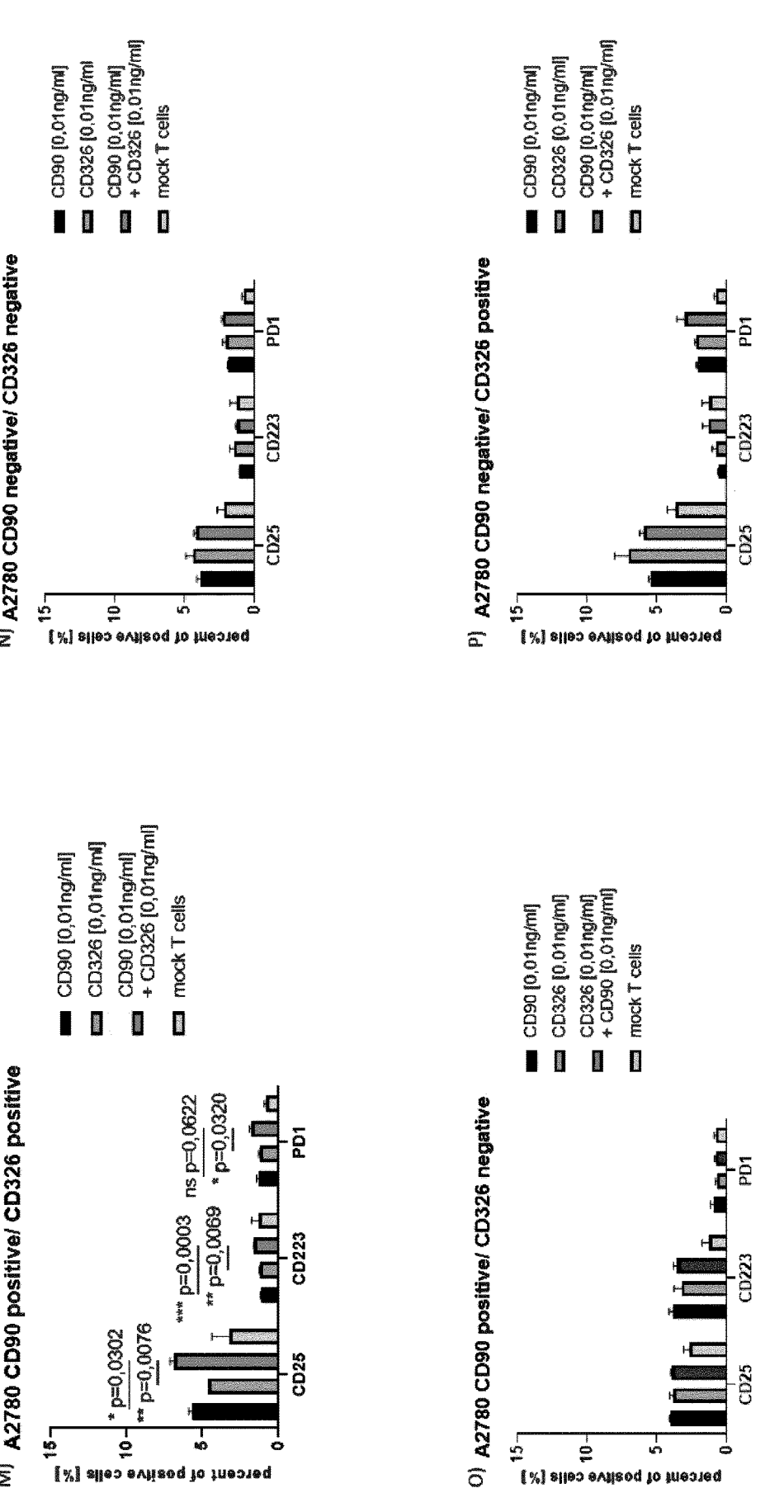
Figure 27 M-P

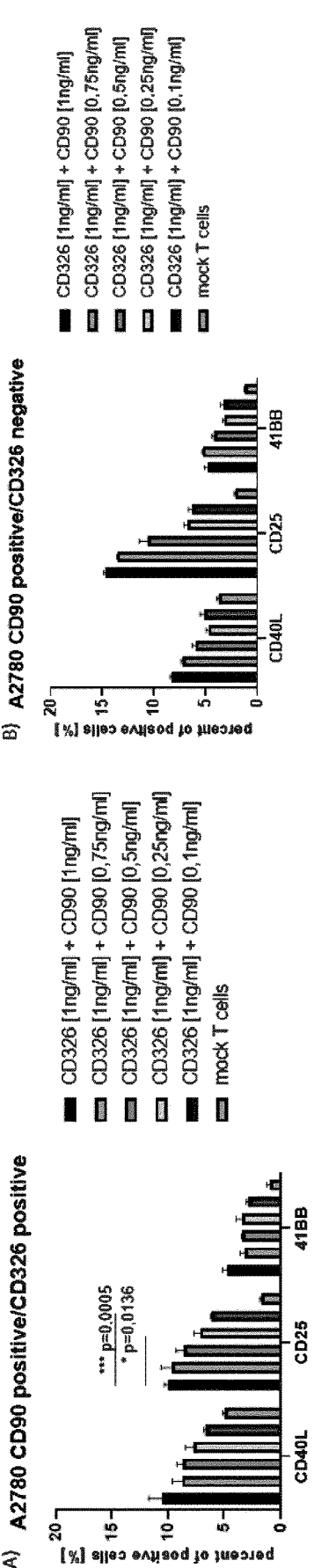
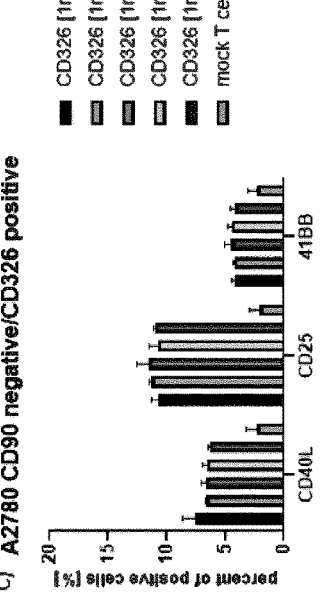
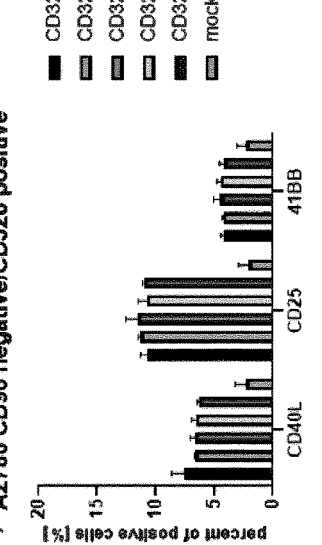
Figure 28 A-C

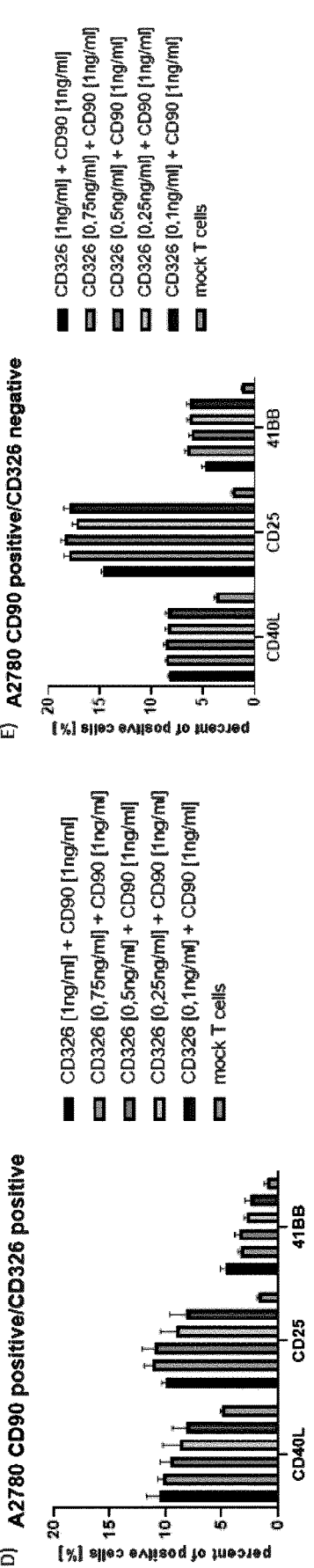
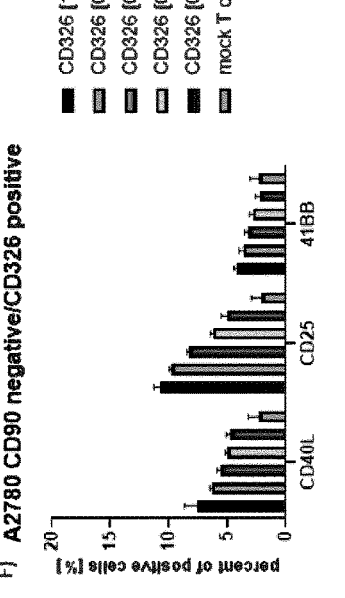
Figure 28 D-F

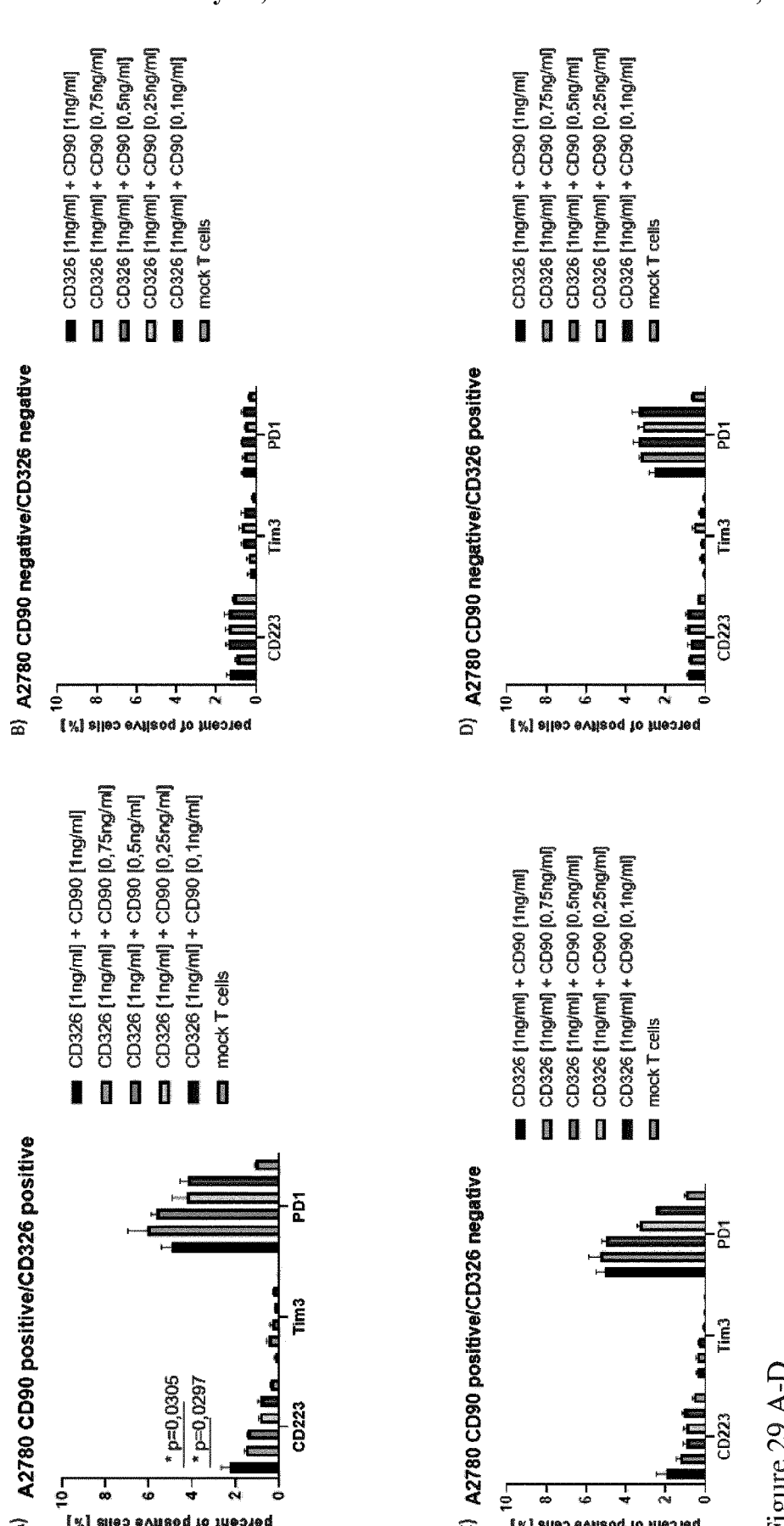
Figure 29 A-D

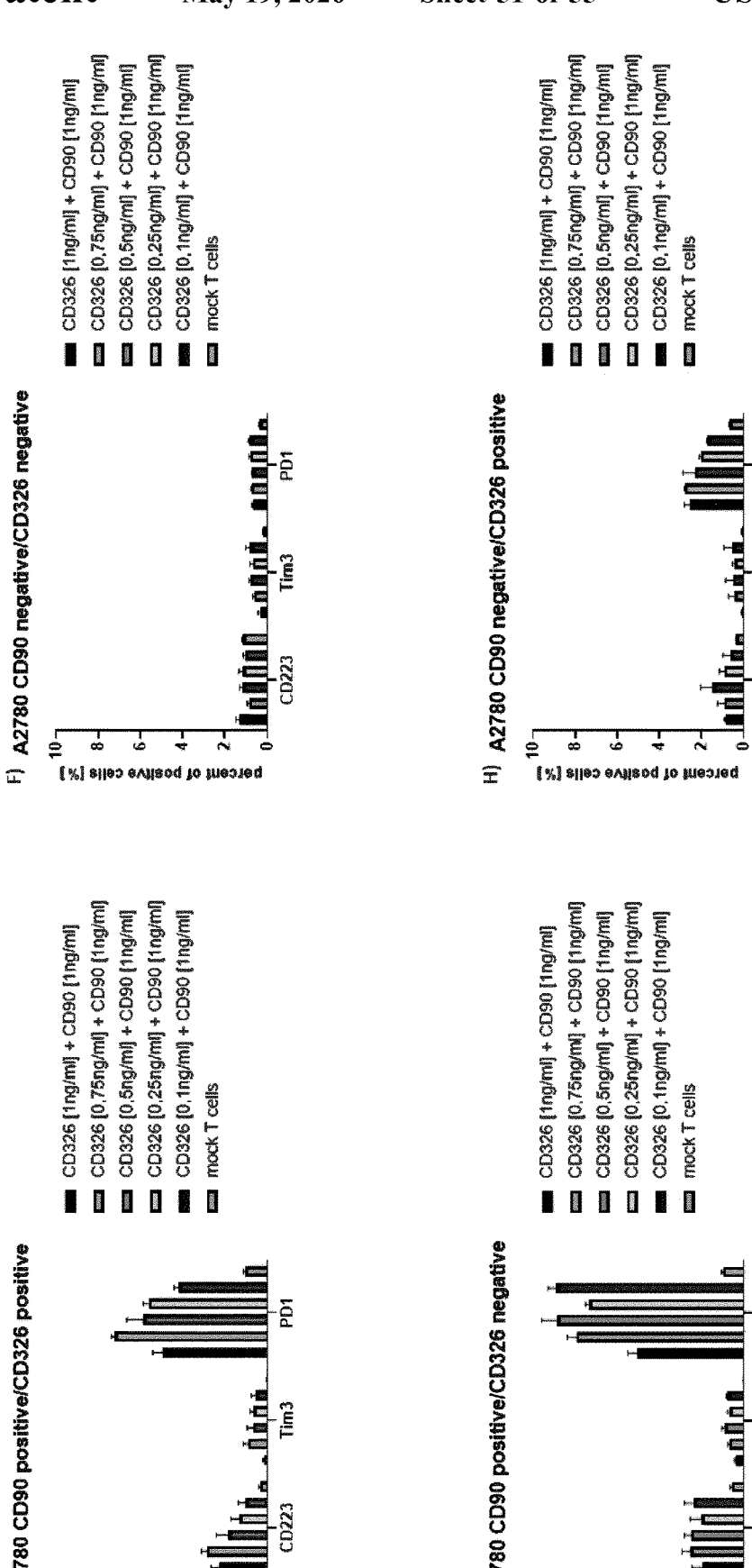
Figure 29 E-H

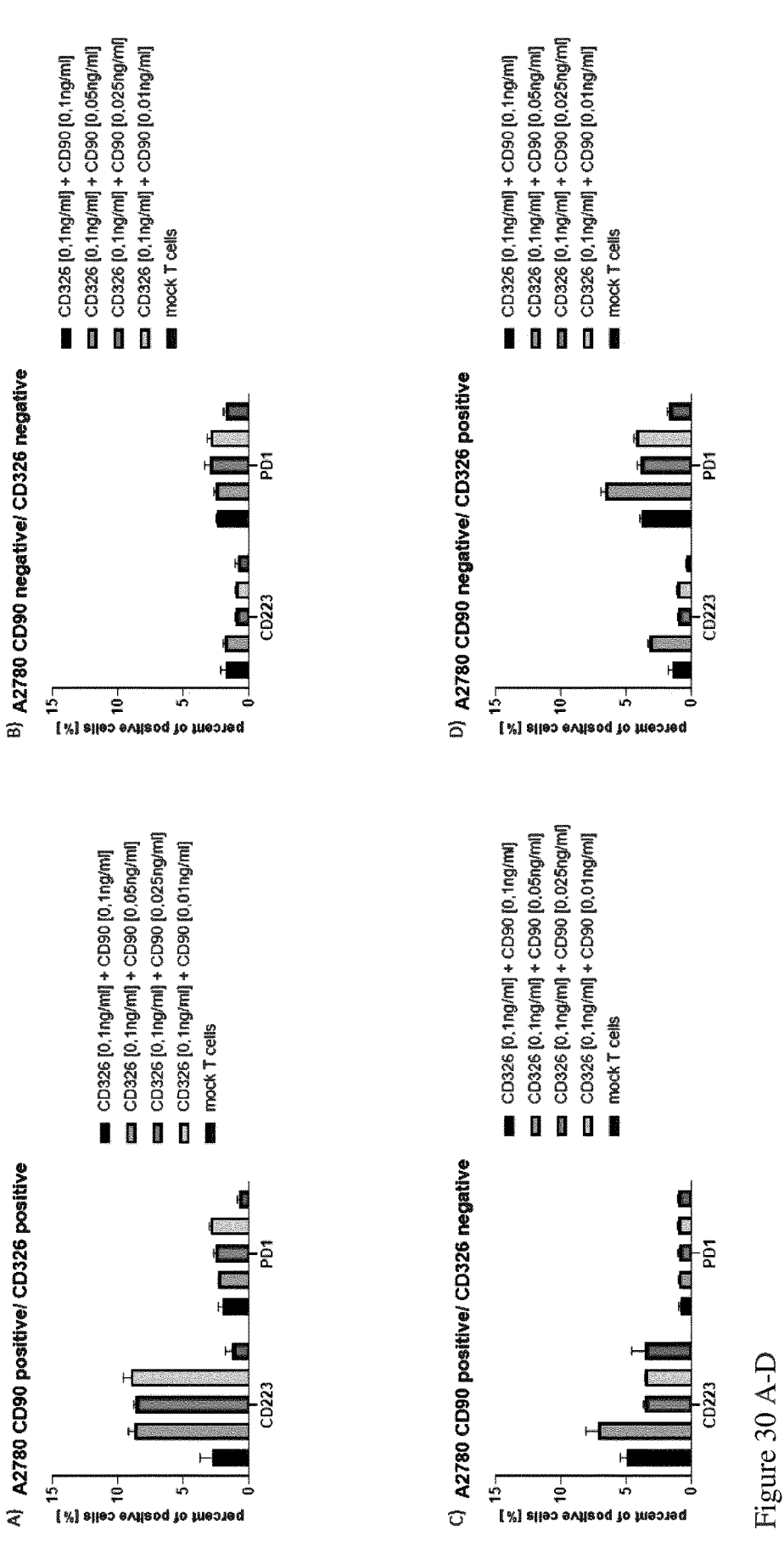
Figure 30 A-D

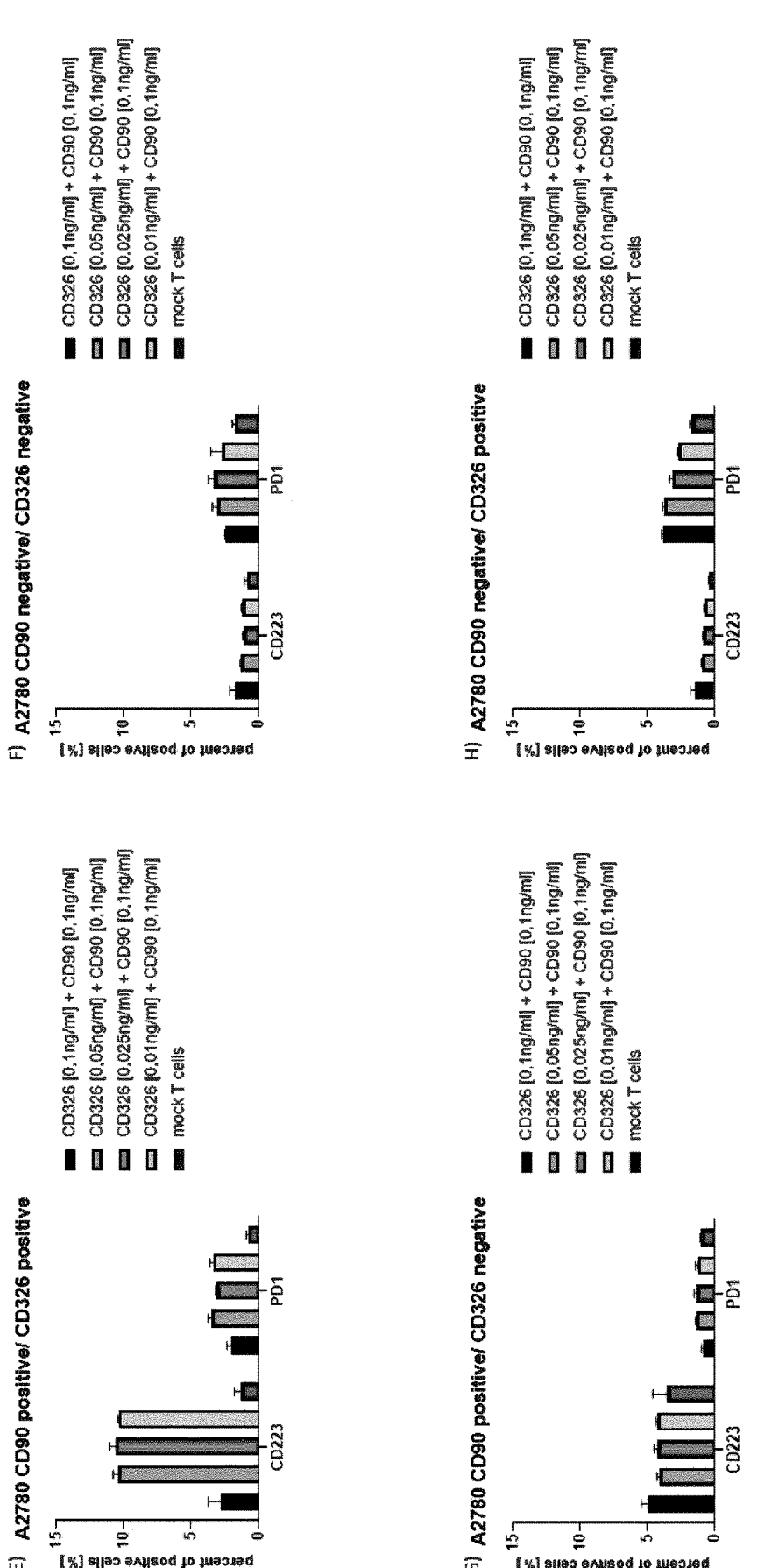
Figure 30 E-H

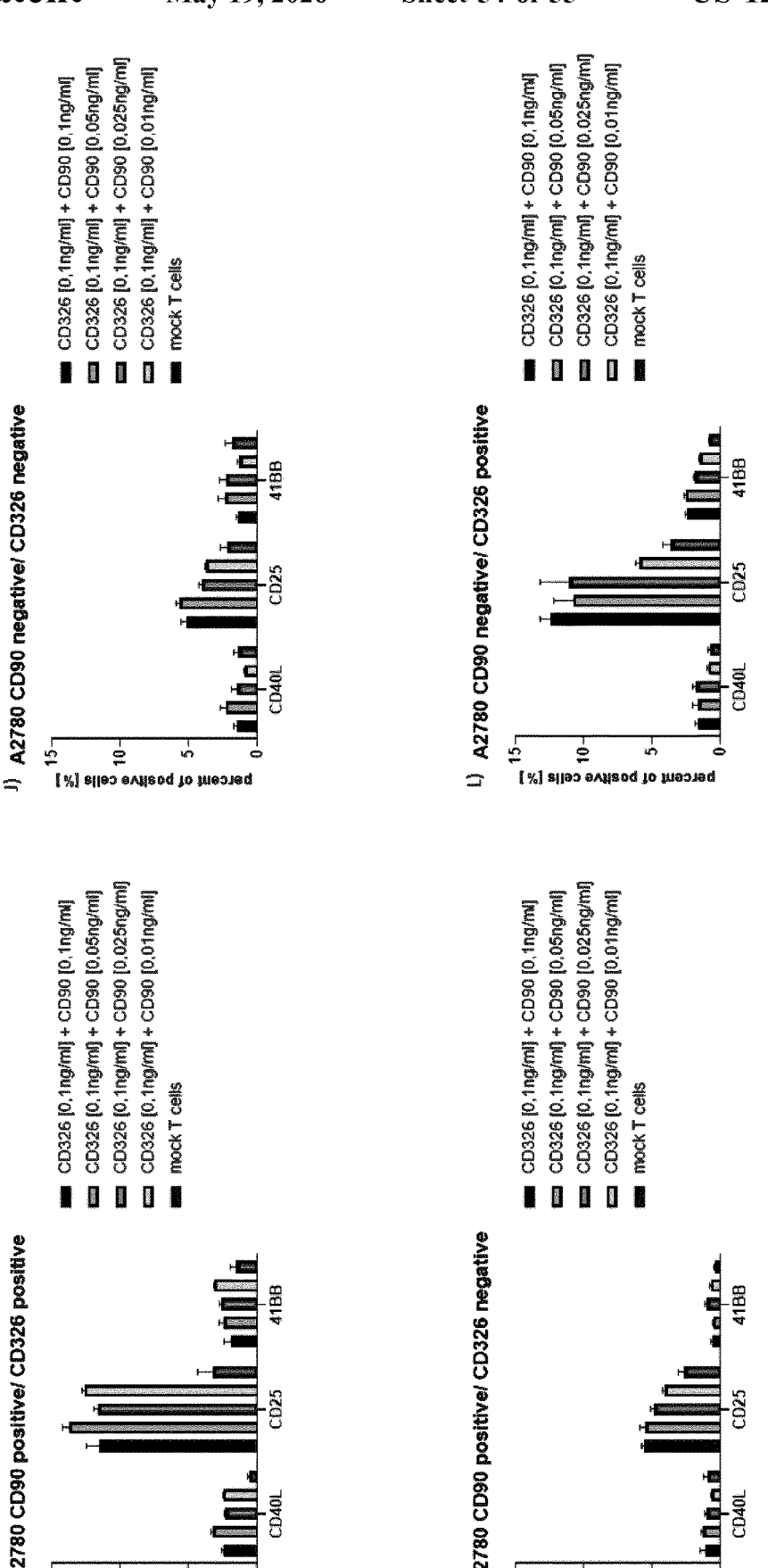
Figure 30 I-L

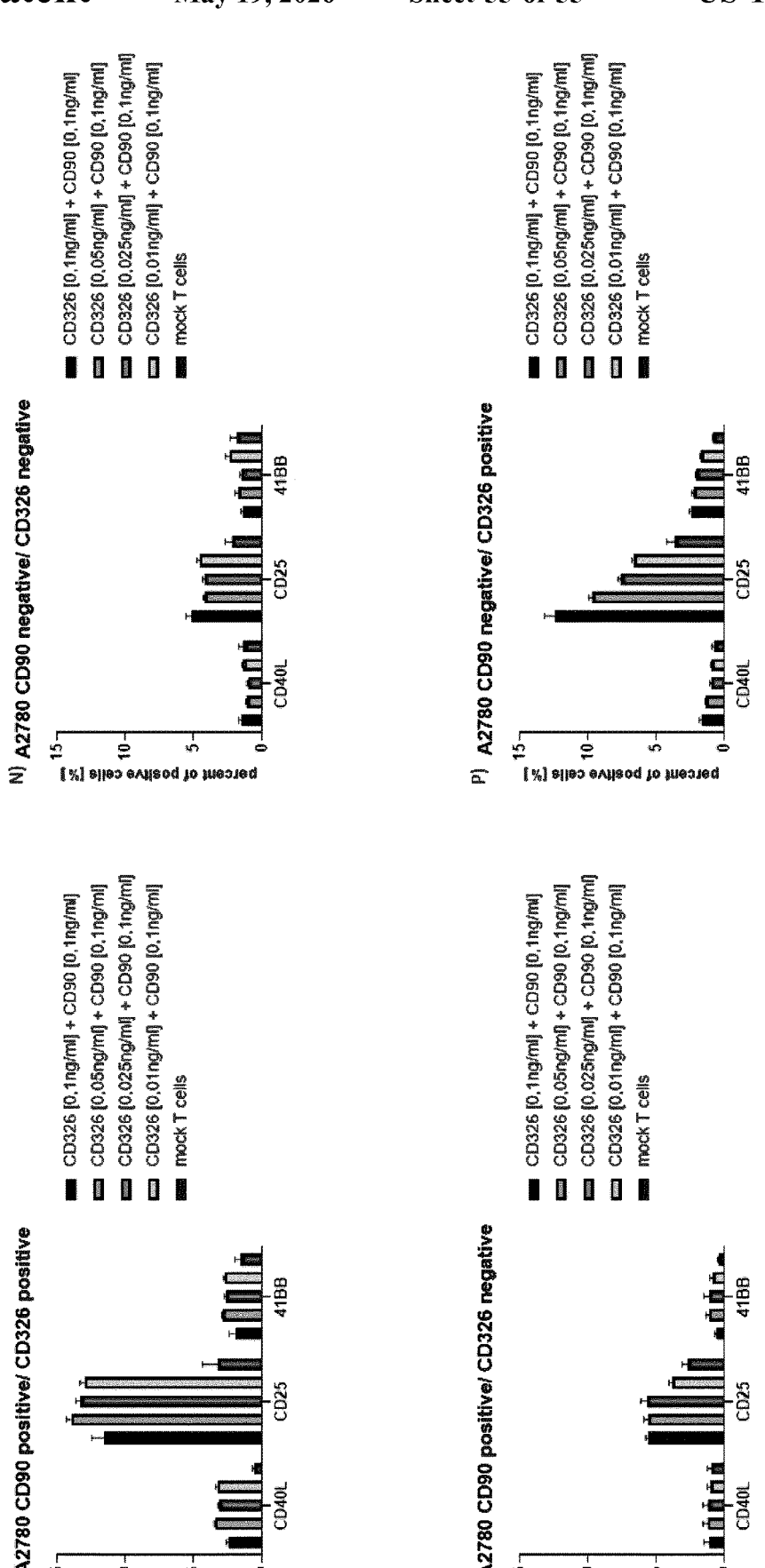
Figure 30 M-P

SEQUENCE LISTING

```
<160> NUMBER OF SEQ ID NOS: 4

<210> SEQ ID NO 1
<211> LENGTH: 107
<212> TYPE: PRT
<213> ORGANISM: Artificial sequence
<220> FEATURE:
<223> OTHER INFORMATION: CD90 VL

<400> SEQUENCE: 1

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Phe Lys Leu Leu Ile
        35                  40                  45

Tyr Tyr Thr Ser Arg Leu His Ser Gly Val Pro Ser Arg Phe Ser Gly
    50                  55                  60

Gly Gly Ser Gly Thr Asp Tyr Ser Leu Thr Ile Ser Asn Leu Glu Lys
65                  70                  75                  80

Glu Asp Ile Ala Thr Tyr Phe Cys Gln Gln Gly Asn Thr Leu Pro Arg
                85                  90                  95

Thr Phe Gly Gly Gly Thr Arg Leu Glu Val Lys
            100                 105

<210> SEQ ID NO 2
<211> LENGTH: 120
<212> TYPE: PRT
<213> ORGANISM: Artificial sequence
<220> FEATURE:
<223> OTHER INFORMATION: CD90 VH

<400> SEQUENCE: 2

Gln Val Gln Leu Leu Gln Pro Gly Ala Glu Leu Val Arg Pro Gly Ala
1               5                   10                  15

Ser Val Arg Leu Ser Cys Lys Thr Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Lys Ile Phe Pro Ser Asp Ser His Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ile Ser Pro Thr Ser Glu Asp Ser Ala Val Tyr Tyr Cys
                85                  90                  95
```

Thr Arg Asp Phe Asp Thr Gln Phe Tyr Ala Met Glu Tyr Trp Gly Gln
            100                     105                     110

Gly Thr Ser Val Thr Val Ser Ser
        115                 120

<210> SEQ ID NO 3
<211> LENGTH: 107
<212> TYPE: PRT
<213> ORGANISM: Artificial sequence
<220> FEATURE:
<223> OTHER INFORMATION: CD326 VL

<400> SEQUENCE: 3

Asp Ile Leu Leu Thr Gln Ser Pro Ala Ile Leu Ser Val Ser Pro Gly
1                   5                   10                  15

Glu Arg Val Ser Phe Ser Cys Arg Ala Ser Gln Ser Ile Gly Ile Ser
            20                  25                  30

Leu His Trp Tyr Gln Gln Arg Pro Ser Asp Ser Pro Arg Leu Leu Ile
        35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Ile Trp Pro Thr
                85                  90                  95

Thr Phe Gly Ala Gly Thr Lys Leu Glu Leu Lys
            100                 105

<210> SEQ ID NO 4
<211> LENGTH: 115
<212> TYPE: PRT
<213> ORGANISM: Artificial sequence
<220> FEATURE:
<223> OTHER INFORMATION: CD326 VH

<400> SEQUENCE: 4

Glu Val Lys Leu Leu Glu Ser Gly Gly Gly Leu Val Gln Pro Gly Gly
1                   5                   10                  15

Ser Leu Lys Leu Ser Cys Ala Ala Ser Gly Phe Asp Phe Ser Arg Phe
            20                  25                  30

Trp Met Thr Trp Val Arg Gln Ala Pro Gly Lys Gly Leu Glu Trp Ile
        35                  40                  45

Gly Glu Ile Asn Leu Asp Ser Ser Thr Ile Asn Tyr Thr Pro Ser Leu
        50                  55                  60

Lys Asp Lys Phe Ile Ile Ser Arg Asp Asn Ala Lys Asn Thr Leu Phe
65                  70                  75                  80

Leu Gln Met Ser Lys Val Arg Ser Glu Asp Thr Ala Leu Tyr Tyr Cys
                85                  90                  95

Ser Arg Gly Ile Ser Met Asp Tyr Trp Gly Gln Gly Thr Ser Val Thr
            100                 105                 110

Val Ser Ser
        115

43

44

COMPOSITIONS AND METHODS FOR TREATING CANCER EXPRESSING CD90 AND CD326

CLAIM OF PRIORITY

This application is the national stage entry of International Patent Application No. PCT/EP2021/063306, filed on May 19, 2021, and claims priority to Application No. EP 20175589.9, filed on May 20, 2020, the disclosures of which are incorporated herein by reference.

SEQUENCE LISTING

This application contains a Sequence Listing that has been submitted electronically as an ASCII text file named "42449-0090US1_SL_ST25.txt." The ASCII text file, created on Nov. 15, 2022, is 4,576 bytes in size. The material in the ASCII text file is hereby incorporated by reference in its entirety.

FIELD OF INVENTION

The present invention relates to the field of treating human cancer comprising cancerous cells co-expressing CD90 and CD326, in particular human ovarian cancer, preferentially the treatment is by adoptive cell therapy, wherein genetically engineered immune cells express at least one chimeric antigen receptor (CAR) that allows to address the cancerous cells co-expressing CD90 and CD326.

BACKGROUND OF THE INVENTION

Cancer is a broad group of diseases involving unregulated cell growth. Cancerous cells divide and grow uncontrollably, forming malignant tumors, and invading nearby parts of the body. The cancer may also spread to more distant parts of the body through the lymphatic system or bloodstream.

Whereas good treatment options are available for some cancer types, others still represent unmet medical needs. In particular, ovarian cancer is a malignancy with limited therapeutic options. One of the most critical aspects of ovarian cancer is the late diagnosis of the disease which is associated with poor five years survival rates (Matulonis, et al., 2016). Currently the main therapeutic options for ovarian cancer patients are surgery and chemotherapy with severe side effects and a high probability of recurrence accompanied by frequent platinum-resistance which decreases the therapeutic options and, thus, overall patient survival.

Thus, the identification of new molecular targets for cancer and ovarian cancer in particular are urgently required. And—consequently—targeting new targets in neoplastic diseases has the same importance. CAR T cells have been shown to have the capability to efficiently target various cancerous targets. By introducing a CAR, T cells would be generated which are tailored to recognize tumor cells as "non-self cells" and therefore help the immune system to eradicate tumor cells. For example, CAR T cells may contact a surface molecule of the target cell which then triggers the activation of the CAR T cell and leads to the lysis of the target cell. CARs are composed for example of the following elements: a single chain fragment variable (scFv) derived from an antibody specific for a particular epitope, i.e. a tumor associated antigen (TAA). The scFv is linked via hinge and transmembrane domains to cytoplasmic signaling domains of T cell. These activation moieties include a T cell costimulatory domain followed by a T cell activating moiety. The CAR-mediated adoptive immunotherapy allows CAR-grafted cells to recognize the TAAs on tumor cells in a HLA-independent manner. However, a single antigen is not sufficient to differentiate tumor cells from non-cancerous cells in a very specific manner. The use of CAR T cells is thus associated with on-target, off-tumor toxicity.

On the one hand this toxicity can be observed in hematological cancer, e.g. targeting CD20 to treat B-cell lymphomas with Rituximab, the normal B-cell compartment is depleted, and targeting CD33 to treat acute myeloid leukaemia, the myeloid compartment is decreasing.

On the other hand solid tumors showed similar "on-target off-tumor" toxicity. For instance, targeting ERBB2 positive tumors caused the death of a patient due to ERBB2 expression on multiple healthy tissues including heart and lung. Furthermore, a CAR therapy to treat renal cell carcinoma targeting carboxy anyhydrase-IX caused liver toxicity. This finding is considered to be related to the specific attack of CAR T cells on bile duct epithelial cells (Lamers, et al., 2013).

To address the problem of "on-target, off-tumor" toxicity, CAR T cells have been designed to increase specificity by dual antigen targeting. The dual-targeting approach is based on the detection of more than one target on a single cancer cell. A distinct group of cell surface antigens was identified which are expressed on human cancer cells, but not or to a lower level on non-malignant cells. These antigens (also referred to as "markers") can be used to identify and/or mark and/or destroy and/or disable escape mechanisms of such cancer cells via ligands that specifically bind to the markers.

Improved specificity can be achieved by employing dual AND CAR T-cells targeting two targets at the same time. Both targets have to be expressed on the tumor at the same time. One CAR delivers the activating signal (signal1), which—on its own—is insufficient to overcome the activation threshold of the CAR T cell. Additionally, the second CAR carries a costimulatory domain (signal2) that—only in combination with the first CAR—synergizes with the first CAR to overcome the activation threshold to fully activate the T cell (Zhao, Song, & Liu, 2019) (Lanitis, et al., 2013).

There is a need in the art for a combination of tumor associated antigens (makers) that e.g. reduces the on-target, off-tumor toxicity, when e.g. treating human ovarian cancer with immunotherapy such as adoptive immune cell therapy.

SUMMARY OF THE INVENTION

The identification of a novel combination of tumor associated antigens to improve immunotherapy was performed on primary human ovarian cancer cells.

Thereby we surprisingly identified the target pair (or the combination) CD90/CD326 being co-expressed in a subset of ovarian cancer patients. Additionally, we evaluated the co-expression of these markers on several healthy human tissues showing that the markers were not expressed on the same cells. These two marker characteristics, i.e. (1) co-expression on tumor cells and (2) lack of (co-)expression on healthy/non-malignant cells or at least to a significant lower level, suggest that the markers we found are good candidates for treatment of these cancers by using immunotherapy such as antibody immunotherapy or adoptive cell immunotherapy using e.g. dual AND CAR or adapter surface activation matrix (SAM) CAR approaches.

The SAM CAR approach, i.e. the combination of one anti-tag CAR in an immune cells such as a T cell and at least two adapters (two tagged polypeptides) specifically binding to different tumor associated antigens (TAA), respectively, herein CD90 and CD326, leads to the benefit that lower concentration of adapters can be applied to a subject in need thereof and nevertheless the immune cell harboring the adapterCAR can be activated properly. This leads to the following benefits:

1. More specificity when two (or more) TAAs are used in an immunotherapy using a CAR immune cells, i.e. a safer approach compared to a single target antigen approach
2. More effective treatment and longer effect of the cancer by preventing the escape mechanism of tumor cells during immunotherapy.
3. Lower dose of each adapter in a subject to be treated possible as only the presence of both adapters is above the threshold value for activating the immune cell harboring the adapterCAR. This spares the healthy cells of the subject to be treated that have only one of both target antigens on their cell surface. The lower the dose of a specific adapter the lower the side effects on healthy cells expressing one of these target antigens, but not both.

It was surprisingly found that the marker combination CD90/CD326 for this SAM CAR approach is well suited. It could be shown that the distribution of these two markers is suited for use in a SAM CAR or AND CAR approach as few healthy cells of a human express both markers expressed but at lower levels compared to cancer cells. It could be shown in vitro that the concentrations of the adapters, i.e. the tagged polypeptides specific for CD90 and CD326, respectively, can be surprisingly low individually but trigger the CAR immune cell in the sum of both concentrations (e.g. in SAM CAR: 0.1 ng/ml anti-CD90 antibody as adapter and 0.1 ng/ml anti-CD326 adapter (FIG. 5B) compared to "single CAR/adapter constellation": 1000 ng/ml anti-CD90 antibody as single adapter (FIG. 4A) and 10 ng/ml anti-CD326 antibody as single adapter (FIG. 4B)).

Therefore, the present invention provides a combination of an antigen binding domain specific for CD90 and an antigen binding domain specific for CD326 for use in treatment of cancer that co-expresses CD90 and CD326. Herein, also provided are immune cells that express in AND CAR constellation the CD90CAR and CD326CAR, diverse compositions involving adapterCAR/adapter constellations with regard to the specificity for CD90 and CD326.

4 tumor1, B) Region of interest CD90 and CD326 co-expressing tumor 2, C) Region of interest CD90 and CD326 co-expressing tumor3. In the merged images CD326 is shown in red, and CD90 is shown in green, respectively.

Figure 3:
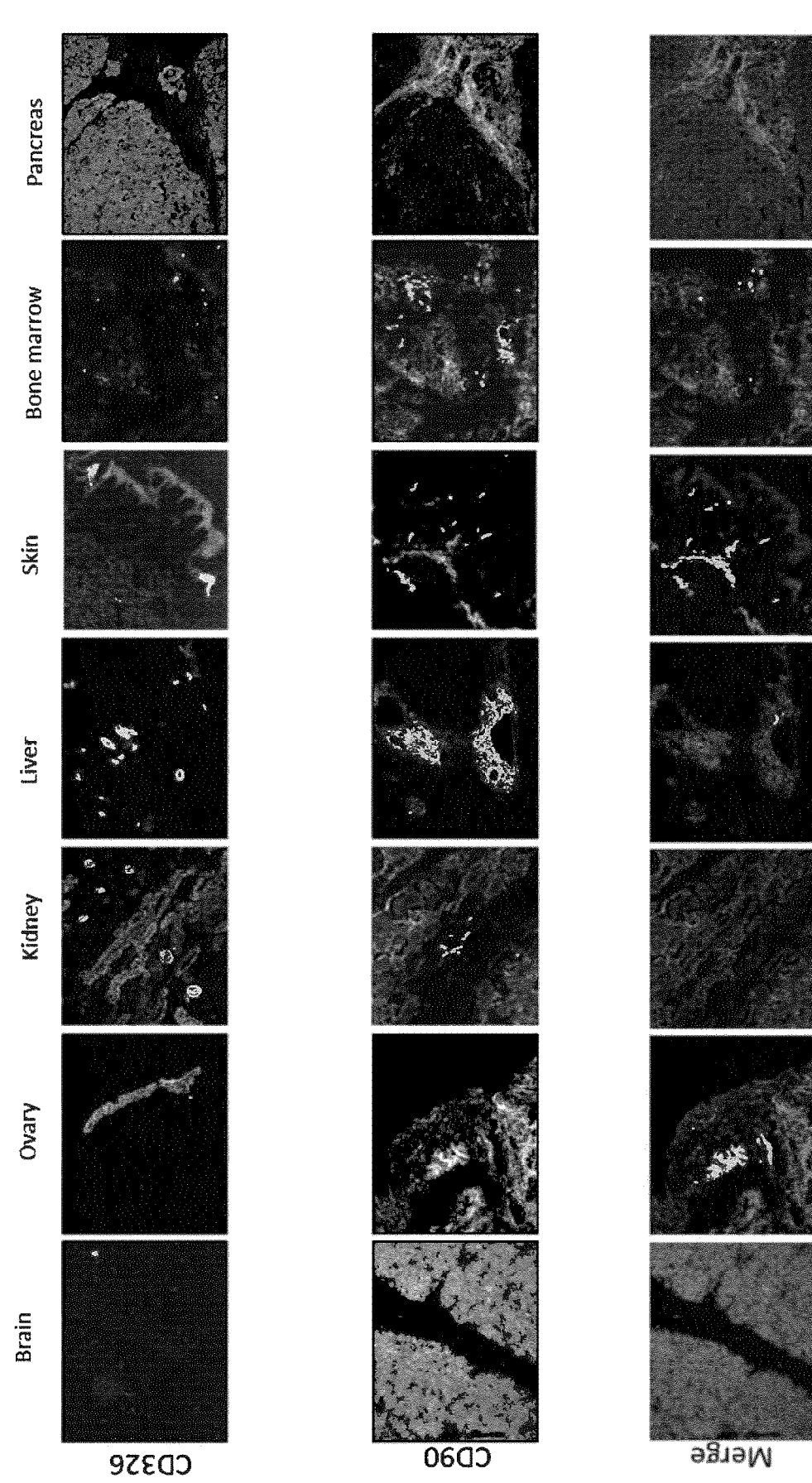

FIG. 3 Healthy tissues do not co-express CD90 and CD326

Fresh-frozen human healthy tissues were sliced and fixed with acetone. The subsequent screening was performed on the MACSima™ ultra-high-content imaging platform by employing a sequential staining of antibodies. In the merged images CD326 is shown in red, and CD90 is shown in green, respectively.

Figure 4:
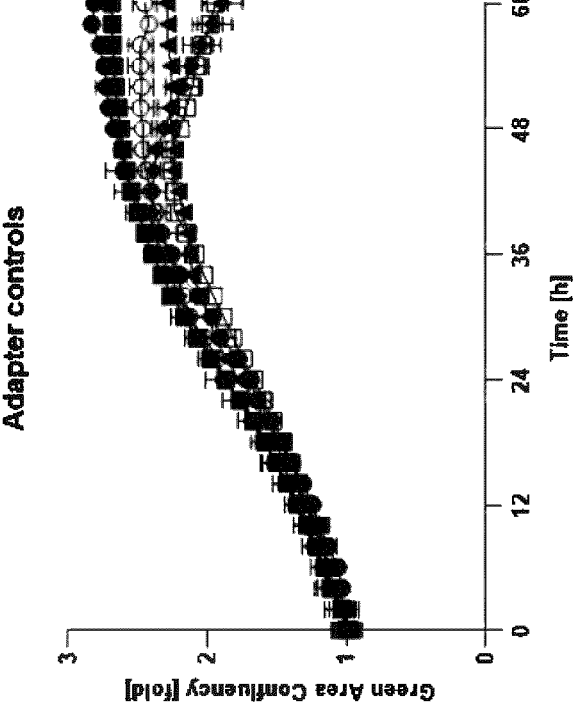

FIG. 4 Adapter CAR T cells targeting CD90 and CD326 are cytolytically active against ovarian cancer cell line co-expressing CD90 and CD326

Primary human T cells were isolated and transduced with the indicated CAR construct against biotin. Anti-biotin CAR T cells were co-cultured with CD90–, CD326–, and GFP-expressing target cells (ovarian cancer cell line A2780) for 72 h in the presence of varying doses of biotinylated CD90 (A) or biotinylated CD326 (B) antibodies, respectively. Non-binding antibodies do not induce target cell lysis and the presence of adapter CARs is essential for target cell lysis (C). GFP-fluorescence was measured over time. CAR T cell mediated lysis of target cells results in decreased GFP-fluorescence.

Figure 5:
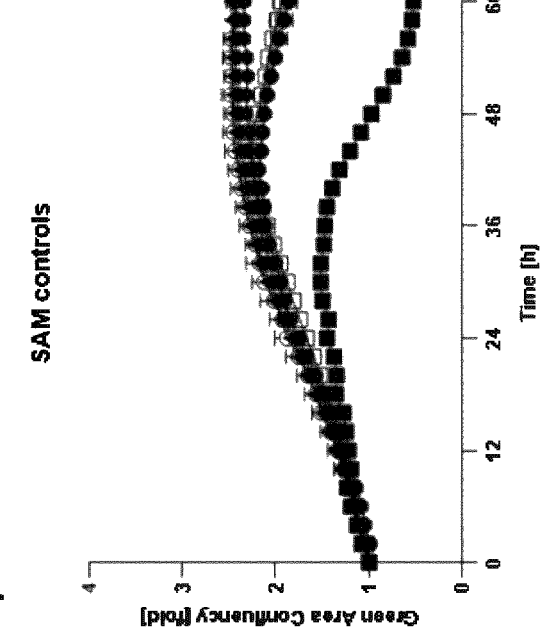

FIG. 5 Adapter CAR T cells co-targeting CD90 and CD326 are cytolytically active at lower doses of adapter against ovarian cancer cell line co-expressing CD90 and CD326

Primary human T cells were isolated and transduced with the indicated CAR constructs against biotin. Anti-biotin CAR T cells were co-cultured with CD90–, CD326–, and GFP-expressing target cells (ovarian cancer cell line A2780) for 72 h in the presence of biotinylated CD90 and biotinylated CD326 antibodies (A), respectively. (B) The same as in (A) but reduced to strongest synergistic dosing. Non-binding antibodies do not induce target cell lysis and the presence of adapter CARs is essential for target cell lysis (C). GFP-fluorescence was measured over time. CAR T cell mediated lysis of target cells results in decreased GFP-fluorescence.

FIG. 6 Transgenic target cell lines differentially express CD90 and CD326

Ovarian cancer cell line A2780 was genetically modified to be deficient for CD90 and CD326 (A), to express CD326 and CD90 (B), to be single positive for CD90 (C), or to be single positive for CD326(D).

FIG. 7 Co-targeting CD90 and CD326 with Adapter CAR T cells is impaired in ovarian cancer cells expressing CD326 but lack CD90

Primary human T cells were isolated and transduced with a CAR constructs against biotin. Anti-biotin CAR T cells were co-cultured with CD326– and GFP-expressing target cells (ovarian cancer cell line A2780 lacking CD90) for 72 h in the presence of biotinylated CD90 (A) or biotinylated CD326 antibodies (B), respectively. Co-cultures of anti-biotin CAR T cells with CD326– and GFP-expressing target cells (ovarian cancer cell line A2780 lacking CD90) for 72 h in the presence of biotinylated CD90 and CD326 antibodies (C). GFP-fluorescence was measured over time. CAR T cell mediated lysis of target cells results in decreased GFP-fluorescence.

Figure 8:
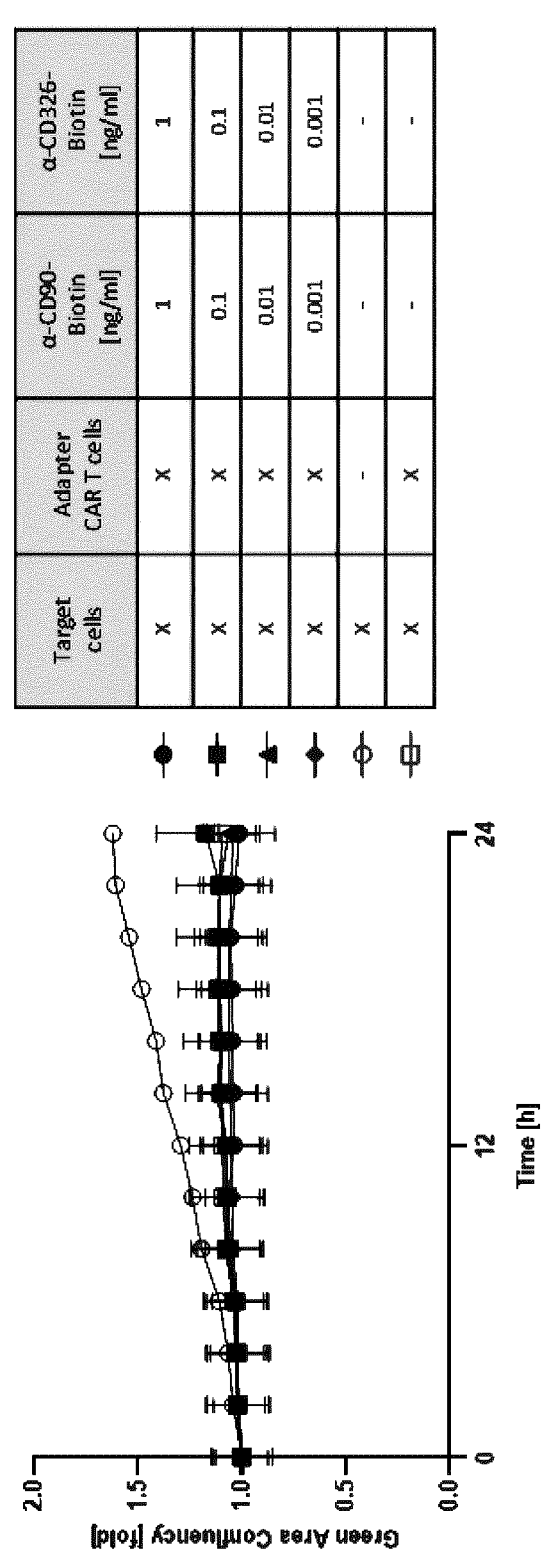

FIG. 8 Co-targeting CD90 and CD326 with Adapter CAR T cells is impaired in ovarian cancer cells expressing CD90 but lack CD326

Primary human T cells were isolated and transduced with a CAR constructs against biotin. Anti-biotin CAR T cells were co-cultured with CD90– and GFP-expressing target cells (ovarian cancer cell line A2780 lacking CD326) for 72 h in the presence of biotinylated CD90 (A) or biotinylated CD326 antibodies (B), respectively. Co-cultures of anti-biotin CAR T cells with CD90– and GFP-expressing target cells (ovarian cancer cell line A2780 lacking CD326) for 72 h in the presence of biotinylated CD90 and CD326 antibodies (C). GFP-fluorescence was measured over time. CAR T cell mediated lysis of target cells results in decreased GFP-fluorescence.

FIG. 9 Co-targeting CD90 and CD326 with Adapter CAR T cells is impaired in ovarian cancer cells lacking CD90 and CD326

Primary human T cells were isolated and transduced with a CAR constructs against biotin. Anti-biotin CAR T cells were co-cultured with GFP-expressing target cells (ovarian cancer cell line A2780 lacking CD90 and CD326) for 72 h in the presence of biotinylated CD90 (A) or biotinylated CD326 antibodies (B), respectively. Co-cultures of anti-biotin CAR T cells with and GFP-expressing target cells (ovarian cancer cell line A2780 lacking CD90 and CD326) for 72 h in the presence of biotinylated CD90 and CD326 antibodies (C). GFP-fluorescence was measured over time. CAR T cell mediated lysis of target cells results in decreased GFP-fluorescence.

Figure 10:
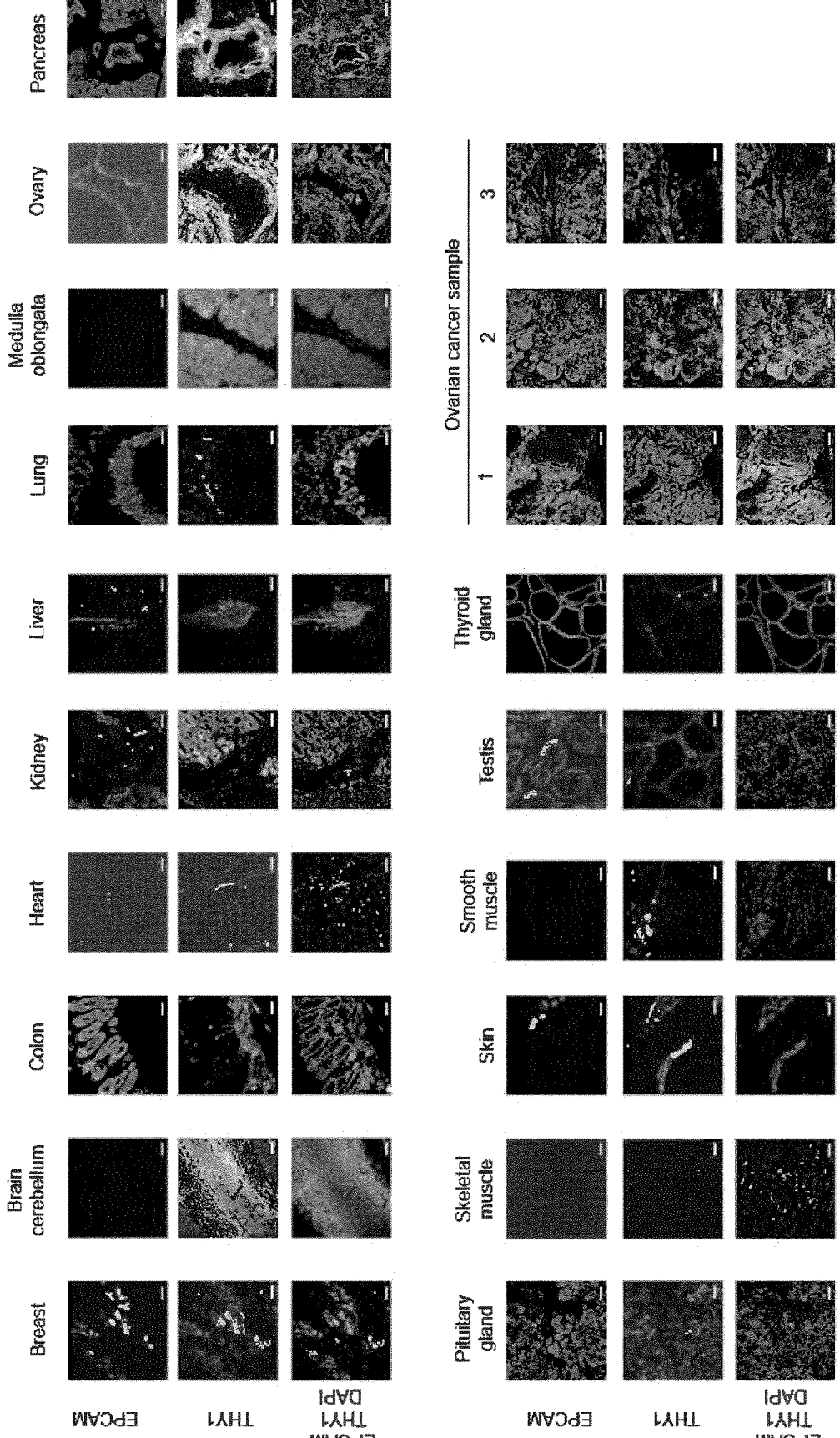

FIG. 10 Microscopic immunofluorescence analysis revealed discrete CD90 and CD326 expression in healthy tissues and co-expression of CD90 and CD326 on a subset of high-grade serous ovarian carcinoma Fresh-frozen human healthy tissues and high-grade serous ovarian carcinoma were sliced and fixed with acetone. The subsequent screening was performed on the MACSima™ ultra-high-content imaging platform by employing a sequential staining of antibodies. Here the two markers of interest CD90 as well as CD326 are shown and analyzed for cellular co-expression. In the merged images CD326 is shown in red, and CD90 is shown in green, respectively. Scale bars represent 100 μm.

FIG. 11 Quantification of CD90 and CD326 expression shows expression of CD90 and CD326 in healthy human tissues and elevated co-expression in high-grade serous ovarian carcinoma All image (16 bits) data sets for each healthy and tumor tissue were imported into QiTissue™ software. The software uses the nuclei and cell membrane markers to perform image segmentation identifying individual cells. As it uses all the cell membrane markers known to the QiTissue™ system simultaneously, it can segment most types of cell in the sample. For each tissue similar segmentation parameters were used. Once the cells are identified, the features like mean fluorescent intensities (MFI) are computed for each cell against the background. These intensities are then used for further downstream processing. During the downstream analysis, all computed MFI are scaled between the range 0 and 1 for visualization and comparability (the original MFI for 16 bit images ranges between 0 and 65535). These values are then compared against each other as shown in the boxplot.

Figure 12:
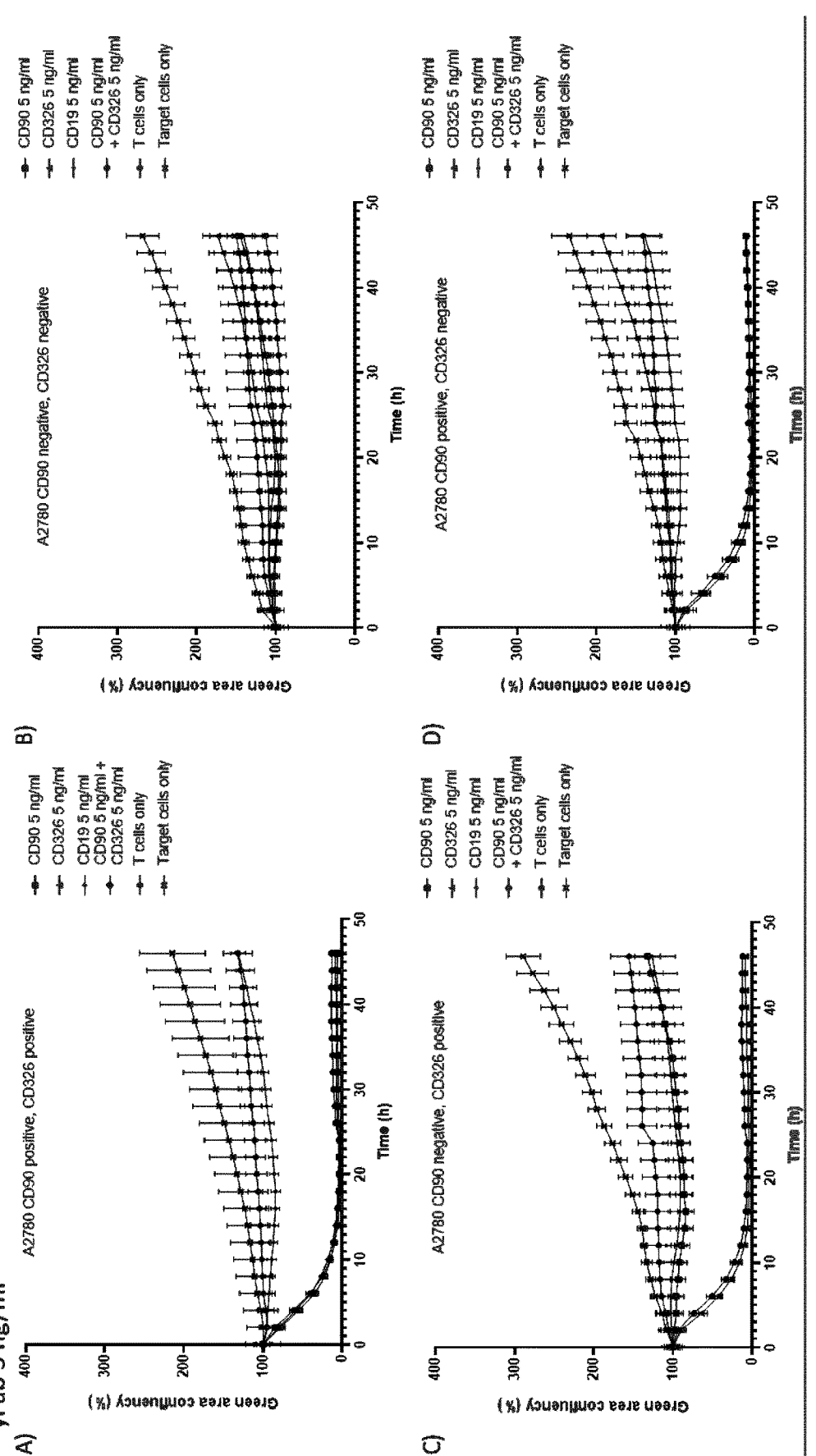

FIG. 12 Adapter CAR T cells targeting CD90 and CD326 at a concentration of 5 ng/ml are cytolytically active against ovarian cancer cell line co-expressing CD90 and CD326 Primary human T cells were isolated and transduced with the indicated CAR construct against biotin. Anti-biotin CAR T cells were co-cultured with CD90+/CD326+ (A), CD90–/CD326– (B), CD90–/CD326+(C) and CD90+/CD326– (D)

expressing target cells ovarian cancer cell line A2780 for 48 h in the presence of monobiotinylated anti-CD90 or mono-biotinylated anti-CD326 FABs, respectively. Non-binding FABs do not induce target cell lysis and the presence of adapter CARs is essential for target cell lysis. All A2780 ovarian cancer cell line expresses GFP. GFP-fluorescence was measured over time. CAR T cell mediated lysis of target cells results in decreased GFP-fluorescence. Statistical analysis included unpaired student's t test.

Figure 13:
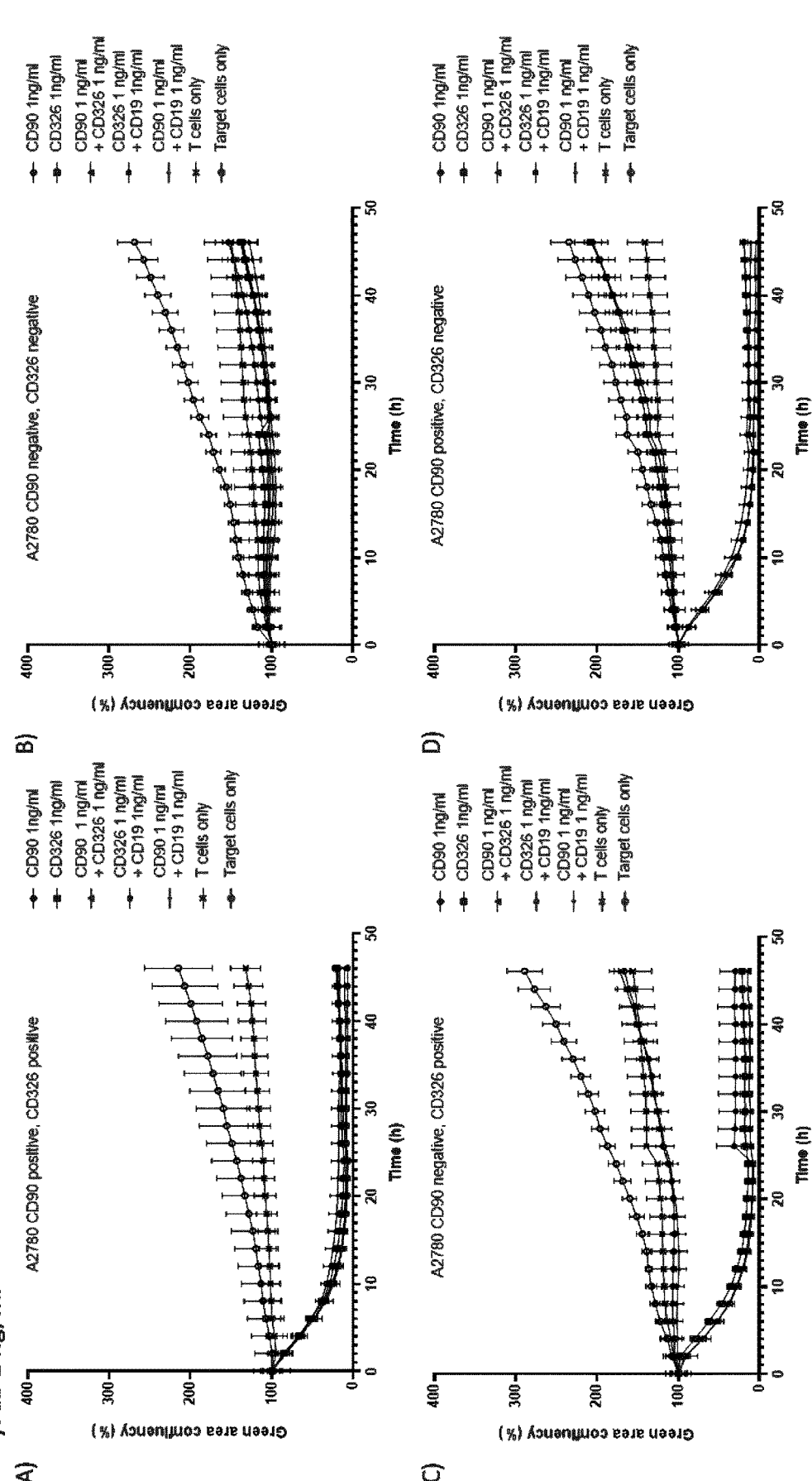

FIG. 13 Adapter CAR T cells targeting CD90 and CD326 at a concentration of 1 ng/ml are cytolytically active against ovarian cancer cell line co-expressing CD90 and CD326 Primary human T cells were isolated and transduced with the indicated CAR construct against biotin. Anti-biotin CAR T cells were co-cultured with CD90+/CD326+ (A), CD90–/CD326– (B), CD90–/CD326+(C) and CD90+/CD326– (D) expressing target cells ovarian cancer cell line A2780 for 48 h in the presence of monobiotinylated anti-CD90 or mono-biotinylated anti-CD326 FABs, respectively. All A2780 ovarian cancer cell line expresses GFP. GFP-fluorescence was measured over time. CAR T cell mediated lysis of target cells results in decreased GFP-fluorescence. Statistical analysis included unpaired student's t test.

Figure 14:
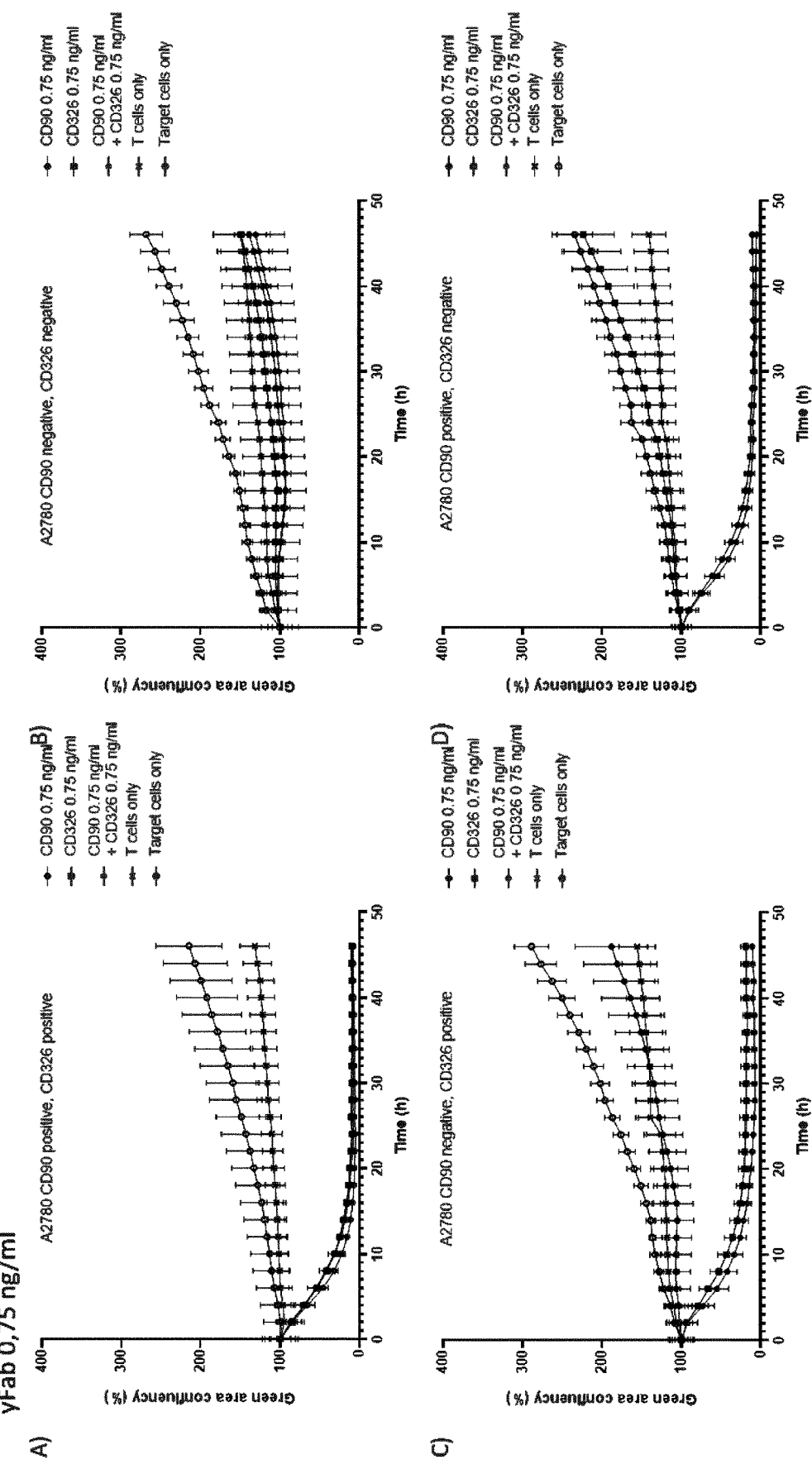

FIG. 14 Adapter CAR T cells targeting CD90 and CD326 at a concentration of 0.75 ng/ml are cytolytically active against ovarian cancer cell line co-expressing CD90 and CD326

Primary human T cells were isolated and transduced with the indicated CAR construct against biotin. Anti-biotin CAR T cells were co-cultured with CD90+/CD326+ (A), CD90–/D326– (B), CD90–/CD326+(C) and CD90+/CD326– (D) expressing target cells ovarian cancer cell line A2780 for 48 h in the presence of monobiotinylated anti-CD90 or mono-biotinylated anti-CD326 FABs, respectively. All A2780 ovarian cancer cell line expresses GFP. GFP-fluorescence was measured over time. CAR T cell mediated lysis of target cells results in decreased GFP-fluorescence. Statistical analysis included unpaired student's t test.

Figure 15:
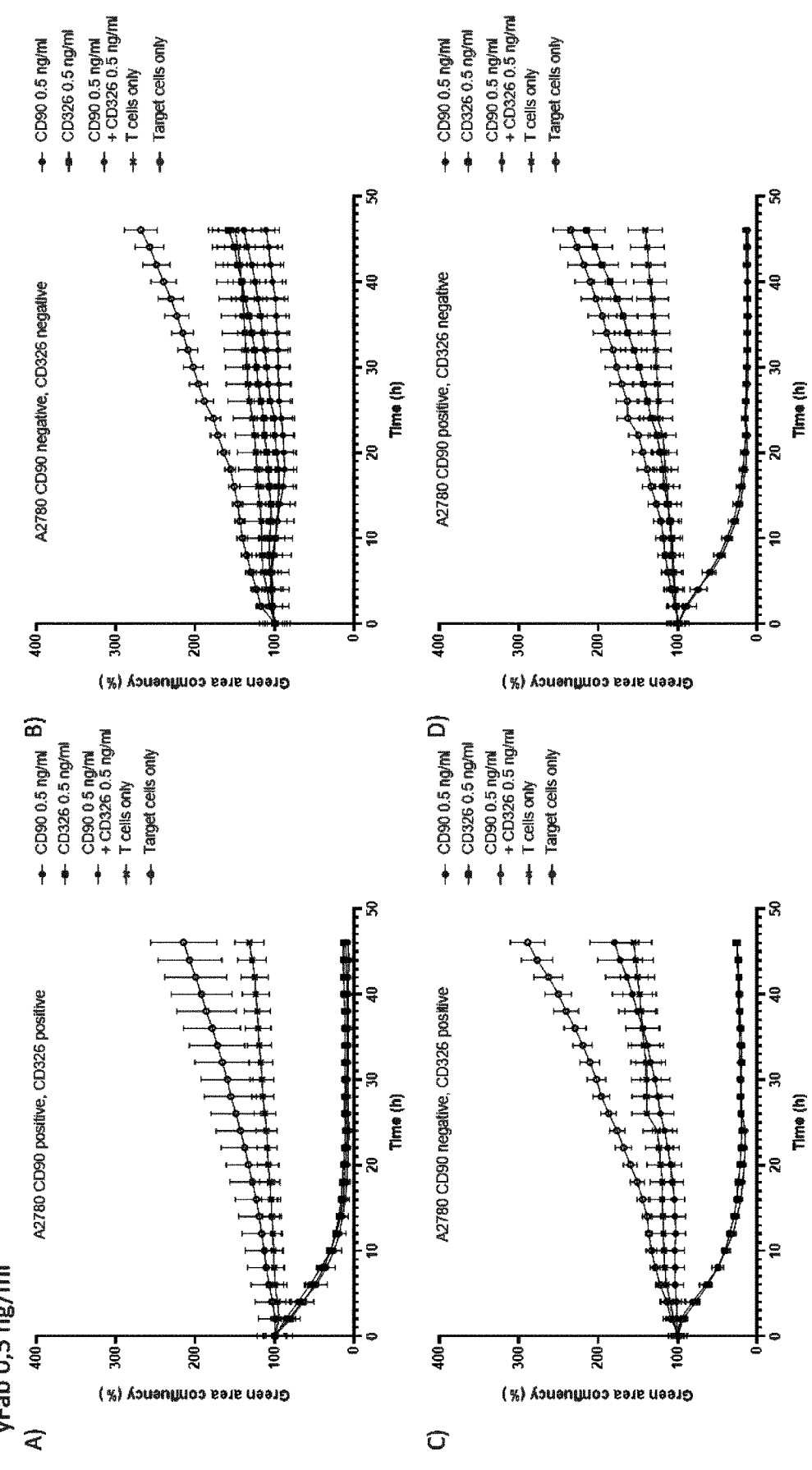

FIG. 15 Adapter CAR T cells targeting CD90 and CD326 at a concentration of 0.5 ng/ml are cytolytically active against ovarian cancer cell line co-expressing CD90 and CD326

Primary human T cells were isolated and transduced with the indicated CAR construct against biotin. Anti-biotin CAR T cells were co-cultured with CD90+/CD326+ (A), CD90–/D326– (B), CD90–/CD326+(C) and CD90+/CD326– (D) expressing target cells ovarian cancer cell line A2780 for 48 h in the presence of monobiotinylated anti-CD90 or mono-biotinylated anti-CD326 FABs, respectively. All A2780 ovarian cancer cell line expresses GFP. GFP-fluorescence was measured over time. CAR T cell mediated lysis of target cells results in decreased GFP-fluorescence. Statistical analysis included unpaired student's t test.

Figure 16:
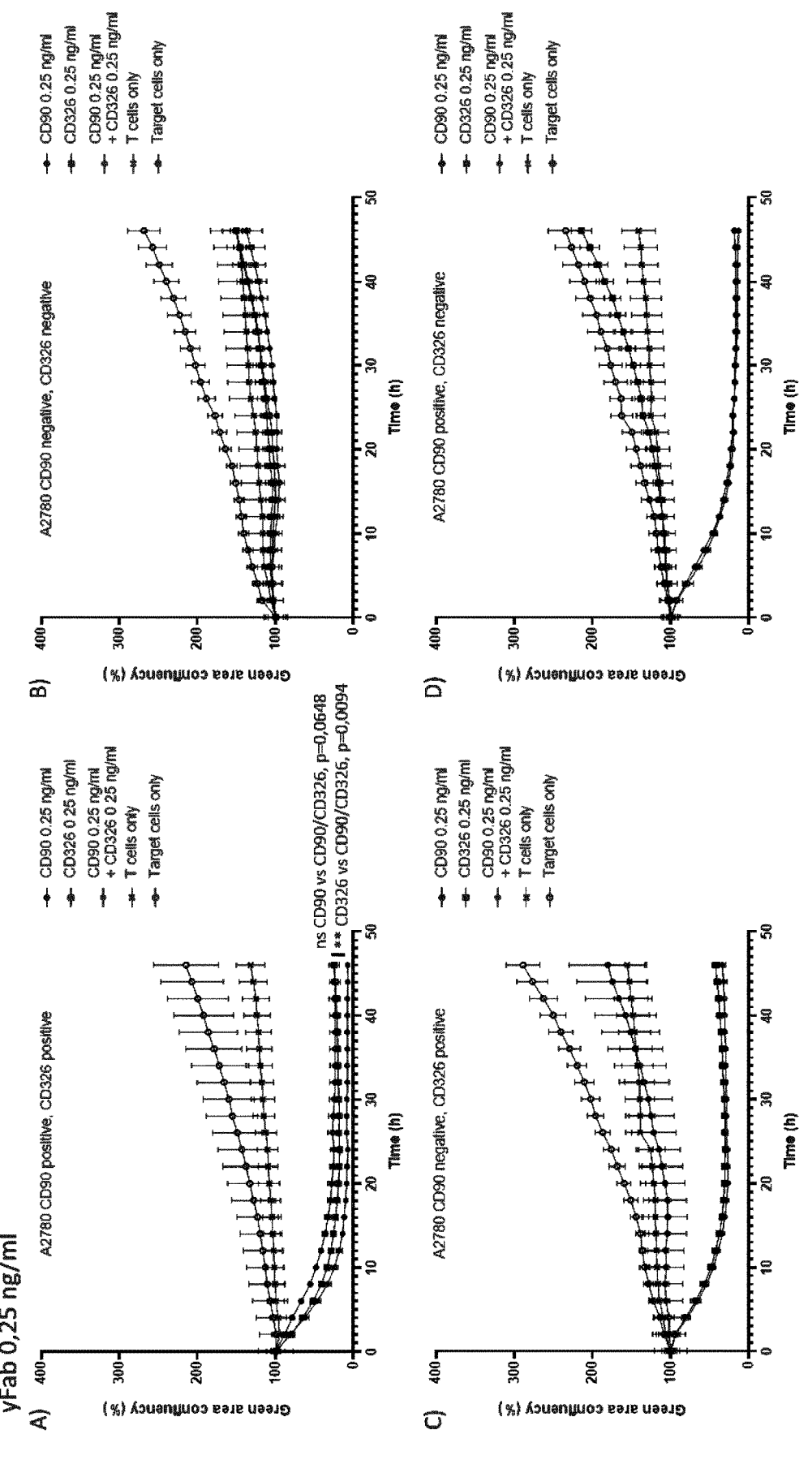

FIG. 16 Adapter CAR T cells targeting CD90 and CD326 at a concentration of 0.25 ng/ml are cytolytically active against ovarian cancer cell line co-expressing CD90 and CD326

Primary human T cells were isolated and transduced with the indicated CAR construct against biotin. Anti-biotin CAR T cells were co-cultured with CD90+/CD326+ (A), CD90–/D326– (B), CD90–/CD326+(C) and CD90+/CD326– (D) expressing target cells ovarian cancer cell line A2780 for 48 h in the presence of monobiotinylated anti-CD90 or mono-biotinylated anti-CD326 FABs, respectively. All A2780 ovarian cancer cell line expresses GFP. GFP-fluorescence was measured over time. CAR T cell mediated lysis of target cells results in decreased GFP-fluorescence. Statistical analysis included unpaired student's t test.

Figure 17:
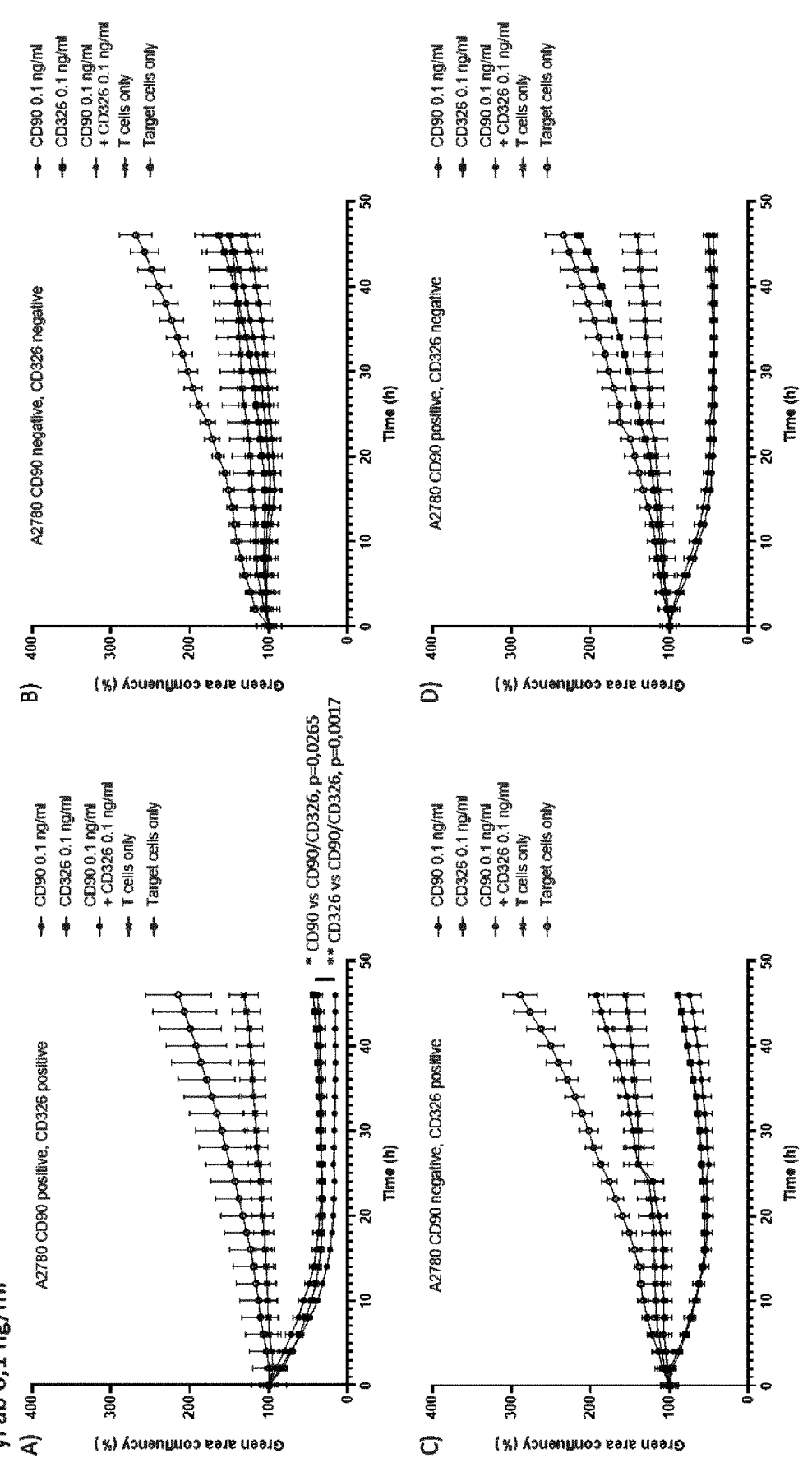

FIG. 17 Adapter CAR T cells targeting CD90 and CD326 at a concentration of 0.1 ng/ml are cytolytically active against ovarian cancer cell line co-expressing CD90 and CD326

Primary human T cells were isolated and transduced with the indicated CAR construct against biotin. Anti-biotin CAR T cells were co-cultured with CD90+/CD326+ (A), CD90−/D326− (B), CD90−/CD326+(C) and CD90+/CD326− (D) expressing target cells ovarian cancer cell line A2780 for 48 h in the presence of monobiotinylated anti-CD90 or mono-biotinylated anti-CD326 FAbs, respectively. All A2780 ovarian cancer cell line expresses GFP. GFP-fluorescence was measured over time. CAR T cell mediated lysis of target cells results in decreased GFP-fluorescence. Statistical analysis included unpaired student's t test.

Figure 18:
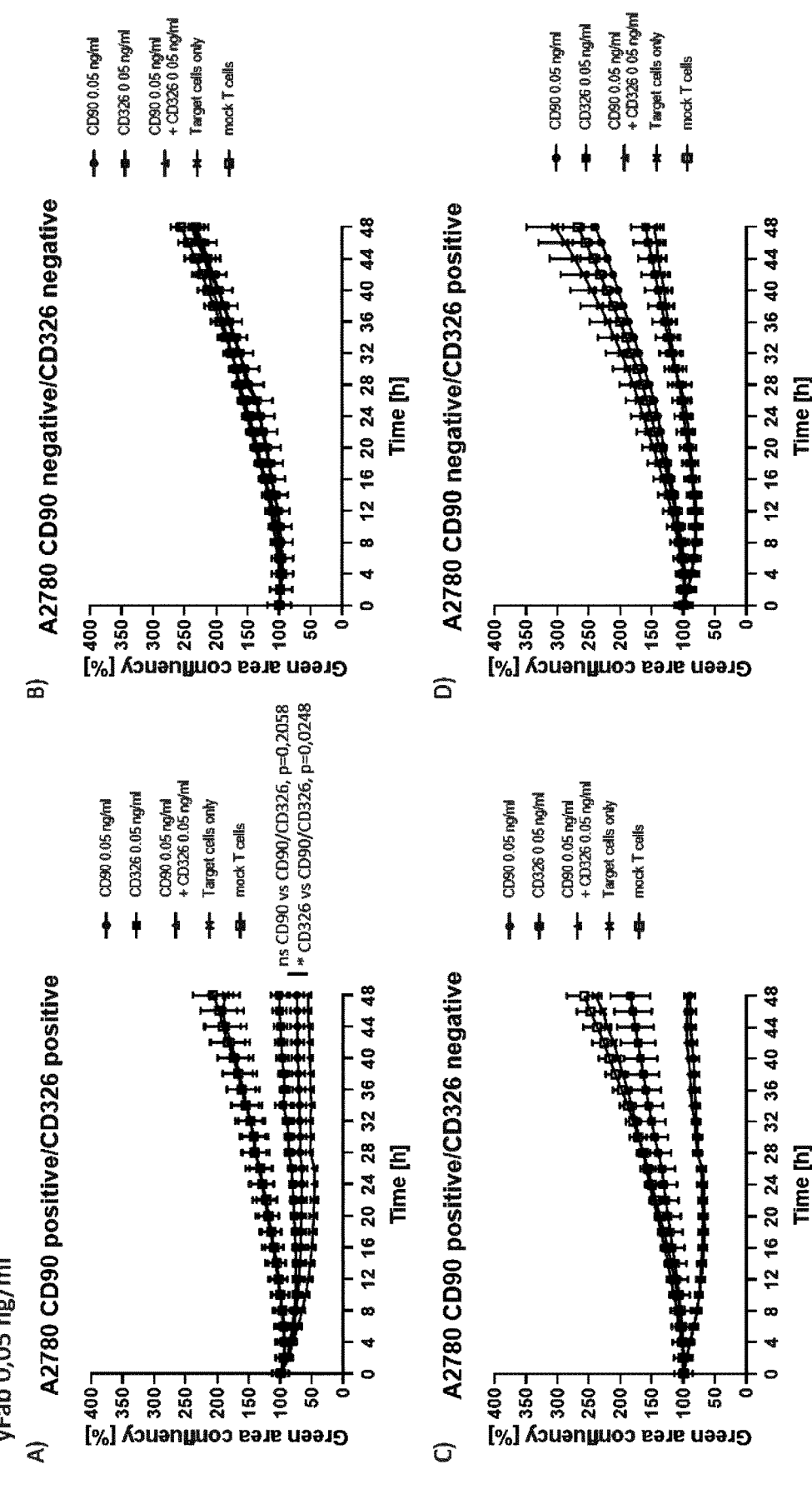

FIG. 18 Adapter CAR T cells targeting CD90 and CD326 at a concentration of 0.05 ng/ml are cytolytically active against ovarian cancer cell line co-expressing CD90 and CD326 Primary human T cells were isolated and transduced with the indicated CAR construct against biotin. Anti-biotin CAR T cells were co-cultured with CD90+/CD326+ (A), CD90−/D326− (B), CD90+/CD326− (C) and CD90−/CD326+ (D) expressing target cells ovarian cancer cell line A2780 for 48 h in the presence of monobiotinylated anti-CD90 or monobiotinylated anti-CD326 FAbs, respectively. All A2780 ovarian cancer cell line expresses GFP. GFP-fluorescence was measured over time. CAR T cell mediated lysis of target cells results in decreased GFP-fluorescence. Statistical analysis included unpaired student's t test.

Figure 19:
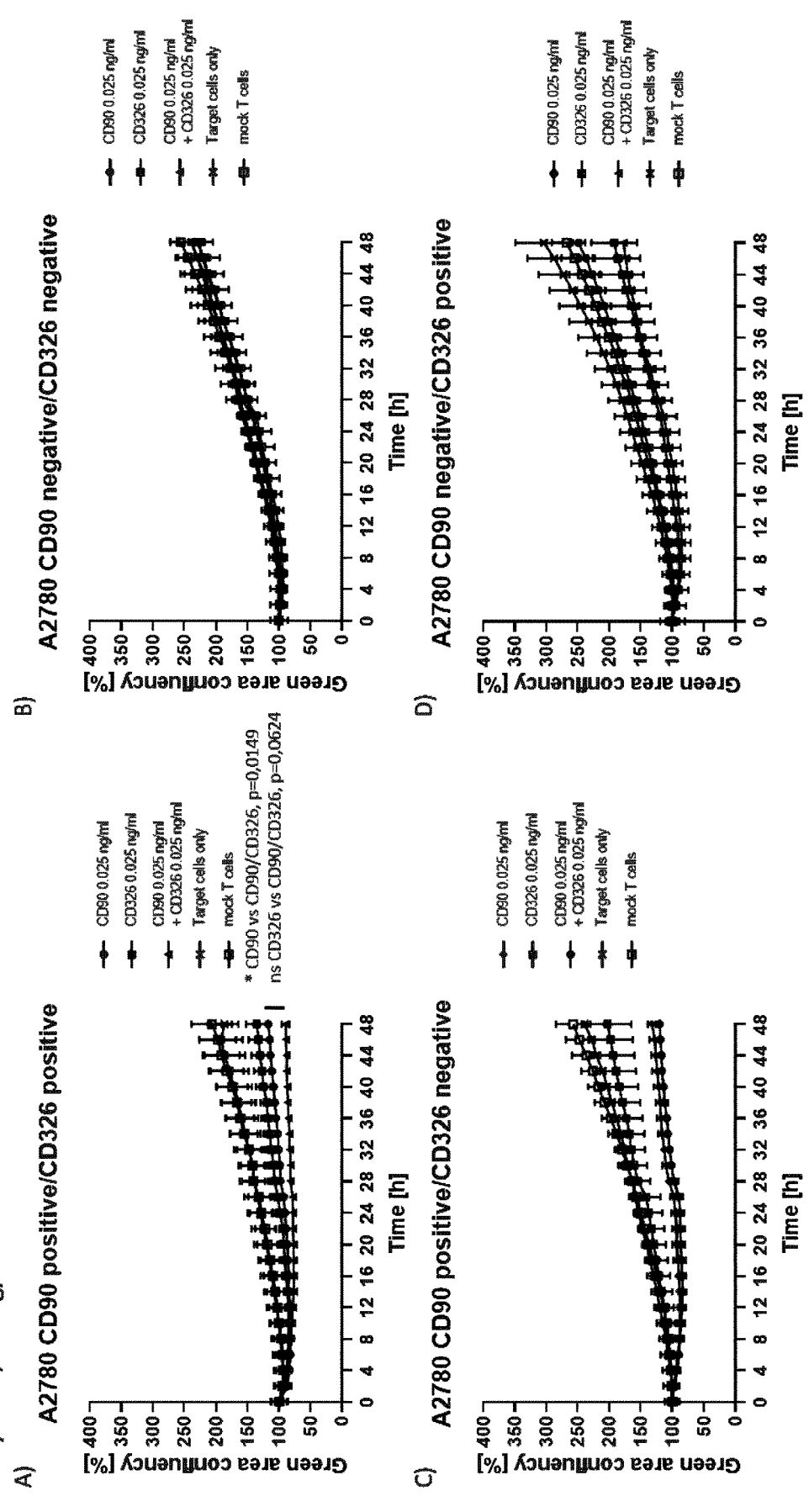

FIG. 19 Adapter CAR T cells targeting CD90 and CD326 show tumor growth control at low dosage of 0,025 ng/ml of adapter against ovarian cancer cell line co-expressing CD90 and CD326

Primary human T cells were isolated and transduced with the indicated CAR construct against biotin. Anti-biotin CAR T cells were co-cultured with CD90+/CD326+ (A), CD90−/D326− (B), CD90+/CD326− (C) and CD90−/CD326+ (D) expressing target cells ovarian cancer cell line A2780 for 48 h in the presence of monobiotinylated anti-CD90 or mono-biotinylated anti-CD326 FAbs, respectively. All A2780 ovarian cancer cell line expresses GFP. GFP-fluorescence was measured over time. CAR T cell mediated lysis of target cells results in decreased GFP-fluorescence. Statistical analysis included unpaired student's t test.

Figure 20:
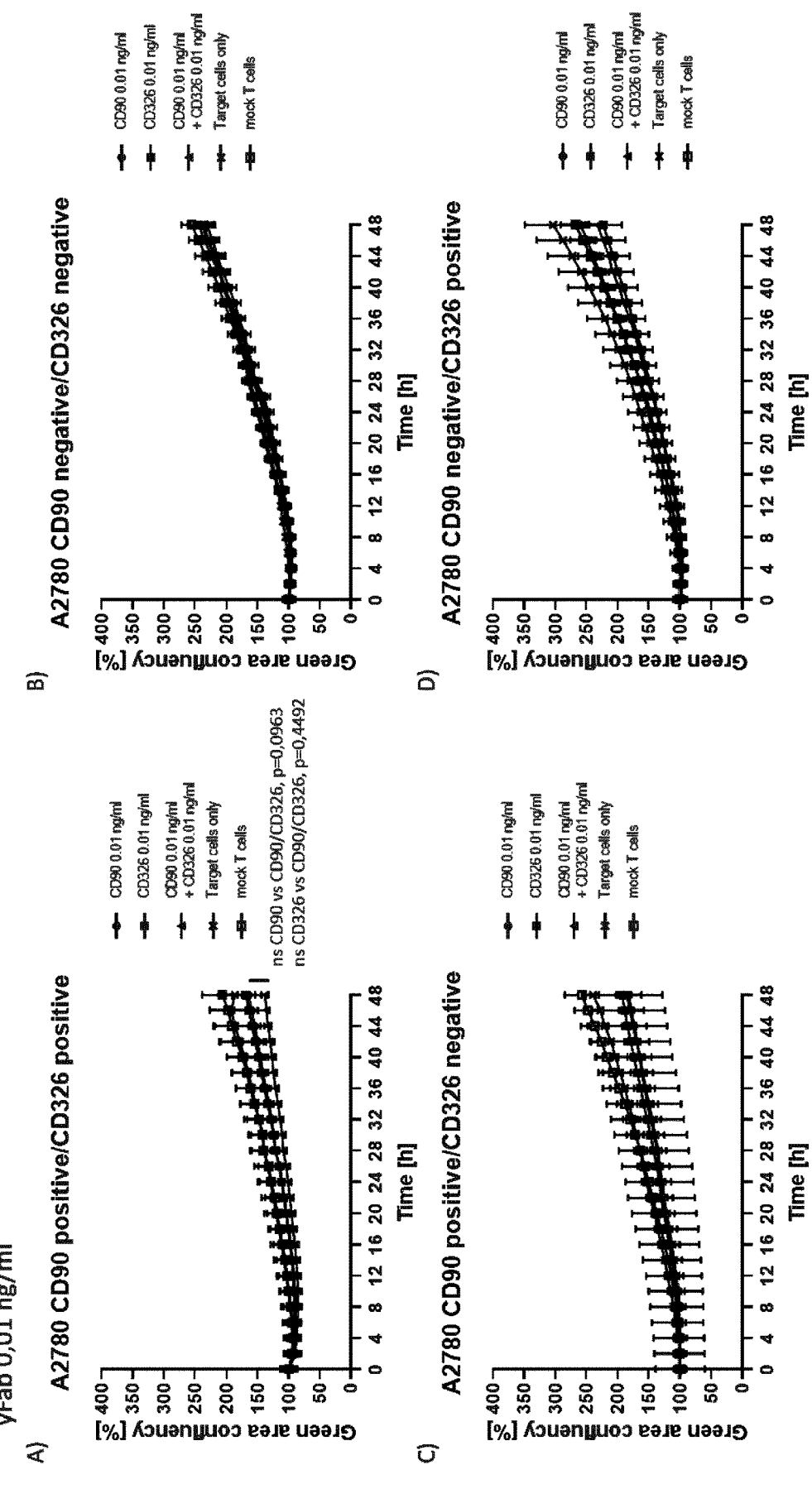

FIG. 20 Adapter CAR T cells targeting CD90 and CD326 show reduced tumor growth control at low dosage of 0.01 ng/ml of adapter against ovarian cancer cell line co-expressing CD90 and CD326 Primary human T cells were isolated and transduced with the indicated CAR construct against biotin. Anti-biotin CAR T cells were co-cultured with CD90+/CD326+ (A), CD90−/CD326− (B), CD90+/CD326− (C) and CD90−/CD326+ (D) expressing target cells ovarian cancer cell line A2780 for 48 h in the presence of monobiotinylated anti-CD90 or monobiotinylated anti-CD326 FAbs, respectively. All A2780 ovarian cancer cell line expresses GFP. GFP-fluorescence was measured over time. CAR T cell mediated lysis of target cells results in decreased GFP-fluorescence. Statistical analysis included unpaired student's t test.

Figure 21:
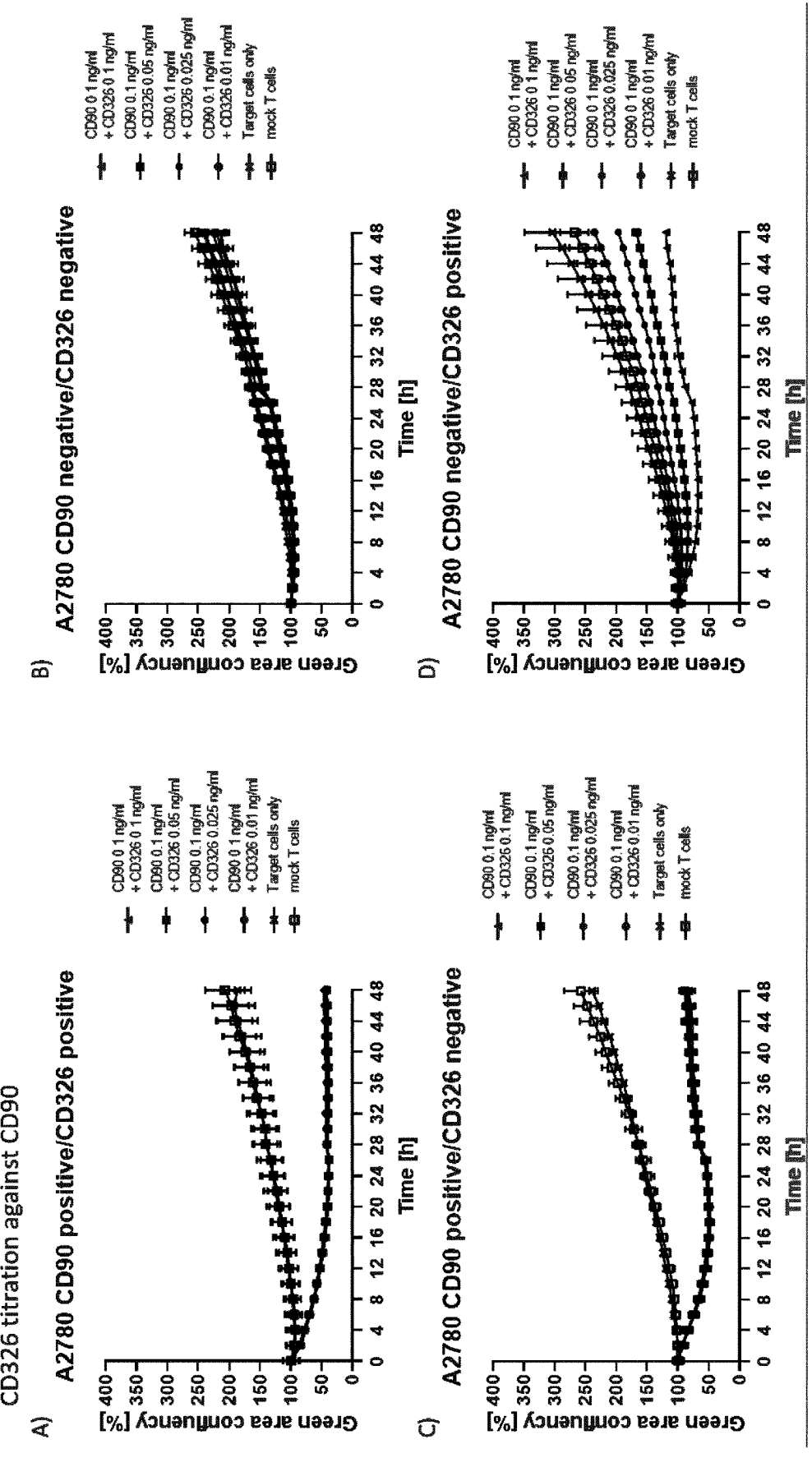

FIG. 21 Adapter CAR T cells targeting CD90 and CD326 are cytolytically active against ovarian cancer cell line co-expressing CD90 and CD326 when anti-CD326 Fabs are titrated against a constant concentration of anti-CD90 Fab Primary human T cells were isolated and transduced with the indicated CAR construct against biotin. Anti-biotin CAR T cells were co-cultured with CD90+/CD326+ (A), CD90−/CD326− (B), CD90+/CD326− (C) and CD90−/CD326+ (D) expressing target cells ovarian cancer cell line A2780 for 48 h in the presence of monobiotinylated anti-CD90 or mono-biotinylated anti-CD326 FAbs, respectively. All A2780 ovarian cancer cell line expresses GFP. GFP-fluorescence was measured over time. CAR T cell mediated lysis of target cells results in decreased GFP-fluorescence. Statistical analysis included unpaired student's t test.

Figure 22:
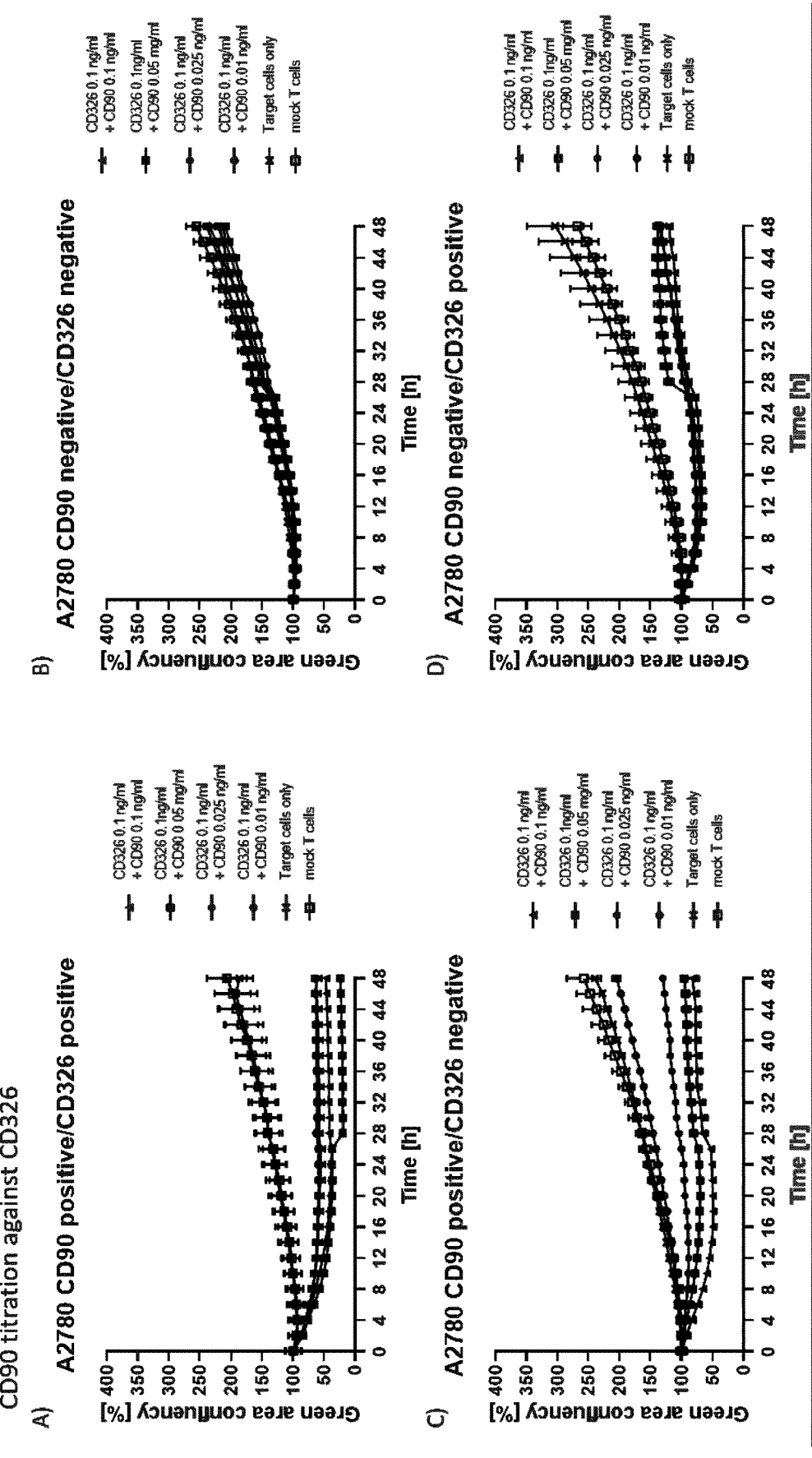

FIG. 22 Adapter CAR T cells targeting CD90 and CD326 are cytolytically active against ovarian cancer cell line co-expressing CD90 and CD326 when anti-CD90 Fabs are titrated against a constant concentration of anti-CD326 Fab Primary human T cells were isolated and transduced with the indicated CAR construct against biotin. Anti-biotin CAR T cells were co-cultured with CD90+/CD326+ (A), CD90−/CD326− (B), CD90+/CD326− (C) and CD90−/CD326+ (D) expressing target cells ovarian cancer cell line A2780 for 48 h in the presence of monobiotinylated anti-CD90 or mono-biotinylated anti-CD326 FAbs, respectively. All A2780 ovarian cancer cell line expresses GFP. GFP-fluorescence was measured over time. CAR T cell mediated lysis of target cells results in decreased GFP-fluorescence. Statistical analysis included unpaired student's t test.

FIG. 23 Adapter CAR T cells targeting CD90 and CD326 secret cytokines at various concentrations against ovarian cancer cell line co-expressing CD90 and CD326 (0.75-0.1 ng/ml)

Primary human T cells were isolated and transduced with the indicated CAR construct against biotin. Anti-biotin CAR T cells were co-cultured with CD90+/CD326+ (A) 0.75 ng/ml, E) 0.5 ng/ml, I) 0.25 ng/ml, M) 0.1 ng/ml), CD90−/CD326− (B) 0.75 ng/ml, F) 0.5 ng/ml, J) 0.25 ng/ml, N) 0.1 ng/ml), CD90+/CD326− (C) 0.75 ng/ml, G) 0.5 ng/ml, K) 0.25 ng/ml, 0) 0.1 ng/ml) and CD90−/CD326+ (D) 0.75 ng/ml, H) 0.5 ng/ml, L) 0.25 ng/ml, P) 0.1 ng/ml) expressing target cells ovarian cancer cell line A2780 for 48 h in the presence of monobiotinylated anti-CD90 or monobiotinylated anti-CD326 FAbs, respectively. Statistical analysis included unpaired student's t test.

FIG. 24 Adapter CAR T cells targeting CD90 and CD326 secret cytokines at various concentrations against ovarian cancer cell line co-expressing CD90 and CD326 (0.1-0.01 ng/ml)

Primary human T cells were isolated and transduced with the indicated CAR construct against biotin. Anti-biotin CAR T cells were co-cultured with CD90+/CD326+ (A) 0.1 ng/ml, E) 0.05 ng/ml, I) 0,025 ng/ml, M) 0.01 ng/ml), CD90−/CD326− (B) 0.1 ng/ml, F) 0.05 ng/ml, J) 0,025 ng/ml, N) 0.01 ng/ml), CD90+/CD326− (C) 0.1 ng/ml, G) 0.05 ng/ml, K) 0,025 ng/ml, 0) 0.01 ng/ml) and CD90−/CD326+ (D) 0.1 ng/ml, H) 0.05 ng/ml, L) 0,025 ng/ml, P) 0.01 ng/ml) expressing target cells ovarian cancer cell line A2780 for 48 h in the presence of monobiotinylated anti-CD90 or monobiotinylated anti-CD326 FAbs, respectively. Statistical analysis included unpaired student's t test.

FIG. 25 Adapter CAR T cells targeting CD90 and CD326 secret cytokines at various concentrations against ovarian cancer cell line co-expressing CD90 and CD326

Primary human T cells were isolated and transduced with the indicated CAR construct against biotin. Anti-biotin CAR T cells were co-cultured with CD90+/CD326+ (A) constant anti-CD326 Fab and anti-CD90 titration, E) constant anti-CD90 Fab and anti-CD326 titration), CD90−/CD326− (B) constant anti-CD326 Fab and anti-CD90 titration, F) constant anti-CD90 Fab and anti-CD326 titration), CD90+/CD326− (C) constant anti-CD326 Fab and anti-CD90 titration, G) constant anti-CD90 Fab and anti-CD326 titration) and CD90–/CD326+ (D) constant anti-CD326 Fab and anti-CD90 titration, H) constant anti-CD90 Fab and anti-CD326 titration) expressing target cells ovarian cancer cell line A2780 for 48 h in the presence of monobiotinylated anti-CD90 or monobiotinylated anti-CD326 FAbs, respectively. Statistical analysis included unpaired student's t test.

FIG. 26 Adapter CAR T cells targeting CD90 and CD326 express activation and exhaustion markers in co-culture with ovarian cancer cell line co-expressing CD90 and CD326 at various concentrations (1-0.1 ng/ml)

Primary human T cells were isolated and transduced with the indicated CAR construct against biotin. Anti-biotin CAR T cells were co-cultured with CD90+/CD326+ (A) 1 ng/ml E) 0.75 ng/ml, I) 0.5 ng/ml, M) 0.25 ng/ml, Q) 0.1 ng/ml), CD90–/CD326– (B) 1 ng/ml, F) 0.75 ng/ml, J) 0.5 ng/ml, N) 0.25 ng/ml, R) 0.1 ng/ml), CD90+/CD326– (C) 1 ng/ml, G) 0.75 ng/ml, K) 0.5 ng/ml, 0) 0.25 ng/ml, S) 0.1 ng/ml) and CD90–/CD326+ (D) 1 ng/ml, H) 0.75 ng/ml, L) 0.5 ng/ml, P) 0.25 ng/ml, T) 0.1 ng/ml) expressing target cells ovarian cancer cell line A2780 for 48 h in the presence of monobiotinylated anti-CD90 or monobiotinylated anti-CD326 FAbs, respectively. Statistical analysis included unpaired student's t test.

FIG. 27 Adapter CAR T cells targeting CD90 and CD326 express activation and exhaustion markers in co-culture with ovarian cancer cell line co-expressing CD90 and CD326 at various concentrations (0.1-0.01 ng/ml)

Primary human T cells were isolated and transduced with the indicated CAR construct against biotin. Anti-biotin CAR T cells were co-cultured with CD90+/CD326+(CD90+/ CD326+ (A) 0.1 ng/ml, E) 0.05 ng/ml, I) 0,025 ng/ml, M) 0.01 ng/ml), CD90–/CD326– (B) 0.1 ng/ml, F) 0.05 ng/ml, J) 0,025 ng/ml, N) 0.01 ng/ml), CD90+/CD326– (C) 0.1 ng/ml, G) 0.05 ng/ml, K) 0,025 ng/ml, 0) 0.01 ng/ml) and CD90–/CD326+ (D) 0.1 ng/ml, H) 0.05 ng/ml, L) 0,025 ng/ml, P) 0.01 ng/ml) expressing target cells ovarian cancer cell line A2780 for 48 h in the presence of biotinylated CD90 or biotinylated CD326 FAbs, respectively. Non-binding FAbs do not led T cell activation and the presence of adapter CARs is essential for adapter specific T cell activation. Statistical analysis included unpaired student's t test.

FIG. 28 Adapter CAR T cells targeting CD90 and CD326 express activation markers in co-culture with ovarian cancer cell line co-expressing CD90 and CD326 at various concentrations Primary human T cells were isolated and transduced with the indicated CAR construct against biotin. Anti-biotin CAR T cells were co-cultured with CD90+/ CD326+ (A) constant anti-CD326 Fab and anti-CD90 titration, D) constant anti-CD90 Fab and anti-CD326 titration), CD90+/CD326– (B) constant anti-CD326 Fab and anti-CD90 titration, E) constant anti-CD90 Fab and anti-CD326 titration), and CD90–/CD326+(C) constant anti-CD326 Fab and anti-CD90 titration, F) constant anti-CD90 Fab and anti-CD326 titration) expressing target cells ovarian cancer cell line A2780 for 48 h in the presence of monobiotinylated anti-CD90 or monobiotinylated anti-CD326 FAbs, respectively. Statistical analysis included unpaired student's t test.

FIG. 29 Adapter CAR T cells targeting CD90 and CD326 express exhaustion markers in co-culture with ovarian cancer cell line co-expressing CD90 and CD326 at various concentrations Primary human T cells were isolated and transduced with the indicated CAR construct against biotin. Anti-biotin CAR T cells were co-cultured with CD90+/CD326+ (A) constant anti-CD326 Fab and anti-CD90 titration), CD90–/CD326– (B)

constant anti-CD326 Fab and anti-CD90 titration, F) constant anti-CD90 Fab and anti-CD326 titration), CD90+/ CD326– (C) constant anti-CD326 Fab and anti-CD90 titration, G) constant anti-CD90 Fab and anti-CD326 titration) and CD90–/CD326+ (D) constant anti-CD326 Fab and anti-CD90 titration, H) constant anti-CD90 Fab and anti-CD326 titration) expressing target cells ovarian cancer cell line A2780 for 48 h in the presence of monobiotinylated anti-CD90 or monobiotinylated anti-CD326 FAbs, respectively. Statistical analysis included unpaired student's t test.

FIG. 30 Adapter CAR T cells targeting CD90 and CD326 express activation markers in co-culture with ovarian cancer cell line co-expressing CD90 and CD326 at various concentrations Primary human T cells were isolated and transduced with the indicated CAR construct against biotin. Anti-biotin CAR T cells were co-cultured with CD90+/ CD326+ (A) constant anti-CD326 Fab and anti-CD90 titration, E) constant anti-CD90 Fab and anti-CD326 titration), CD90–/CD326– (B) constant anti-CD326 Fab and anti-CD90 titration, F) constant anti-CD90 Fab and anti-CD326 titration), CD90+/CD326– (C) constant anti-CD326 Fab and anti-CD90 titration, G) constant anti-CD90 Fab and anti-CD326 titration) and CD90–/CD326+ (D) constant anti-CD326 Fab and anti-CD90 titration, H) constant anti-CD90 Fab and anti-CD326 titration) expressing target cells ovarian cancer cell line A2780 for 48 h in the presence of monobiotinylated anti-CD90 or monobiotinylated anti-CD326 FAbs, respectively, and stained for exhaustion markers.

Anti-biotin CAR T cells were co-cultured with CD90+/ CD326+(I) constant anti-CD326 Fab and anti-CD90 titration, M) constant anti-CD90 Fab and anti-CD326 titration), CD90–/CD326– (J) constant anti-CD326 Fab and anti-CD90 titration, N) constant anti-CD90 Fab and anti-CD326 titration), CD90–/CD326+(K) constant anti-CD326 Fab and anti-CD90 titration, 0) constant anti-CD90 Fab and anti-CD326 titration) and CD90+/CD326– (L) constant anti-CD326 Fab and anti-CD90 titration, P) constant anti-CD90 Fab and anti-CD326 titration) expressing target cells ovarian cancer cell line A2780 for 48 h in the presence of monobiotinylated anti-CD90 or monobiotinylated anti-CD326 FAbs, respectively, and stained for activation markers.

Statistical analysis included unpaired student's t test.

DETAILED DESCRIPTION OF THE INVENTION

In a first aspect the present invention provides a combination comprising
a) an antigen binding domain specific for CD90
b) an antigen binding domain specific for CD326
for use in treatment of human cancer comprising cancerous cells that co-express CD90 and CD326.

Said human cancer comprising cancerous cells that co-express CD90 and CD326 may be human ovarian cancer comprising cancerous cells co-expressing CD90 and CD326.

Said combination, wherein said combination may comprise an immune cell comprising a first
CAR and a second CAR,
the first CAR may comprise
i) a first antigen binding domain specific for CD90 or CD326
ii) a transmembrane domain
iii) a first intracellular signaling domain
wherein said first intracellular signaling domain is a primary signaling domain comprising an immunoreceptor tyrosine-based activation motif (ITAM), wherein said first intracellular signaling domain does not comprise a costimulatory domain, and the second CAR comprising i) a second antigen binding domain specific for CD326 if the first antigen binding domain of the first CAR is specific for CD90, or a second antigen binding domain specific for CD90 if the first antigen binding domain of the first CAR is specific for CD326 ii) a transmembrane domain iii) a second intracellular signaling domain, wherein said second intracellular signaling domain comprises one or more co-stimulatory signaling domains.

Said combination, wherein said combination may comprise an immune cell comprising a first CAR and a second CAR, and wherein said immune cell becomes maximally cytotoxic only when said first signaling domain and said second signaling domain are both activated by said CD90 and CD326, respectively.

Said ITAM may be preferably CD3ζ signaling domain.

Said primary cytoplasmic signaling domain of said CAR may be CD3ζ.

Said transmembrane domain of said first CAR and said transmembrane domain of said second CAR may be identical or different from each other.

Said first CAR may comprise a spacer between said first antigen binding domain and said transmembrane domain.

Said second CAR may comprise a spacer between said second antigen binding domain and said transmembrane domain.

Said spacer of said first CAR and said spacer of said second CAR may be identical or different from each other.

Said second CAR may herein also be referred to as chimeric costimulatory receptor (CCR).

Said CCR that may comprise said second intracellular signaling domain, wherein said second intracellular signaling domain may comprise one or more co-stimulatory signaling domains but may not comprise an immunoreceptor tyrosine-based activation motif (ITAM) such as CD3zeta. Said CCR, wherein said second intracellular signaling domain may consist of one or more co-stimulatory signaling domains Said one or more (or at least one) co-stimulatory signaling domain(s) may be selected from the group consisting of ICOS, CD154, CD5, CD2, CD46, HVEM, CD8, CD97, TNFRSF18, CD30, SLAM, DAP10, CD64, CD16, CD89, MyD88, KIR-2DS, KIR-3DS, NKp30, NKp44, NKp46, NKG2D, ICAM, CD27, OX40, 4-1BB and CD28.

Said intracellular signaling domain of said CCR may comprise or consist of one 4-1BB co-stimulatory signaling domain and one CD28 co-stimulatory signaling domain.

Said immune cell may be a T cell or an NK cell.

Said antigen binding domain of the CAR specific for CD90 may comprise the SEQ ID NO:1 and the SEQ ID NO:2.

Said antigen binding domain of the CAR specific for CD326 may comprise the SEQ ID NO:3 and the SEQ ID NO:4

Said combination, wherein said combination comprises an immune cell comprising a first CAR and a second CAR, the first CAR comprising i) a first antigen binding domain specific for a tag of a tagged polypeptide, wherein said polypeptide has an antigen binding domain specific for CD90 or CD326 ii) a transmembrane domain iii) a first intracellular signaling domain wherein said first intracellular signaling domain is a primary signaling domain comprising an immunoreceptor tyrosine-based activation motif (ITAM), wherein said first intracellular signaling domain does not comprise a costimulatory domain, and the second CAR comprising i) a second antigen binding domain specific for CD326 if said tagged polypeptide specifically binds to CD90, or a second antigen binding domain specific for CD90 if said tagged polypeptide specifically binds to CD326 ii) a transmembrane domain iii) a second intracellular signaling domain, wherein said second intracellular signaling domain comprises one or more co-stimulatory signaling domains, and wherein said combination comprises said tagged polypeptide.

Said combination, wherein said combination comprises an immune cell comprising a first CAR and a second CAR, and wherein said immune cell becomes maximally cytotoxic only when said first signaling domain is activated by said tag and said second signaling domain is activated by said CD90 or CD326.

The polypeptide of said tagged polypeptide may be an antibody or antigen binding fragment thereof, wherein said antibody or antigen binding fragment thereof may bind to said CD90 or said CD326.

Said antigen binding domain of the tagged polypeptide specific for CD90 may comprise the SEQ ID NO:1 and the SEQ ID NO:2.

Said antigen binding domain of the tagged polypeptide specific for CD326 may comprise the SEQ ID NO:3 and the SEQ ID NO:4

The tag of said tagged polypeptide may be e.g. a hapten. Said hapten may be e.g. FITC, biotin, PE, thiamin or streptavidin.

Said combination, wherein said combination comprises an immune cell comprising a first CAR and a second CAR, the first CAR comprising i) a first antigen binding domain specific for CD90 or CD326 ii) a transmembrane domain iii) a first intracellular signaling domain wherein said first intracellular signaling domain is a primary signaling domain comprising an immunoreceptor tyrosine-based activation motif (ITAM), wherein said first intracellular signaling domain does not comprise a costimulatory domain, and the second CAR comprising i) a second antigen binding domain specific for a tag of a tagged polypeptide wherein said polypeptide has an antigen binding domain specific for CD326 if the first antigen binding domain of the first CAR is specific for CD90, or a second antigen binding domain specific for a tagged polypeptide, wherein said polypeptide has an antigen binding domain specific for CD90 if the first antigen binding domain of the first CAR is specific for CD326 ii) a transmembrane domain iii) a second intracellular signaling domain, wherein said second intracellular signaling domain comprises one or more co-stimulatory signaling domains, and wherein said combination comprises said tagged polypeptide.

Said combination, wherein said combination comprises an immune cell comprising a first CAR and a second CAR, and wherein said immune cell becomes maximally cytotoxic only when said first signaling domain is activated by said CD90 or CD326 and said second signaling domain is activated by said tag.

Said combination, wherein said combination comprises an immune cell comprising a first CAR and a second CAR, the first CAR comprising i) a first antigen binding domain specific for a first tag of a first tagged polypeptide, wherein said first polypeptide has an antigen binding domain specific for CD90 or CD326 ii) a transmembrane domain iii) a first intracellular signaling domain wherein said first intracellular signaling domain is a primary signaling domain comprising an immunoreceptor tyrosine-based activation motif (ITAM), wherein said first intracellular signaling domain does not comprise a costimulatory domain, and the second CAR comprising i) a second antigen binding domain specific for a second tag of a second tagged polypeptide, wherein said second polypeptide has an antigen binding domain specific for CD326 if said first tagged polypeptide specifically binds to CD90, or a second antigen binding domain specific for a second tagged polypeptide wherein said second polypeptide has an antigen binding domain specific for CD90 if said first tagged polypeptide specifically binds to CD326 ii) a transmembrane domain iii) a second intracellular signaling domain, wherein said second intracellular signaling domain comprises one or more co-stimulatory signaling domains, and wherein said combination comprises said first tagged polypeptide and said second tagged polypeptide.

Said combination, wherein said combination comprises an immune cell comprising a first CAR and a second CAR, and wherein said immune cell becomes maximally cytotoxic only when said first signaling domain and said second signaling domain are both activated by said first tag and said second tag, respectively.

Said first tag of said first tagged polypeptide may be different from said second tag of said second tagged polypeptide.

Said combination, wherein said combination comprises a) a tagged first polypeptide having an antigen binding domain specific for CD90, b) a tagged second polypeptide having an antigen binding domain specific for CD326, wherein the tag of the first polypeptide and the tag of the second polypeptide are identical, c) an immune cell comprising a CAR, the CAR comprising i) an antigen binding domain specific for said tag of the first and second polypeptides, ii) a transmembrane domain iii) an intracellular signaling domain comprising a primary signaling domain and at least one costimulatory domain.

Said combination, wherein the concentration of said tagged first polypeptide (in a subject in need thereof) is below the activation threshold of said CAR expressed in said immune cell, wherein the concentration of said tagged second polypeptide (in said subject in need thereof) is below the activation threshold of said CAR expressed in said immune cell, wherein the combined concentrations of the tagged first polypeptide and the tagged second polypeptide (in said subject in need thereof) is above the activation threshold of said CAR expressed in said immune cell (when said combination is applied to said subject in need thereof).

Said combination, wherein the concentration of said tagged first polypeptide (in a subject in need thereof) is below the activation threshold of said CAR expressed in said immune cell, wherein the concentration of said tagged second polypeptide (in said subject in need thereof) is below the activation threshold of said CAR expressed in said immune cell, wherein the combined concentrations of the tagged first polypeptide and the tagged second polypeptide (in said subject in need thereof) is above the activation threshold of said CAR expressed in said immune cell (when said combination is applied to said subject), wherein the concentration of said tagged first polypeptide is at least 10% below the concentration that is needed when the CAR is activated solely by said tagged first polypeptide, i.e. without the presence of said tagged second polypeptide, and wherein the concentration of said tagged second polypeptide is at least 10% below the concentration that is needed when the CAR is activated solely by said tagged second polypeptide, i.e. without the presence of said tagged first polypeptide.

Said combination, wherein the concentration of said tagged first polypeptide (in said combination) is $x(1)$ µg/ml, wherein the concentration of said tagged second polypeptide (in said combination) is $x(2)$ µg/ml, wherein $x(1)$ is less than $x(total)$ µg/ml, wherein $x(2)$ is less than $x(total)$ µg/ml, wherein $x(1)$ µg/ml+$x(2)$ µg/ml is equal or higher than $x(total)$ µg/ml, and wherein $x(total)$ µg/ml is the concentration (in said combination) that triggers the activation of said immune cell.

Said combination, wherein the concentration of said tagged first polypeptide is not sufficient to activate said CAR expressed in said immune cell, wherein the concentration of said tagged second polypeptide is not sufficient to activate said CAR expressed in said immune cell, wherein the combined concentrations of the tagged first polypeptide and the tagged second polypeptide are sufficient to activate said CAR expressed in said immune cell.

Said combination, wherein the concentration of said tagged first polypeptide is below the activation threshold of said CAR expressed in said immune cell, wherein the concentration of said tagged second polypeptide is below the activation threshold of said CAR expressed in said immune cell, wherein the combined concentrations of the tagged first polypeptide and the tagged second polypeptide is above the activation threshold of said CAR expressed in said immune cell, wherein the value for the activation threshold of said CAR expressed in said immune cell can be determined by a titration curve using individually both tagged polypeptides, respectively, and target cells expressing CD90 and CD326, thereby allowing the activation of said immune cell and determining the threshold, when activation of said immune cells occurs.

The CAR system comprising an adapter CAR and at least two tagged polypeptides having specificity for at least two different antigens, wherein the at least two polypeptides have identical tags and wherein the activation of said CAR is regulated by the concentration of said at least two polypeptides is also referred to as surface activation matrix (SAM) CAR approach. Due to the complex surface phenotype of target cells adapter (tagged polypeptides) mixes can be adjusted to specifically achieve the activation threshold on a particular combination of target antigens.

"Below the activation threshold of said CAR expressed in said immune cell" and "above the activation threshold of said CAR expressed in said immune cell" refer to the ability for activating and stimulating an immune response of said immune effector cell as disclosed herein by binding of the tagged polypeptide(s) to the respective CAR of the immune cell. If the concentration of a tagged polypeptide or the sum of tagged polypeptides is too low for activation of the CAR, then said concentration is below the activation threshold of said CAR expressed in said immune cell. If the concentration of a tagged polypeptide or the sum of concentrations (the combined concentrations) of the tagged first polypeptide and the tagged second polypeptide as disclosed herein is sufficient to activate the CAR, then the concentration or the combined concentrations are above the activation threshold of said CAR expressed in said immune cell.

The concentration of a tagged polypeptide or the sum of concentrations (the combined concentrations) of the tagged first polypeptide and the tagged second polypeptide as disclosed herein may be sufficient to activate the CAR, i.e. the concentration or the combined concentrations may be above the activation threshold of said CAR expressed in said immune cell, when the concentration of the tagged polypeptide or the sum of concentrations (the combined concentrations) of the tagged first polypeptide and the tagged second polypeptide as disclosed may be at least 1 fg/ml, at least 1 pg/ml, at least 1 ng/ml, or at least 1 µg/ml.

Said antigen binding domain of the tagged polypeptide specific for CD90 may comprise the SEQ ID NO:1 and the SEQ ID NO:2.

Said antigen binding domain of the tagged polypeptide specific for CD326 may comprise the SEQ ID NO:3 and the SEQ ID NO:4.

Said combination for use in treatment of human cancer comprising cancerous cells that co-express CD90 and CD326, wherein said combination comprises a) a tagged first polypeptide having an antigen binding domain specific for CD90, b) a tagged second polypeptide having an antigen binding domain specific for CD326, wherein the tag of the first polypeptide and the tag of the second polypeptide are identical, c) an immune cell comprising a CAR, the CAR comprising i) an antigen binding domain specific for said tag of the first and second polypeptides, ii) a transmembrane domain iii) an intracellular signaling domain comprising a primary signaling domain and at least one costimulatory domain.

Said combination for use in treatment of human cancer, wherein the concentration of said tagged first polypeptide is below the activation threshold of said CAR expressed in said immune cell, when applied to a subject (human) in need thereof, and wherein the concentration of said tagged second polypeptide is below the activation threshold of said CAR expressed in said immune cell, when applied to said subject (human) in need thereof, and wherein the combined concentrations of the tagged first polypeptide and the tagged second polypeptide in said subject is above the activation threshold of said CAR expressed in said immune cell.

In another aspect the present invention provides an Antibody-Drug-Conjugate (ADC), wherein said ADC comprises a bispecific antibody or antigen binding fragment thereof specific for CD90 and said CD326, wherein said bispecific antibody or antigen-binding fragment thereof is conjugated to a drug. Said ADC, wherein only the combination of binding affinities of both the CD90 and CD326 antigen binding fragments is sufficiently strong to bind a cell co-expressing CD90 and CD326.

Said ADC, wherein said bispecific antibody or antigen-binding fragment thereof mediates antibody-dependent cell-mediated cytotoxicity by an effector immune cell.

Antibody-dependent cellular cytotoxicity (ADCC) activities are mediated by the interaction of an antibodies Fc fragment with an Fc-receptors expressed by—but not restricted to—B lymphocytes, follicular dendritic cells, natural killer cells, macrophages, neutrophils, eosinophils, basophils, human platelets, and mast cells.

Said ADC, wherein said bispecific antibody or antigen-binding fragment thereof mediates apoptosis upon receptor cross-linking.

Said ADC, wherein said bispecific antibody or antigen-binding fragment thereof mediates complement dependent cytotoxicity.

Complement-dependent cytotoxicity (CDC) is mediated by the interaction of an antibodies Fc fragment with complement cascade proteins such as C1q and C5.

In another aspect the present invention provides an immune cell comprising a first CAR and a second CAR, the first CAR comprising i) a first antigen binding domain specific for CD90 or CD326 ii) a transmembrane domain iii) a first intracellular signaling domain wherein said first intracellular signaling domain is a primary signaling domain comprising an immunoreceptor tyrosine-based activation motif (ITAM), wherein said first intracellular signaling domain does not comprise a costimulatory domain, and the second CAR comprising i) a second antigen binding domain specific for CD326 if the first antigen binding domain of the first CAR is specific for CD90, or a second antigen binding domain specific for CD90 if the first antigen binding domain of the first CAR is specific for CD236 ii) a transmembrane domain iii) a second intracellular signaling domain, wherein said second intracellular signaling domain comprises one or more co-stimulatory signaling domains.

Said immune cell comprising a first CAR and a second CAR, and wherein said immune cell becomes maximally cytotoxic only when said first signaling domain and said second signaling domain are both activated by said CD90 and CD326, respectively.

Said immune cell for use in treating human cancer comprising cancerous cells co-expressing CD90 and CD326.

Said immune cell for use in treating human ovarian cancer comprising cancerous cells co-expressing CD90 and CD326.

A pharmaceutical composition comprising said immune cell, optionally comprising a pharmaceutical acceptable carrier.

A physiologically acceptable carriers (diluents or excipients) may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

In another aspect the present invention provides a composition comprising a) an immune cell comprising a first CAR and a second CAR, the first CAR comprising i) a first antigen binding domain specific for a tag of a tagged polypeptide, wherein said polypeptide has an antigen binding domain specific for CD90 or CD326 ii) a transmembrane domain iii) a first intracellular signaling domain wherein said first intracellular signaling domain is a primary signaling domain comprising an immunoreceptor tyrosine-based activation motif (ITAM), wherein said first intracellular signaling domain does not comprise a costimulatory domain,
and the second CAR comprising
    i) a second antigen binding domain specific for CD326 if said tagged polypeptide specifically binds to CD90, or a second antigen binding domain specific for CD90 if said tagged polypeptide specifically binds to CD326
    ii) a transmembrane domain
    iii) a second intracellular signaling domain,
wherein said second intracellular signaling domain comprises one or more co-stimulatory signaling domains,
    b) said tagged polypeptide.
    Said composition, wherein said immune cell becomes maximally cytotoxic only when said first signaling domain is activated by said tag and said second signaling domain is activated by said CD90 or CD326,
    Said composition for use in treating human cancer comprising cancerous cells co-expressing CD90 and CD326.
    Said composition for use in treating human ovarian cancer comprising cancerous cells co-expressing CD90 and CD326.
    Said composition, wherein said composition is a pharmaceutical composition optionally comprising a pharmaceutical acceptable carrier.
    In another aspect the present invention provides a composition comprising
    a) an immune cell comprising a first CAR and a second CAR,
the first CAR comprising
    i) a first antigen binding domain specific for CD90 or CD326
    ii) a transmembrane domain
    iii) a first intracellular signaling domain
wherein said first intracellular signaling domain is a primary signaling domain comprising an immunoreceptor tyrosine-based activation motif (ITAM), wherein said first intracellular signaling domain does not comprise a costimulatory domain,
and the second CAR comprising
    i) a second antigen binding domain specific for a tagged of a tagged polypeptide wherein said polypeptide has an antigen binding domain specific for CD326 if the first antigen binding domain of the first CAR is specific for CD90, or a second antigen binding domain specific for a tagged polypeptide, wherein said polypeptide has an antigen binding domain specific for CD90 if the first antigen binding domain of the first CAR is specific for CD326
    ii) a transmembrane domain
    iii) a second intracellular signaling domain,
wherein said second intracellular signaling domain comprises one or more co-stimulatory signaling domains,
    b) said tagged polypeptide.
    Said composition, wherein said immune cell becomes maximally cytotoxic only when said first signaling domain is activated by said CD90 or CD326 and said second signaling domain is activated by said tag.
    Said composition for use in treating human cancer comprising cancerous cells co-expressing CD90 and CD326.
    Said composition for use in treating human ovarian cancer comprising cancerous cells co-expressing CD90 and CD326.
    Said composition, wherein said composition is a pharmaceutical composition optionally comprising a pharmaceutical acceptable carrier.

In another aspect the present invention provides a composition comprising
    a) an immune cell comprising a first CAR and a second CAR, the first CAR comprising
    i) a first antigen binding domain specific for a first tag of a first tagged polypeptide, wherein said first polypeptide has an antigen binding domain specific for CD90 or CD326
    ii) a transmembrane domain
    iii) a first intracellular signaling domain
wherein said first intracellular signaling domain is a primary signaling domain comprising an immunoreceptor tyrosine-based activation motif (ITAM), wherein said first intracellular signaling domain does not comprise a costimulatory domain,
and the second CAR comprising
    i) a second antigen binding domain specific for a second tag of a second tagged polypeptide, wherein said second polypeptide has an antigen binding domain specific for CD326 if said first tagged polypeptide specifically binds to CD90, or a second antigen binding domain specific for a second tagged polypeptide wherein said second polypeptide has an antigen binding domain specific for CD90 if said first tagged polypeptide specifically binds to CD326
    ii) a transmembrane domain
    iii) a second intracellular signaling domain,
wherein said second intracellular signaling domain comprises one or more co-stimulatory signaling domains,
    b) said first tagged polypeptide and
    c) said second tagged polypeptide.
    Said composition, wherein said immune cell becomes maximally cytotoxic only when said first signaling domain and said second signaling domain are both activated by said first tag and said second tag, respectively.
    Said composition for use in treating human cancer comprising cancerous cells co-expressing CD90 and CD326.
    Said composition for use in treating human ovarian cancer comprising cancerous cells co-expressing CD90 and CD326.
    Said composition, wherein said composition is a pharmaceutical composition optionally comprising a pharmaceutical acceptable carrier.
    In another aspect the present invention provides a composition comprising
    a) a tagged first polypeptide having an antigen binding domain specific for CD90,
    b) a tagged second polypeptide having an antigen binding domain specific for CD326, wherein the tag of the first polypeptide and the tag of the second polypeptide are identical,
    c) an immune cell comprising a CAR, the CAR comprising
    i) an antigen binding domain specific for said tag of the first and second polypeptides,
    ii) a transmembrane domain
    iii) an intracellular signaling domain comprising a primary signaling domain and at least one costimulatory domain.
    Said antigen binding domain of the tagged polypeptide specific for CD90 may comprise the SEQ ID NO:1 and the SEQ ID NO:2.
    Said antigen binding domain of the tagged polypeptide specific for CD326 may comprise the SEQ ID NO:3 and the SEQ ID NO:4.
    Said composition, wherein the concentration of said tagged first polypeptide is below the activation threshold of said CAR expressed in said immune cell, wherein the concentration of said tagged second polypeptide is below the activation threshold of said CAR expressed in said immune cell, wherein the combined concentrations of the tagged first polypeptide and the tagged second polypeptide is above the activation threshold of said CAR expressed in said immune cell.

Said composition for use in treating human cancer comprising cancerous cells co-expressing CD90 and CD326.

Said composition for use in treating human ovarian cancer comprising cancerous cells co-expressing CD90 and CD326.

Said composition, wherein said composition is a pharmaceutical composition optionally comprising a pharmaceutical acceptable carrier.

In another aspect the present invention provides a method for treating a subject suffering from human cancer comprising cancerous cells co-expressing CD90 and CD326, the method comprising a) administering to said subject an Antibody-Drug-Conjugate (ADC), wherein said ADC comprises a bispecific antibody or antigen binding fragment thereof specific for CD90 and said CD326, wherein said bispecific antibody or antigen-binding fragment thereof is conjugated to a drug.

In another aspect the present invention provides a method for treating a subject suffering from human cancer comprising cancerous cells co-expressing CD90 and CD326, the method comprising a) administering to said subject an immune cell comprising a first CAR and a second CAR, the first CAR comprising i) a first antigen binding domain specific for CD90 or CD326 ii) a transmembrane domain iii) a first intracellular signaling domain wherein said first intracellular signaling domain is a primary signaling domain comprising an immunoreceptor tyrosine-based activation motif (ITAM), wherein said first intracellular signaling domain does not comprise a costimulatory domain, and the second CAR comprising i) a second antigen binding domain specific for CD326 if the first antigen binding domain of the first CAR is specific for CD90, or a second antigen binding domain specific for CD90 if the first antigen binding domain of the first CAR is specific for CD236 ii) a transmembrane domain iii) a second intracellular signaling domain, wherein said second intracellular signaling domain comprises one or more co-stimulatory signaling domains.

Said method, wherein said immune cell becomes maximally cytotoxic only when said first signaling domain and said second signaling domain are both activated by said CD90 and CD326, respectively.

In another aspect the present invention provides a method for treating a subject suffering from human cancer comprising cancerous cells co-expressing CD90 and CD326, the method comprising a) administering to said subject an immune cell comprising a first CAR and a second CAR, the first CAR comprising i) a first antigen binding domain specific for a tag of a tagged polypeptide, wherein said polypeptide has an antigen binding domain specific for CD90 or CD326 ii) a transmembrane domain iii) a first intracellular signaling domain wherein said first intracellular signaling domain is a primary signaling domain comprising an immunoreceptor tyrosine-based activation motif (ITAM), wherein said first intracellular signaling domain does not comprise a costimulatory domain, and the second CAR comprising i) a second antigen binding domain specific for CD326 if said tagged polypeptide specifically binds to CD90, or a second antigen binding domain specific for CD90 if said tagged polypeptide specifically binds to CD326 ii) a transmembrane domain iii) a second intracellular signaling domain, wherein said second intracellular signaling domain comprises one or more co-stimulatory signaling domains, b) administering to said subject said tagged polypeptide.

Said method, wherein said immune cell becomes maximally cytotoxic only when said first signaling domain is activated by said tag and said second signaling domain is activated by said CD90 or CD326.

Step a) and step b) of said method may be performed simultaneously, or step a) before step b), or step a) after step b).

In another aspect the present invention provides a method for treating a subject suffering from human cancer comprising cancerous cells co-expressing CD90 and CD326, the method comprising a) administering to said subject an immune cell comprising a first CAR and a second CAR, the first CAR comprising i) a first antigen binding domain specific for CD90 or CD326 ii) a transmembrane domain iii) a first intracellular signaling domain wherein said first intracellular signaling domain is a primary signaling domain comprising an immunoreceptor tyrosine-based activation motif (ITAM), wherein said first intracellular signaling domain does not comprise a costimulatory domain, and the second CAR comprising i) a second antigen binding domain specific for a tagged of a tagged polypeptide wherein said polypeptide has an antigen binding domain specific for CD326 if the first antigen binding domain of the first CAR is specific for CD90, or a second antigen binding domain specific for a tagged polypeptide, wherein said polypeptide has an antigen binding domain specific for CD90 if the first antigen binding domain of the first CAR is specific for CD326 ii) a transmembrane domain iii) a second intracellular signaling domain, wherein said second intracellular signaling domain comprises one or more co-stimulatory signaling domains, b) administering to said subject said tagged polypeptide.

Said method, wherein said immune cell becomes maximally cytotoxic only when said first signaling domain is activated by said CD90 or CD326 and said second signaling domain is activated by said tag.

Step a) and step b) of said method may be performed simultaneously, or step a) before step b), or step a) after step b).

In another aspect the present invention provides a method for treating a subject suffering from human cancer comprising cancerous cells co-expressing CD90 and CD326, the method comprising a) administering to said subject an immune cell comprising a first CAR and a second CAR, the first CAR comprising i) a first antigen binding domain specific for a first tag of a first tagged polypeptide, wherein said first polypeptide has an antigen binding domain specific for CD90 or CD326 ii) a transmembrane domain iii) a first intracellular signaling domain wherein said first intracellular signaling domain is a primary signaling domain comprising an immunoreceptor tyrosine-based activation motif (ITAM), wherein said first intracellular signaling domain does not comprise a costimulatory domain, and the second CAR comprising i) a second antigen binding domain specific for a second tag of a second tagged polypeptide, wherein said second polypeptide has an antigen binding domain specific for CD326 if said first tagged polypeptide specifically binds to CD90, or a second antigen binding domain specific for a second tagged polypeptide wherein said second polypeptide has an antigen binding domain specific for CD90 if said first tagged polypeptide specifically binds to CD326 ii) a transmembrane domain iii) a second intracellular signaling domain, wherein said second intracellular signaling domain comprises one or more co-stimulatory signaling domains, b) administering to said subject said first tagged polypeptide and c) administering to said subject said second tagged polypeptide.

Said method, wherein said immune cell becomes maximally cytotoxic only when said first signaling domain and said second signaling domain are both activated by said first tag and said second tag, respectively.

The steps a), b), and c) of said method may be performed in any order.

In another aspect the present invention provides a method for treating a subject suffering from human cancer comprising cancerous cells co-expressing CD90 and CD326, the method comprising a) administering to said subject a tagged first polypeptide having an antigen binding domain specific for CD90, and b) administering to said subject a tagged second polypeptide having an antigen binding domain specific for CD326, wherein the tag of the first polypeptide and the tag of the second polypeptide are identical, and c) administering to said subject an immune cell comprising a CAR, the CAR comprising i) an antigen binding domain specific for said tag of the first and second polypeptides, ii) a transmembrane domain iii) an intracellular signaling domain comprising a primary signaling domain and at least one costimulatory domain.

Said method, wherein the concentration of said tagged first polypeptide is below the activation threshold of said CAR expressed in said immune cell, wherein the concentration of said tagged second polypeptide is below the activation threshold of said CAR expressed in said immune cell, wherein the combined concentrations of the tagged first polypeptide and the tagged second polypeptide is above the activation threshold of said CAR expressed in said immune cell.

The steps a), b), and c) of said method may be performed in any order.

In one embodiment of the invention the immune cells expressing the first and second CAR specific for CD90 and CD326, respectively, as disclosed herein is for use in treatment of cancer in a subject suffering from cancer comprising cancerous cells co-expressing CD90 and CD326, e.g. human ovarian cancer. Immune cells, e.g. T cells or NK cells of a subject are isolated. The subject may suffer from said cancer or may be a healthy subject. These cells are genetically modified in vitro or in vivo to express said CARs. These engineered cells may be activated and expanded in vitro or in vivo. In a cellular therapy these engineered cells are infused to a recipient in need thereof. These cells may be a pharmaceutical composition (said cell plus pharmaceutical acceptable carrier). The infused cells are able to kill (or at least stop growth of) cancerous cells expressing CD90 and CD326 in the recipient. The recipient may be the same subject from which the cells was obtained (autologous cell therapy) or may be from another subject of the same species.

The immune cells, preferentially T cells or NK cells engineered to express said CARs may be administered either alone, or as a pharmaceutical composition in combination with diluents and/or with other components such as IL-2 or other cytokines or cell populations. Briefly, pharmaceutical compositions of the present invention may comprise a cell population of genetically modified cells as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Preferentially, the compositions of the present invention are formulated for intravenous administration. The administration of cell compositions to the subject may be carried out in any convenient manner known in the art.

Pharmaceutical compositions of the present invention may be administered in a manner appropriate to the disease to be treated. Appropriate dosages may be determined by clinical trials. But the quantity and frequency of administration will also be determined and influenced by such factors as the condition of the patient, and the type and severity of the patient's disease.

A pharmaceutical composition comprising the immune cells, preferentially T cells or NK cells as disclosed herein may be administered at a dosage of $10^4$ to $10^9$ cells/kg body weight, preferably $10^5$ to $10^6$ cells/kg body weight. The cell compositions may also be administered several times at these dosages. The compositions of cells may be injected directly into a tumor, lymph node, or site of infection.

The cells may be activated and expanded to therapeutic effective amounts using methods known in the art.

The cells of the invention may be used in combination with e.g. chemotherapy, radiation, immunosuppressive agents, antibodies or antibody therapies.

In another embodiment, the composition comprising a) an immune cell co-expressing a first CAR specific for CD90 or CD326 as disclosed herein and a second CAR specific for a tag of a tagged polypeptide ("anti-tag CAR") as disclosed herein and b) said polypeptide specifically binding to CD90 or CD326 as disclosed herein may be for use in the treatment in a subject suffering from cancer, wherein said cancer comprises cancerous cells co-expressing CD90 and CD326. Cells such as immune cells, e.g. T cells or NK cells of a subject, may be isolated or established immune cell lines may be used. The subject may suffer from said cancer (a patient) or may be a healthy subject. These immune cells are genetically modified in vitro to express the CARs as disclosed herein. These engineered cells may be activated and expanded in vitro to a therapeutically effective population of expressing cells. In cellular therapy these engineered cells may be infused to a recipient in need thereof as a pharmaceutical composition (or a formulation of a therapeutically effective population of said CARs expressing cells), in addition to a second pharmaceutical composition, a formulation of the tagged polypeptide as disclosed herein. The infused cells in the recipient may be able to kill (or at least stop growth of) cancerous cells expressing the antigen which is recognized by the CARs as disclosed herein. The recipient may be the same subject from which the cells were obtained (autologous cell therapy) or may be from another subject of the same species (allogeneic cell therapy).

The therapeutically effective population of said CARs expressing cells may be administered to the patient before the administration of the formulation of the tagged polypeptide to the subject. Alternatively, the formulation of the tagged polypeptide may be administered to the subject before or at the same time as the administration the therapeutically effective population of said CARs expressing cells to the subject. A further variation includes in-vitro culturing the therapeutically effective population of said CARs expressing cells with the tagged polypeptide of the formulation of the tagged polypeptide prior to administration to the subject.

Populations of said CARs-expressing (immune) cells may be formulated for administered to a subject using techniques known to the skilled artisan.

Formulations comprising therapeutically effective population(s) of said CARs expressing cells may include pharmaceutically acceptable excipient(s) (carrier or diluents). Excipients included in the formulations will have different purposes depending, for example, on the nature of the tag-binding domain of the anti-tag-CAR, the (sub)population of immune cells used, and the mode of administration. Examples of generally used excipients include, without limitation: saline, buffered saline, dextrose, water-for-injection, glycerol, ethanol, and combinations thereof, stabilizing agents, solubilizing agents and surfactants, buffers and preservatives, tonicity agents, bulking agents, and lubricating agents.

A formulation of a therapeutically effective population(s) of said CARs expressing cells may include one population of said CARs-expressing (immune) cells, or more than one population of said CARs-expressing (immune) cells. The different populations of said CARs expressing (immune) cells may vary based on the identity of the tag-binding domain, the identity of the activation domain, the identity of the (sub)population of immune cells, or a combination thereof.

The formulations comprising therapeutically effective population(s) of said CARs expressing cells may be administered to a subject using modes and techniques known to the skilled artisan. Exemplary modes include, but are not limited to, intravenous injection. Other modes include, without limitation, intratumoral, intradermal, subcutaneous (s.c, s.q., sub-Q, Hypo), intramuscular (i.m.), intraperitoneal (i.p.), intra-arterial, intramedulary, intracardiac, intra-articular (joint), intrasynovial (joint fluid area), intracranial, intraspinal, and intrathecal (spinal fluids).

The formulations comprising therapeutically effective population(s) of said CARs expressing cells that are administered to a subject comprise a number of said CARs-expressing cells such immune cells that is effective for the treatment of the specific indication or disorder.

In general, formulations may be administered that comprise between about $1 \times 10^4$ and about $1 \times 10^{10}$ CARs-expressing cells such as immune cells. In most cases, the formulation may comprise between about $1 \times 10^5$ and about $1 \times 10^9$ CARs-expressing cells such as immune cells, from about $5 \times 10^5$ to about $5 \times 10^8$ CARs-expressing cells such as immune cells, or from about $1 \times 10^6$ to about $1 \times 10^7$ CARs-expressing cells such as immune cells. However, the number of CARs-expressing cells such as immune cells administered to a subject may vary between wide limits, depending upon the location, source, identity, extent and severity of the disorder, the age and condition of the individual to be treated, etc. A physician may ultimately determine appropriate dosages to be used.

The tagged polypeptides as disclosed herein may be formulated for administered to a subject using techniques known to the skilled artisan. Formulations of the tagged polypeptides may include pharmaceutically acceptable excipient(s) (carriers or diluents). Excipients included in the formulations will have different purposes depending, for example, on the nature of the tag, the antigen binding domain of the tagged polypeptide, and the mode of administration. Examples of generally used excipients include, without limitation: saline, buffered saline, dextrose, water-for-injection, glycerol, ethanol, and combinations thereof, stabilizing agents, solubilizing agents and surfactants, buffers and preservatives, tonicity agents, bulking agents, and lubricating agents.

A formulation of tagged polypeptide may include one type of tag polypeptide, or more than one type of tagged polypeptides. The different types of tagged polypeptides may vary based on the identity of the tag, the antigen binding moiety of the tagged polypeptide, or a combination thereof.

The tagged polypeptides may be administered to a subject using modes and techniques known to the skilled artisan. Exemplary modes include, but are not limited to, intravenous, intraperitoneal, and intratumoral injection. Other modes include, without limitation, intradermal, subcutaneous (s.c, s.q., sub-Q, Hypo), intramuscular (i.m.), intra-arterial, intramedulary, intracardiac, intra-articular (joint), intrasynovial (joint fluid area), intracranial, intraspinal, and intrathecal (spinal fluids).

Formulations comprising the polypeptide are administered to a subject in an amount which is effective for treating the specific indication or disorder. In general, formulations comprising at least about 1 µg/kg to about 100 mg/kg body weight of the tagged polypeptide may be administered to a subject in need of treatment. In most cases, the dosage may be from about 100 µg/kg to about 10 mg/kg body weight of the tagged polypeptide daily, taking into account the routes of administration, symptoms, etc. The amount of tagged polypeptide in formulations administered to a subject may vary between wide limits, depending upon the location, source, identity, extent and severity of the disorder, the age and condition of the individual to be treated, etc. A physician may ultimately determine appropriate dosages to be used.

The timing between the administration of the CARs expressing cell formulation and the tag polypeptide-formulation may range widely depending on factors that include the type of (immune) cells being used, the binding specificity of the CAR, the identity of the tag, the antigen binding moiety of the tagged polypeptide, the identity of the target cell, e.g. cancer cell to be treated, the location of the target cell in the subject, the means used to administer the formulations to the subject, and the health, age and weight of the subject being treated. Indeed, the tagged polypeptide formulation may be administered prior to, simultaneous with, or after the genetically engineered (immune) cell formulation.

Depending on the disorder being treated the step of administering the CARs expressing cell formulation, or the step of administering the tagged polypeptide formulation, or both, can be repeated one or more times. When two or more formulations of tagged polypeptides may be applied to a subject, the formulations applied may comprise the same or different tagged polypeptides. When two or more formulations of engineered cells such as immune cells expressing the CARs of the invention are applied to a subject, the engineered cells may be of the same cell type or of different cell types, e.g. T cells and/or NK cells. A formulation of cells such as immune cells may also comprise more than one cell type, each expressing the CARs of the invention.

All definitions, characteristics and embodiments defined herein with regard to the first aspect of the invention as disclosed herein also apply mutatis mutandis in the context of the other aspects of the invention as disclosed herein.

In addition to above described applications and embodiments of the invention further embodiments of the invention are described in the following without intention to be limited to these embodiments.

Embodiments

In one embodiment of the invention, a T cell expresses a CD90-CAR having a CD3zeta signaling domain (the first CAR as disclosed herein) and a CD326-CAR having a 4-1BB costimulatory domain (the second CAR as disclosed herein). The T cell has been provided by a human patient suffering from ovarian cancer that co-expresses CD90 and CD326, and genetically modified to express said CARs.

After in-vitro proliferation of said genetically modified T cells to therapeutically effective amounts the T cells expressing both the CD90CAR and the CD326CAR may be applied to said patient, where these genetically modified T cells will be activated by the cancerous cells that co-express CD90 and CD326 and subsequently eliminate said cancerous cells.

In one embodiment of the invention a composition comprises a biotinylated antibody or antigen binding fragment thereof that specifically binds to CD90, a biotinylated antibody or antigen binding fragment thereof that specifically binds to CD326, and a T cell that expresses a CAR specific for biotin. The T cell has been provided by a human patient suffering from ovarian cancer that co-expresses CD90 and CD326, and genetically modified to express said CAR specific for biotin.

Said composition may be applied to said patient, wherein the sole concentration of the biotinylated antibody or antigen binding fragment thereof that specifically binds to CD90, and the sole concentration of the biotinylated antibody or antigen binding fragment thereof that specifically binds to CD326 is too low to activate said T cell expressing the anti-biotin-CAR, but wherein the sum of said concentrations is sufficient to activate the genetically modified T cell, thereby eliminating said cancerous cells.

In one embodiment of the invention a composition comprises a biotinylated antibody or antigen binding fragment thereof that specifically binds to CD90, a biotinylated antibody or antigen binding fragment thereof that specifically binds to CD326, and a NK cell that expresses a CAR specific for biotin. The NK cell has been provided by a human patient suffering from ovarian cancer that co-expresses CD90 and CD326, and genetically modified to express said CAR specific for biotin.

Said composition may be applied to said patient, wherein the sole concentration of the biotinylated antibody or antigen binding fragment thereof that specifically binds to CD90, and the sole concentration of the biotinylated antibody or antigen binding fragment thereof that specifically binds to CD326 is too low to activate said NK cell expressing the anti-biotin-CAR, but wherein the sum of said concentrations is sufficient to activate the genetically modified NK cell, thereby eliminating said cancerous cells.

Definitions

Unless defined otherwise, technical and scientific terms used herein have the same meaning as commonly understood by one of ordinary skill in the art to which this invention belongs. As used herein the term "comprising" or "comprises" is used in reference to compositions, methods, and respective component(s) thereof, that are essential to the method or composition, yet open to the inclusion of unspecified elements, whether essential or not.

Antibody-drug conjugate (ADC): A molecule that includes an antibody (or antigen-binding fragment of an antibody) conjugated to a drug, such as a cytotoxic agent. ADCs can be used to specifically target a drug to cancer cells through specific binding of the antibody to a tumor antigen expressed on the cell surface. Exemplary drugs for use with ADCs include anti-microtubule agents (such as maytansinoids, auristatin E and auristatin F) and interstrand cross-linking agents (e.g., pyrrolobenzodiazepines; PDBs). Anti-microtubule agent: A type of drug that blocks cell growth by stopping mitosis. Anti-microtubule agents, also referred to as "anti-mitotic agents," are used to treat cancer. A bispecific monoclonal antibody (BsMAb, BsAb) is an artificial protein that can simultaneously bind to two different types of antigen. BsMabs can be manufactured in several structural formats, and current applications have been explored for cancer immunotherapy and drug delivery. There are many formats of bsMab, but the two main categories are IgG-like and non-IgG-like. The main types of manufacturing methods are quadromas, chemical conjugation, and genetic recombination, and each method results in a unique format.

In general, a CAR may comprise an extracellular domain (extracellular part) comprising the antigen binding domain, a transmembrane domain and a cytoplasmic signaling domain (intracellular signaling domain). The extracellular domain may be linked to the transmembrane domain by a linker or spacer. The extracellular domain may also comprise a signal peptide. In some embodiments of the invention the antigen binding domain of a CAR binds a tag or hapten that is coupled to a polypeptide ("haptenylated" or "tagged" polypeptide), wherein the polypeptide may bind to a disease-associated antigen such as a tumor associated antigen (TAA) that may be expressed on the surface of a cancer cell, herein CD90 or CD326.

Such a CAR may be referred to as "anti-tag" CAR or "adapterCAR" or "universal CAR" as disclosed e.g. in U.S. Pat. No. 9,233,125B2.

The haptens or tags may be coupled directly or indirectly to a polypeptide (the tagged polypeptide), wherein the polypeptide may bind to said disease associated antigen expressed on the (cell) surface of a target, e.g. a cancerous cell that co-expresses CD90 and CD326. The tag may be e.g. dextran or a hapten such as biotin or fluorescein isothiocyanate (FITC) or phycoerythrin (PE) or thiamin, but the tag may also be a peptide sequence e.g. chemically or recombinantly coupled to the polypeptide part of the tagged polypeptide. The tag may also be streptavidin. The tag portion of the tagged polypeptide is only constrained by being a molecule that can be recognized and specifically bound by the antigen binding domain specific for the tag of the CAR. For example, when the tag is FITC (Fluorescein isothiocyanate), the tag-binding domain may constitute an anti-FITC scFv. Alternatively, when the tag is biotin or PE (phycoerythrin), the tag-binding domain may constitute an anti-biotin scFv or an anti-PE scFv, respectively.

A "signal peptide" refers to a peptide sequence that directs the transport and localization of the protein within a cell, e.g. to a certain cell organelle (such as the endoplasmic reticulum) and/or the cell surface.

Generally, an "antigen binding domain" refers to the region of the CAR that specifically binds to an antigen, e.g. to a tumor associated antigen (TAA) or tumor specific antigen (TSA). The CARs of the invention may comprise one or more antigen binding domains (e.g. a tandem CAR).

Generally, the targeting regions on the CAR are extracellular. The antigen binding domain may comprise an antibody or an antigen binding fragment thereof. The antigen binding domain may comprise, for example, full length heavy chain, Fab fragments, single chain Fv (scFv) fragments, divalent single chain antibodies or diabodies. Any molecule that binds specifically to a given antigen such as affibodies or ligand binding domains from naturally occurring receptors may be used as an antigen binding domain. Often the antigen binding domain is a scFv. Normally, in a scFv the variable regions of an immunoglobulin heavy chain and light chain are fused by a flexible linker to form a scFv. Such a linker may be for example the "$(G_4/S)_3$-linker".

In some instances, it is beneficial for the antigen binding domain to be derived from the same species in which the CAR will be used in. For example, when it is planned to use it therapeutically in humans, it may be beneficial for the antigen binding domain of the CAR to comprise a human or humanized antibody or antigen binding fragment thereof. Human or humanized antibodies or antigen binding fragments thereof can be made by a variety of methods well known in the art.

"Spacer" or "hinge" as used herein refers to the hydrophilic region which is between the antigen binding domain and the transmembrane domain. The CARs of the invention may comprise an extracellular spacer domain but is it also possible to leave out such a spacer. The spacer may include e.g. Fc fragments of antibodies or fragments thereof, hinge regions of antibodies or fragments thereof, CH2 or CH3 regions of antibodies, accessory proteins, artificial spacer sequences or combinations thereof. A prominent example of a spacer is the CD8alpha hinge.

The transmembrane domain of the CAR may be derived from any desired natural or synthetic source for such domain. When the source is natural the domain may be derived from any membrane-bound or transmembrane protein. The transmembrane domain may be derived for example from CD8alpha or CD28. When the key signaling and antigen recognition modules (domains) are on two (or even more) polypeptides then the CAR may have two (or more) transmembrane domains. The splitting key signaling and antigen recognition modules enable for a small molecule-dependent, titratable and reversible control over CAR cell expression (e.g. WO2014127261A1) due to small molecule-dependent heterodimerizing domains in each polypeptide of the CAR.

The cytoplasmic signaling domain (the intracellular signaling domain or the activating endodomain) of the CAR is responsible for activation of at least one of the normal effector functions of the immune cell in which the CAR is expressed. "Effector function" means a specialized function of a cell, e.g. in a T cell an effector function may be cytolytic activity or helper activity including the secretion of cytokines. The intracellular signaling domain refers to the part of a protein which transduces the effector function signal and directs the cell expressing the CAR to perform a specialized function. The intracellular signaling domain may include any complete, mutated or truncated part of the intracellular signaling domain of a given protein sufficient to transduce a signal which initiates or blocks immune cell effector functions.

Prominent examples of intracellular signaling domains for use in the CARs include the cytoplasmic signaling sequences of the T cell receptor (TCR) and co-receptors that initiate signal transduction following antigen receptor engagement.

Generally, T cell activation can be mediated by two distinct classes of cytoplasmic signaling sequences, firstly those that initiate antigen-dependent primary activation through the TCR (primary cytoplasmic signaling sequences, primary cytoplasmic signaling domain) and secondly those that act in an antigen-independent manner to provide a secondary or co-stimulatory signal (secondary cytoplasmic signaling sequences, co-stimulatory signaling domain). Therefore, an intracellular signaling domain of a CAR may comprise one or more primary cytoplasmic signaling domains and/or one or more secondary cytoplasmic signaling domains.

Primary cytoplasmic signaling domains (primary (intracellular) signaling domains) that act in a stimulatory manner may contain ITAMs (immunoreceptor tyrosine-based activation motifs).

Examples of ITAM containing primary cytoplasmic signaling domains often used in CARs are that those derived from TCRζ (CD3 ζ), FcRgamma, FcRbeta, CD3gamma, CD3delta, CD3epsilon, CD5, CD22, CD79a, CD79b, and CD66d. Most prominent is sequence derived from CD3ζ.

The cytoplasmic domain of the CAR may be designed to comprise the CD3 signaling domain by itself or combined with any other desired cytoplasmic domain(s). The cytoplasmic domain of the CAR can comprise a CD3ζ chain portion and a co-stimulatory signaling region (domain). The co-stimulatory signaling region refers to a part of the CAR comprising the intracellular domain of a co-stimulatory molecule. A co-stimulatory molecule is a cell surface molecule other than an antigen receptor or their ligands that is required for an efficient response of lymphocytes to an antigen. Examples for a co-stimulatory molecule are CD27, CD28, 4-1BB (CD137), OX40, CD30, CD40, PD-1, ICOS, lymphocyte function-associated antigen-1 (LFA-1), CD2, CD7, LIGHT, NKG2C, B7-H3.

The cytoplasmic signaling sequences within the cytoplasmic signaling part of the CAR may be linked to each other with or without a linker in a random or specified order. A short oligo- or polypeptide linker, which is preferably between 2 and 10 amino acids in length, may form the linkage. A prominent linker is the glycine-serine doublet.

As an example, the cytoplasmic domain may comprise the signaling domain of CD3ζ and the signaling domain of CD28. In another example the cytoplasmic domain may comprise the signaling domain of CD3ζ and the signaling domain of CD137. In a further example, the cytoplasmic domain may comprise the signaling domain of CD3ζ, the signaling domain of CD28, and the signaling domain of CD137.

As aforementioned either the extracellular part or the transmembrane domain or the cytoplasmic domain of a CAR may also comprise a heterodimerizing domain for the aim of splitting key signaling and antigen recognition modules of the CAR.

The CAR may be further modified to include on the level of the nucleic acid encoding the CAR one or more operative elements to eliminate CAR expressing immune cells by virtue of a suicide switch. The suicide switch can include, for example, an apoptosis inducing signaling cascade or a drug that induces cell death. In one embodiment, the nucleic acid expressing and encoding the CAR can be further modified to express an enzyme such thymidine kinase (TK) or cytosine deaminase (CD). The CAR may also be part of a gene expression system that allows controlled expression of the CAR in the immune cell. Such a gene expression system may be an inducible gene expression system and wherein when an induction agent is administered to a cell being transduced with said inducible gene expression system, the gene expression system is induced and said CAR is expressed on the surface of said transduced cell.

In some embodiment of the invention the CAR may be a "SUPRA" (split, universal, and programmable) CAR, where a "zipCAR" domain may link an intra-cellular costimulatory domain and an extracellular leucine zipper (WO2017/091546). This zipper may be targeted with a complementary zipper fused e.g. to an scFv region to render the SUPRA CAR T cell tumor specific. This approach would be particularly useful for generating universal CAR T cells for various tumors; adapter molecules could be designed for tumor specificity and would provide options for altering specificity post-adoptive transfer, key for situations of selection pressure and antigen escape.

The chimeric costimulatory receptor (CCR) is a second antigen binding receptor as disclosed herein and may be considered as a special kind of CAR (regularly herein the second CAR in an immune cell is a CCR).

The term "maximally cytotoxic" as used herein means that the immune cell expressing the first CAR and the second CAR as disclosed herein can be fully activated only when in addition to the first CAR the second CAR is activated simultaneously. Said immune cell cannot be sufficiently activated by activation of only one of said both CARs. The term maximally cytotoxic as used herein does not mean that always the maximally possible value or level of cytotoxicity must be reached, it would be sufficient to reach e.g. 50%, 60%, 70%, 80% or 90% of the maximal value but this value is always greater than the value that would be reached by activation of only one of both said CARs in said immune cell.

Alternatively, the CCR may enhance the magnitude of the effector response of the immune cell expressing both the first CAR and the CCR (the second CAR) and may promote extended survival. The magnitude of enhancement of the effector response of the immune cell expressing both the first CAR and the CCR (the second CAR) may be at least 1.5 fold, at least 2 fold, at least 5 fold, at least 10 fold, at least 20 fold, at least 30 fold, at least 40 fold or at least 50 fold compared to the effector response of the immune cell that is activated and stimulated solely by the first CAR, and that is not boosted by the CCR. The increase of magnitude of effector response of the immune cell may be measured or determined e.g. by secretion of effector cytokines such as IL-2, IFN-γ, TNF-α.

For example, the amount of secretion of effector cytokines such as IL-2, IFN-γ, TNF-α by the immune cell expressing both said first CAR and the CCR may be at least 1.5 fold, at least 2 fold, at least 5 fold, at least 10 fold, at least 20 fold, at least 30 fold, at least 40 fold or at least 50 fold higher compared to the amount of secretion of effector cytokines such as IL-2, IFN-γ, TNF-α of the immune cell that is activated and stimulated solely by said first CAR, and that is not boosted by the CCR.

For example, the number of killed target cells by the immune cell expressing both said first CAR and the CCR may be at least 1.5 fold, at least 2 fold, at least 5 fold, at least 10 fold, at least 20 fold, at least 30 fold, at least 40 fold or at least 50 fold higher compared to the number of killed target cells by the immune cell that is activated and stimulated solely by the first CAR, and that is not boosted by the CCR.

The CCR may not be able to mediate said immune response of the immune cell on its own, i.e. it may be necessary for triggering said immune response that the immune cell may express the first CAR, the CCR merely may boost (assist) said immune response of said immune cell.

In contrast to said first CAR, the CCR may not contain ITAM containing domains like CD3ζ or FcεRIγ and therefore no commonly known TCR-mediated signaling events including cis- and/or trans-activation may be induced upon CCR triggering.

The CCR may comprise an antigen binding domain, a transmembrane domain and cytoplasmic part comprising at least one co-stimulatory signaling domain as described herein. Said at least one co-stimulatory signaling domain of said CCR may be selected from the group consisting of ICOS, CD154, CD5, CD2, CD46, HVEM, CD8, CD97, TNFRSF18, CD30, SLAM, DAP10, CD64, CD16, CD89, MyD88, KIR-2DS, KIR-3DS, NKp30, NKp44, NKp46, NKG2D, ICAM, CD27, OX40, 4-1BB and CD28.

The first CARs of the present invention may be designed to comprise any portion or part of the above-mentioned domains as described herein in any order and/or combination resulting in a functional CAR, i.e. a CAR that mediated an immune effector response of the immune effector cell that expresses the CAR.

The CCRs of the present invention may be designed to comprise any portion or part of the above-mentioned domains as described herein in any order and/or combination resulting in a functional CCR, i.e. a CRR that boosts the immune effector response of the immune effector cell that expresses the CAR and the CCR.

The term "tagged polypeptide" as used herein refers to a polypeptide that has bound thereto directly or indirectly at least one additional component, i.e. the tag. The tagged polypeptide as used herein is able to bind an antigen expressed on a target cell. The polypeptide may be an antibody or antigen binding fragment thereof that binds to an antigen expressed on the surface of a target cell such as a tumor associated antigen (TAA) on a cancer cell. The polypeptide of the tagged polypeptide alternatively may be a cytokine or a growth factor or another soluble polypeptide that is capable of binding to an antigen of a target cell.

The terms "adapter" or "adapter molecule" or "tagged polypeptide" as used herein may be used interchangeably.

The tag may be e.g. a hapten or dextran and the hapten or dextran may be bound by the antigen binding domain a CAR comprising an antigen binding domain specific for the tag.

Haptens such as e.g. FITC, biotin, PE, thiamin, streptavidin or dextran are small molecules that elicit an immune response only when attached to a large carrier such as a protein; the carrier may be one that also does not elicit an immune response by itself. Once the body has generated antibodies to a hapten-carrier adduct, the small-molecule hapten may also be able to bind to the antibody, but it will usually not initiate an immune response; usually only the hapten-carrier adduct can do this.

But the tag may also be a peptide sequence e.g. chemically or recombinantly coupled to the polypeptide part of the tagged polypeptide. The peptide may be selected from the group consisting of c-Myc-tag, Strep-Tag, Flag-Tag, and Polyhistidine-tag. The tag may also be streptavidin. The tag portion of the tagged polypeptide is only constrained by being a molecular that can be recognized and specifically bound by the antigen binding domain specific for the tag of the CAR. For example, when the tag is FITC (Fluorescein isothiocyanate), the tag-binding domain may constitute an anti-FITC scFv. Alternatively, when the tag is biotin or PE (phycoerythrin), the tag-binding domain may constitute an anti-biotin scFv or an anti-PE scFv.

The terms "immune cell" or "immune effector cell" may be used interchangeably and refer to a cell that may be part of the immune system and executes a particular effector function such as alpha-beta T cells, NK cells, NKT cells, B cells, innate lymphoid cells (ILC), cytokine induced killer (CIK) cells, lymphokine activated killer (LAK) cells, gamma-delta T cells, mesenchymal stem cells or mesenchymal stromal cells (MSC), monocytes or macrophages. Preferred immune cells are cells with cytotoxic effector function such as alpha-beta T cells, NK cells, NKT cells, ILC, CIK cells, LAK cells or gamma-delta T cells. Most preferred immune effector cells are T cells and/or NK cells. "Effector function" means a specialized function of a cell, e.g. in a T cell an effector function may be cytolytic activity or helper activity including the secretion of cytokines. Alternatively, said immune cell or effector immune cell may be an immune like cell of human origin that can execute a particular effector function associated with the human immune system.

The term "activates and stimulates an immune response of said immune effector cell" in the context of activation of the antigen binding receptor, e.g. the CAR means a primary induction of a signaling cascade which is associated with altered gene expression status in the immune effector cell initiating an immune response which includes, but is not limited to, proliferation, differentiation, cytokine release, cytolytic effector function and the like. For instance, MHC-dependent TCR-binding leads to TCR-clustering and the formation of an immunological synapse, which includes amongst others CD3, CD4, CD8. Subsequently, leading to binding of ZAP70 to CD3ζ that enables activation. Thereupon, several pathways are leading to the expression of ultimately T cell activating transcription factors like AP-1, NFAT and NF-κB that are required e.g. for an increased IL-2 production which enables proliferation and T cell mediated immune responses. However, to induce a persisting immune response, costimulatory receptors like CD28, CD27, CD137 (4-1BB) or ICOS have to become concomitantly activated. Any TCR-binding (Signal 1) without costimulatory signals (Signal 2) is associated with the inhibition of T cell effector function, this means T cells become anergic. The term "mediates an immune response of said immune effector cell" has the same meaning as "activates and stimulates an immune response of said immune effector cell" and may be used interchangeably.

The terms "below the activation threshold of said CAR expressed in said immune cell" and "above the activation threshold of said CAR expressed in said immune cell" as used herein refer to the ability for activating and stimulating an immune response of said immune effector cell as disclosed herein by binding of the tagged polypeptide(s) to the respective CAR of the immune cell. If the concentration of a tagged polypeptide or the sum of tagged polypeptides is too low for activation of the CAR, then said concentration is below the activation threshold of said CAR expressed in said immune cell. If the concentration of a tagged polypeptide or the sum of concentrations (the combined concentrations) of the tagged first polypeptide and the tagged second polypeptide as disclosed herein is sufficient to activate the CAR, then the concentration or the combined concentrations are above the activation threshold of said CAR expressed in said immune cell.

The term "boosts said immune response of said immune effector cell and/or ensures survival of said immune effector cell" in the context of activation of the CCR means an activation of a Signal-1-independent costimulatory signaling cascade in the immune effector cell providing intracellular conditions that promote survival and enable an enhanced Signal-1-dependent immune response. For instance, an immune effector cell co-expressing both a first CAR and a CCR can only be activated by the CAR comprising e.g. the activation domain CD3ζ, however, the cytolytic potential can be boosted by an additional triggering of costimulatory pathways (e.g. 4-1BB or CD28) via the CCR.

The term "antibody" as used herein is used in the broadest sense to cover the various forms of antibody structures including but not being limited to monoclonal and polyclonal antibodies (including full length antibodies), multi-specific antibodies (e.g. bispecific antibodies), antibody fragments, i.e. antigen binding fragments of an antibody, immunoadhesins and antibody-immunoadhesin chimeras, that specifically recognize (i.e. bind) a target antigen. "Antibody fragments" comprise a portion of a full length antibody, preferably the variable domain thereof, or at least the antigen binding site thereof ("an antigen binding fragment of an antibody"). Examples of antibody fragments include Fab (fragment antigen binding), scFv (single chain fragment variable), single domain antibodies, diabodies, dsFv, Fab', diabodies, single-chain antibody molecules, and multispecific antibodies formed from antibody fragments.

As used herein, the term "antigen" is intended to include substances that bind to or evoke the production of one or more antibodies and may comprise, but is not limited to, proteins, peptides, polypeptides, oligopeptides, lipids, carbohydrates such as dextran, haptens and combinations thereof, for example a glycosylated protein or a glycolipid. The term "antigen" as used herein refers to a molecular entity that may be expressed on the surface of a target cell and that can be recognized by means of the adaptive immune system including but not restricted to antibodies or TCRs, or engineered molecules including but not restricted to endogenous or transgenic TCRs, CARs, scFvs or multimers thereof, Fab-fragments or multimers thereof, antibodies or multimers thereof, single chain antibodies or multimers thereof, or any other molecule that can execute binding to a structure with high affinity.

The cluster of differentiation (abbreviated as CD) is a protocol used for the identification and investigation of cell surface molecules, regularly polypeptides, providing targets for immunophenotyping of cells.

CD90 (or Thy-1) is a 25-37 kDa heavily N-glycosylated, glycophosphatidylinositol (GPI) anchored conserved cell surface protein with a single V-like immunoglobulin domain, originally discovered as a thymocyte antigen.

CD326 (or Epithelial cell adhesion molecule (EpCAM)) is a transmembrane glycoprotein mediating Ca2+-independent homotypic cell-cell adhesion in epithelia. CD326 is also involved in cell signaling, migration, proliferation, and differentiation. Additionally, CD326 has oncogenic potential via its capacity to upregulate c-myc, e-fabp, and cyclins A & E.

The term "target cell" as used herein refers to a cell which expresses an antigen on its cell surface that should be recognized (bound) by the antigen binding receptor as disclosed herein and/or by the CCR as disclosed herein and/or by the tagged polypeptide as disclosed herein. Regularly, herein the target cell is a (cancerous) cell that co-expresses CD90 and CD326.

The term "combination" in the context of antigen binding domains specific for CD90 and CD326 may also e.g. be a "kit" comprising the antigen binding domains specific for CD90 and CD326 or a "combination of compositions" comprising the antigen binding domains specific for CD90 and CD326 or a "system" comprising the antigen binding domains specific for CD90 and CD326.

As used herein, the term "subject" refers to a mammal such as mouse, rat, cow, pig, goat, chicken dog, monkey or human. Preferentially, the subject is a human. The subject may be a subject suffering from a disorder such as cancer (a patient), but the subject may be also a healthy subject.

The term "autologous" as used herein refers to any material derived from the same subject to who it is later re-introduced.

The term "allogeneic" as used herein refers to any material derived from a different subject of the same species as the subject to who the material is re-introduced.

The terms "therapeutically effective amount" or "therapeutically effective population" mean an amount of a cell population which provides a therapeutic benefit in a subject.

The terms "specifically binds" or "specific for" with respect to an antigen binding domain of an antibody, of an antigen binding fragment thereof, as used e.g. in the CAR and CCR as disclosed herein, or in the tagged polypeptide, refer to an antigen binding domain which recognizes and binds to a specific antigen, but does not substantially recognize or bind other molecules in a sample. An antigen binding domain that binds specifically to an antigen from one species may bind also to that antigen from another species. This cross-species reactivity is typical to many antibodies and therefore not contrary to the definition of that antigen binding domain as specific. An antigen binding domain that specifically binds to an antigen may bind also to different allelic forms of the antigen (allelic variants, splice variants, isoforms etc.) or homologous variants of this antigen from the same gene family. This cross reactivity is typical to many antibodies and therefore not contrary to the definition of that antigen binding domain as specific.

The terms "engineered cell" and "genetically modified cell" as used herein can be used interchangeably. The terms mean containing and/or expressing a foreign gene or nucleic acid sequence which in turn modifies the genotype and/or phenotype of the cell or its progeny. Especially, the terms refer to the fact that cells, preferentially immune cells can be manipulated by recombinant methods well known in the art to express stably or transiently peptides or proteins which are not expressed in these cells in the natural state. For example, immune cells are engineered to express an artificial construct such as a chimeric antigen receptor on their cell surface.

The term "treat" (treatment of) a disorder (e.g. cancer) as used herein means to reduce the frequency or severity of at least one sign or symptom of a disease or disorder experienced by a subject.

The term "expression" as used herein is defined as the transcription and/or translation of a particular nucleotide sequence driven by its promoter in a cell.

The amino acid sequences of SEQ ID NO: 1 to SEQ ID NO: 4 as given in the sequence listing protocol are partial sequences of CARs as disclosed herein. Said sequences of SEQ ID NO: 1 to SEQ ID NO: 4 may also comprise variants of these sequences, respectively, which have some amino acids deleted, added or replaced while still retaining the intended function as described herein. Therefore, included in this definition are variants of the amino acid sequences in SEQ ID NO: 1 to SEQ ID NO: 4, respectively, such as amino acid sequences essentially similar to SEQ ID NO: 1 to SEQ ID NO: 4, respectively, having a sequence identity of at least 70%, or at least 75%, 80%, 85%, 90%, 95%, 97%, 98% or 99% at the amino acid sequence level. In general, all amino acid variations which do not lead to intentional changes of the intended function of the sequences SEQ ID NO: 1 to SEQ ID NO: 4, respectively, are included under this definition. In the context of the present invention, "sequence identity" may be determined using pairwise alignments using alignments programs for amino acid sequences well known to the art.

The term "cancer" is known medically as a malignant neoplasm. Cancer is a broad group of diseases involving unregulated cell growth and includes all kinds of leukemia. In cancer, cells (cancerous cells) divide and grow uncontrollably, forming malignant tumors, and invading nearby parts of the body. The cancer may also spread to more distant parts of the body through the lymphatic system or bloodstream. There are over 200 different known cancers that affect humans.

The term "human cancer comprising cancerous cells that co-express CD90 and CD326" as used herein refers to a cancer, wherein at least a subpopulation of said cancer express both CD90 and CD326 on the same cell.

The term "human ovarian cancer comprising cancerous cells co-expressing CD90 and CD326" refers to human ovarian cancer, wherein at least a subpopulation of said human ovarian cancer express both CD90 and CD326 on the same cell.

Ovarian cancer is a cancer that forms in or on an ovary. It results in abnormal cells that have the ability to invade or spread to other parts of the body. When this process begins, there may be no or only vague symptoms. Symptoms become more noticeable as the cancer progresses. These symptoms may include bloating, pelvic pain, abdominal swelling, and loss of appetite, among others. Common areas to which the cancer may spread include the lining of the abdomen, lymph nodes, lungs, and liver.

This invention is further illustrated by the following examples, which are not to be construed in any way as imposing limitations upon the scope thereof.

EXAMPLES

The following examples are intended for a more detailed explanation of the invention but without restricting the invention to these examples.

Figure 1:
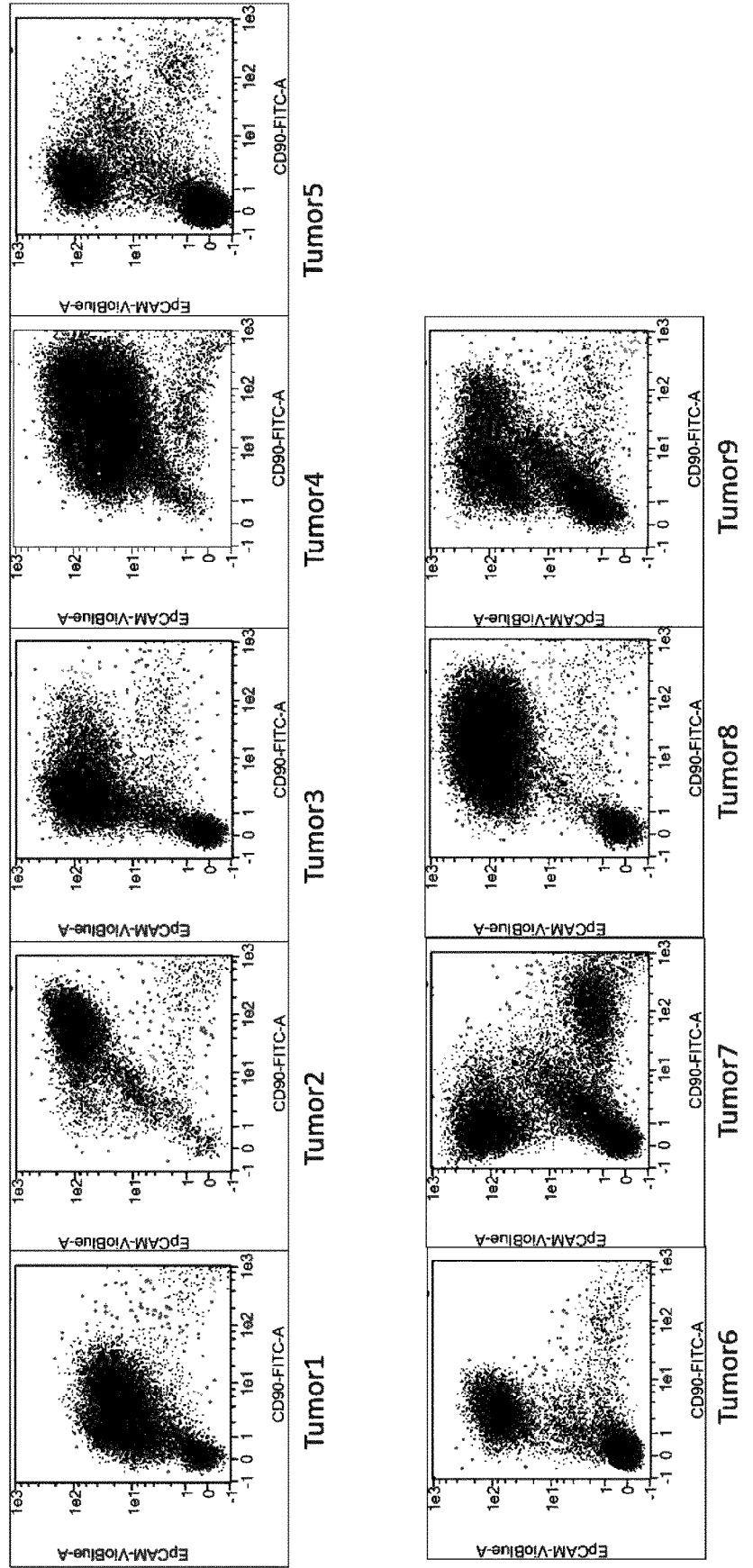
FIG. 1 Flow cytometric screening assay revealed co-expression of CD90 and CD326 on a subset of high-grade serous ovarian carcinoma Several human high-grade serous ovarian carcinoma were dissociated and subsequently analyzed by flow cytometry. The flowcytometric assay employed an unbiased flowcytometric screening assay targeting cellular surface molecules. Some samples reveal a distinct population co-expressing CD90 and CD326 (highlighted with bold and underlined).
Figure 2:
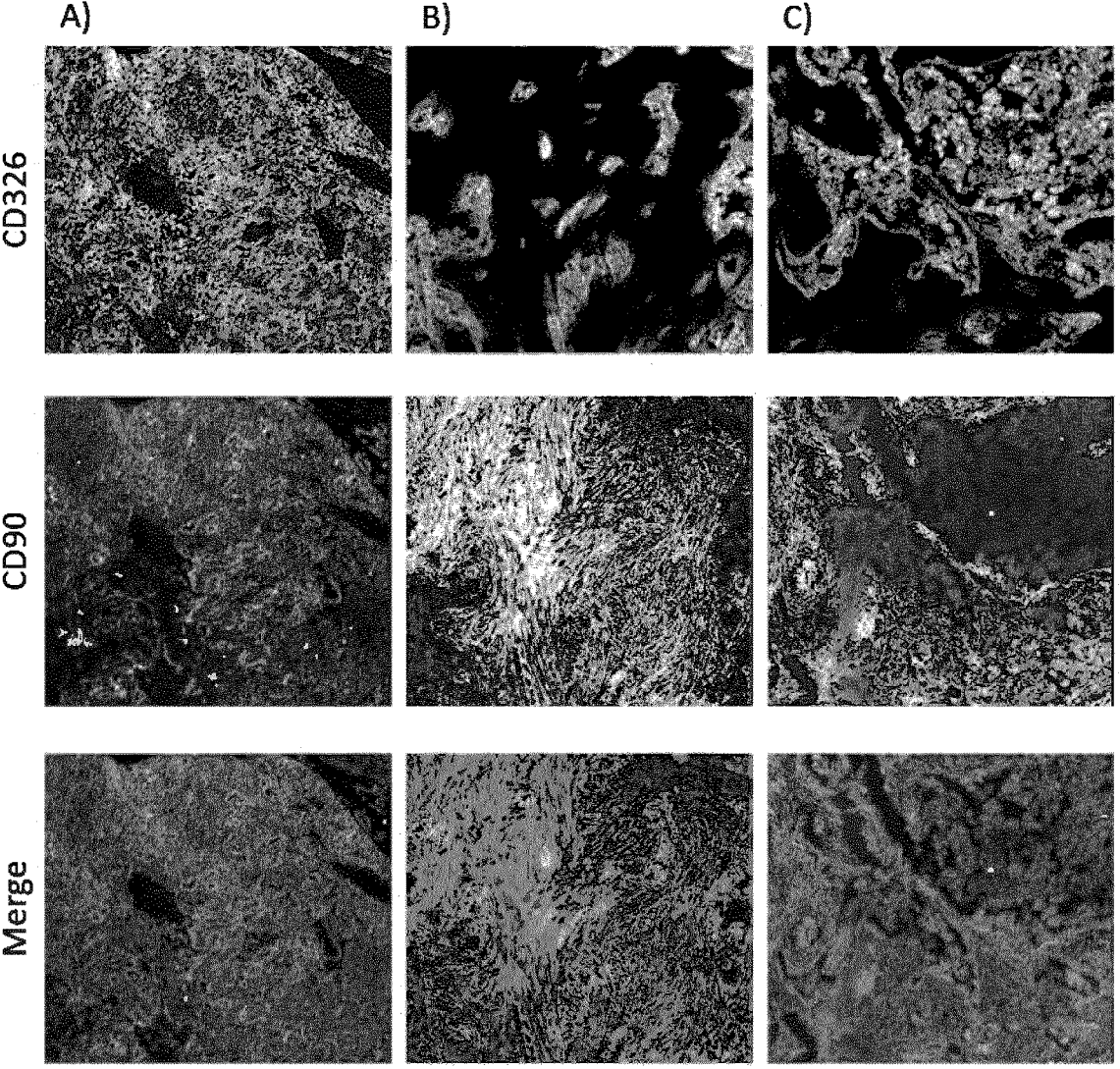
FIG. 2 Microscopic immunofluorescence analysis revealed co-expression of CD90 and CD326 on a subset of high-grade serous ovarian carcinoma Fresh-frozen human high-grade serous ovarian carcinoma were sliced and fixed with acetone. The subsequent screening was performed on the MACSima™ ultra-high-content imaging platform by employing a sequential staining of antibodies. Here the two markers of interest CD90 as well as CD326 are shown and analyzed for cellular co-expression. A) Region of interest CD90 and CD326 co-expressing

Example 1: Identification of a Combination of Conjugates Comprising a Fluorescent Moiety and an Antigen Recognizing Moiety which in Combination Allow to Discriminate Between Ovarian Carcinoma (OvCa) Cells and Non-OvCa Cells High-grade serous ovarian carcinoma resections were dissociated and single cell suspensions were analyzed by flow cytometry (FIG. 1). Employing an unbiased surface marker screening library revealed the co-expression of CD90 and CD326 on a subset of high-grade ovarian carcinoma patients (FIG. 2). Subsequently, this distinct target combination was validated by cyclic immunofluorescence microscopy. Fresh-frozen high-grade serous ovarian carcinoma resections were sliced and fixed with acetone. A screening was performed using a novel high content imaging platform enabling fully automated cyclic fluorescence imaging of individual biological samples. Sequential staining of OvCa specimen with several antigen recognizing moiety conjugated to a fluorescent moiety revealed the expression of a number of antigens. The co-expression of EpCAM (CD326), which is a well-known marker for human epithelial tissues and carcinomas, in combination with CD90 was validated in a subset of patients (FIG. 3). Data analysis and further co-stainings confirmed that CD326 and CD90 are co-expressed on a subset of OvCa samples.

Since on-target off-tumor toxicities of CAR T cell therapy, i.e. CAR T cells bind to and lyse non-tumor cells which express the CAR target under physiological conditions, have been described for several CAR T cell products, the target expression has to be analyzed in healthy tissues. However, the expression on healthy tissue was found to be at least partially discriminative opening the possibility to combine the two markers to get a selective labelling of cells to discriminate OvCa from healthy cells (FIG. 3).

Thus, the combination of CD326 and CD90 opens the possibility for a dual-targeting CAR T cell treatment of OvCa. CD326 and CD90 are co-expressed on a subset of OvCa cells but not or to a lesser extent on healthy tissues. Therefore, using CAR T cells which are activated by the co-detection of CD326 and CD90 but not activated in the absence of one of the two markers should result in an efficient killing of OvCa cells leaving healthy cells unaffected either because CD326 or CD90 are not expressed, i.e. CD90 and CD326 are not co-expressed on the same (healthy) cell.

Example 2: Use of Combinations of Antigen Recognizing Moieties which in Combination Allow to Discriminate Between Ovarian Carcinoma (OvCa) Cells and Non-OvCa Cells In order to prevent on-target off-tumor toxicities of CAR T cell therapy several technological solutions may be employed to increase CAR T cell specificity. One option is the use of dual-targeting CARs, i.e. T cell activation is achieved by overcoming a threshold which is determined by recognizing multiple markers by the CAR T cell. In an AND CAR the CAR T cell co-expresses two independent CAR constructs composed of an antigen binding moiety, a hinge, a trans-membrane domain, and one or more intracellular signaling domains. Wherein one CAR recognizing a distinct epitope delivers the activating signal (signal1), which—on its own—is insufficient to overcome the activation threshold of the CAR T cell. Additionally, the second CAR recognizing another epitope carries a costimulatory domain (signal2) that—only in combination with the first CAR-synergizes with the first CAR to overcome the activation threshold to fully activate the T cell.

An AND CAR T cell is composed of a first CAR recognizing one tumor-associated antigen A. The first CAR uses an activating intracellular domain, e.g. CD3zeta. Upon binding of the CAR T cell to antigen A on a cell the CAR T cell cannot overcome the activation threshold. To overcome the activation threshold, a second CAR is co-expresses by the T cell binding an antigen B which is co-expressed on antigen A-expressing tumor cells. The antigen B recognizing CAR contains one or more co-stimulatory domains, e.g. CD28 or 4-1BB. Only by recognizing antigen A and B on the same cell the CAR T cell overcomes the activation threshold and gets fully activated, i.e. secretes cytokines, proliferates, and lyses the cell expressing antigen A and B.

Alternatively, another technology for dual-targeting of tumor cells can be based on adapter CAR T cells using more than one adapter specificities (i.e. surface activation matrix, SAM). Here, each single adapter molecule on its own would not lead to an adapter CAR T cell activation, only the combinatorial use of more than one antibody can lead to an adapter CAR T cell activation. In detail, the adapter CAR T cell recognizes a tagged-adapter molecule, e.g. a biotinylated antibody or a FLAG-tagged Fab molecule. Additionally the Adapter CAR compromises an activating signal delivering domain, e.g. CD3zeta, and one or more co-stimulatory domains, e.g. CD28 or 4-1BB. When an Adapter CAR T cell recognizing biotin binds to an biotinylated antibody, which is directed against CD326, and bridges to the CD326 expressing cancer cell, the Adapter CAR T cells is activated and lyses the CD326 expressing tumor cell. Adapter CAR T cell activation and target cell lysis depend on the doses of adapter molecule present. Thus, activity of the Adapter CAR T cells is dose-dependent and activity correlates with the adapter molecule titration (FIG. 4). Adapter CAR T cells have to overcome an activation threshold to reach full activation and cytolytic activity. In the surface activation matrix concept the both principals (dose-dependency and activation threshold) are combined. Two or more adapter molecules targeting different markers on cancer cells are used in doses which are—on their own—suboptimal and cannot overcome the activation threshold of the CAR T cell (FIG. 5). However, the combination of several adapter molecules at suboptimal doses have an additive effect and can overcome the activation threshold leading to complete CAR T cell functionality, i.e. secretes cytokines, proliferates, and lyses the cancer cell expressing the respective markers.

Consequently, a dual-targeting CAR T cell which employs one or more of the aforementioned mechanisms in combination with a targeting simultaneously the CD326 antigen and the CD90 antigen improves specificity of a CAR T cell and reduces on target/off-tumor toxicity. When employing target cells with differential CD90 and CD326 expression (FIG. 6) specificity of this approach can be assessed and validated. The aforementioned synergistic effect of co-targeting a cancer cell co-expressing CD90 and CD326 with two adapter molecules in the presence of adapter CAR T cells (FIG. 5) is lost when the target cells express either one of the targets alone (lack of CD90 expression: FIG. 7; lack of CD326 expression: FIG. 8) or none of the targets (FIG. 9).

Example 3: Identification and Validation of a Combination of Conjugates Comprising a Fluorescent Moiety and an Antigen Recognizing Moiety which in Combination Allow to Discriminate Between Ovarian Carcinoma (OvCa) Cells and Non-OvCa Cells In order to validate the expression of CD90 and CD326 in healthy tissues cyclic immunofluorescence microscopy was performed. Fresh-frozen healthy tissues (breast, brain cerebellum, colon, heart, kidney, liver, lung, medulla, oblongata, ovary, pancreas, pituitary gland, skeletal muscle, skin, smooth muscle, testis, and thyroid gland) as well as high-grade serous ovarian carcinoma were sliced and fixed with acetone.

A screening was performed using a novel high content imaging platform enabling fully automated cyclic fluorescence imaging of individual biological samples. Sequential staining of healthy tissues and OvCa specimen with several antigen recognizing moiety conjugated to a fluorescent moiety revealed the co-expression of EpCAM (CD326), which is a well-known marker for human epithelial tissues and carcinomas, in combination with CD90 was validated in a subset of patients (FIG. 10).

Since on-target off-tumor toxicities of CAR T cell therapy, i.e. CAR T cells bind to and lyse non-tumor cells which express the CAR target under physiological conditions, have been described for several CAR T cell products, the target expression has to be analyzed in healthy tissues. Images were segmented based on cell segmentation and expression of CD90 and CD326 was quantified (FIG. 11). Expression of CD90 and CD326 was analyzed an healthy tissues (FIG. 11A) and elevated expression of CD90 and CD326 was exclusively detected in ovarian cancer samples (FIG. 11B).

Thus, the combination of CD326 and CD90 opens the possibility for a dual-targeting CAR T cell treatment of OvCa. CD326 and CD90 are co-expressed on a subset of OvCa cells but not or to a lesser extent on healthy tissues. Therefore, using CAR T cells which are activated by the co-detection of CD326 and CD90 but not activated in the absence of one of the two markers should result in an efficient killing of OvCa cells leaving healthy cells unaffected either because CD326 or CD90 are not expressed, i.e. CD90 and CD326 are not co-expressed on the same (healthy) cell.

Example 4: Use of Combinations of Antigen Recognizing Moieties which in Combination Allow to Discriminate Between Ovarian Carcinoma (OvCa) Cells and Non-OvCa Cells In order to prevent on-target off-tumor toxicities of CAR T cell therapy several technological solutions may be employed to increase CAR T cell specificity. One option is the use of dual-targeting CARs, i.e. T cell activation is achieved by overcoming a threshold which is determined by recognizing multiple markers by the CAR T cell. In an AND CAR the CAR T cell co-expresses two independent CAR constructs composed of an antigen binding moiety, a hinge, a trans-membrane domain, and one or more intracellular signaling domains. Wherein one CAR recognizing a distinct epitope delivers the activating signal (signal1), which—on its own—is insufficient to overcome the activation threshold of the CAR T cell. Additionally, the second CAR recognizing another epitope carries a costimulatory domain (signal2) that—only in combination with the first CAR—synergizes with the first CAR to overcome the activation threshold to fully activate the T cell.

An AND CAR T cell is composed of a first CAR recognizing one tumor-associated antigen A. The first CAR uses an activating intracellular domain, e.g. CD3zeta. Upon binding of the CAR T cell to antigen A on a cell the CAR T cell cannot overcome the activation threshold. To overcome the activation threshold, a second CAR is co-expresses by the T cell binding an antigen B which is co-expressed on antigen A-expressing tumor cells. The antigen B recognizing CAR contains one or more co-stimulatory domains, e.g. CD28 or 4-1BB. Only by recognizing antigen A and B on the same cell the CAR T cell overcomes the activation threshold and gets fully activated, i.e. secretes cytokines, proliferates, and lyses the cell expressing antigen A and B.

Alternatively, another technology for dual-targeting of tumor cells can be based on adapter CAR T cells using more than one adapter specificities (i.e. surface activation matrix, SAM). Here, each single adapter molecule on its own would not lead to an adapter CAR T cell activation, only the combinatorial use of more than one adapter molecule can lead to an adapter CAR T cell activation. In detail, the adapter CAR T cell recognizes a tagged-adapter molecule, e.g. a biotinylated antibody or a FLAG-tagged Fab molecule. Additionally the Adapter CAR compromises an activating signal delivering domain, e.g. CD3zeta, and one or more co-stimulatory domains, e.g. CD28 or 4-1BB. When an Adapter CAR T cell recognizing biotin binds to an biotinylated antibody, which is directed against CD326, and bridges to the CD326 expressing cancer cell, the Adapter CAR T cells is activated and lyses the CD326 expressing tumor cell. Adapter CAR T cell activation and target cell lysis depend on the doses of adapter molecule present.

Thus, activity of the Adapter CAR T cells is dose-dependent and activity correlates with the adapter molecule titration, i.e. mono-biotinylated Fab molecules (FIG. 12-20). Adapter CAR T cells have to overcome an activation threshold to reach full activation and cytolytic activity. In the surface activation matrix concept the both principals (dose-dependency and activation threshold) are combined. Two or more adapter molecules targeting different markers on cancer cells are used in doses which are—on their own—suboptimal and cannot overcome the activation threshold of the CAR T cell (FIG. 12-20). However, the combination of several adapter molecules at suboptimal doses have an additive effect and can overcome the activation threshold leading to complete CAR T cell functionality, i.e. secretes cytokines, proliferates, and lyses the cancer cell expressing the respective markers.

Consequently, a dual-targeting CAR T cell which employs one or more of the aforementioned mechanisms in combination with a targeting simultaneously the CD326 antigen and the CD90 antigen improves specificity of a CAR T cell and reduces on target/off-tumor toxicity.

When titrating the concentrations of monobiotinylated anti-CD90 Fab, anti-CD326 Fab and the combination of both Fabs (5 ng/ml (FIG. 12), 1 ng/ml (FIG. 13), 0.75 ng/ml (FIG. 14), 0.5 ng/ml (FIG. 15), 0.25 ng/ml (FIG. 16), 0.1 ng/ml (FIG. 17), 0.05 ng/ml (FIG. 18), 0,025 ng/ml (FIG. 19), 0.01 ng/ml (FIG. 20)) against target cells with differential CD90 and CD326 expression specificity of this approach as well as activation thresholds can be assessed and validated. Synergistic effects on cancer cell killing are detected with concentration within the range from 0.25 ng/ml (FIG. 16) to 0,025 ng/ml (FIG. 19).

The aforementioned synergistic effect of co-targeting a cancer cell co-expressing CD90 and CD326 with two adapter molecules in the presence of adapter CAR T cells is lost when the target cells express either one of the targets alone (FIG. 12-20).

The synergistic effects on cancer cell killing are complemented by cytokine secretion (GM-CSF, IFN-gamma; FIG. 14, FIG. 15) as well as activation (CD25, PD-1) and exhaustion (CD223) markers expressed by CART cells (FIG. 17, FIG. 18).

Moreover, titration of anti-CD326 Fab against a constant concentration of anti-CD90 Fab (FIG. 21) or titration of anti-CD90 Fab against a constant concentration of anti-CD326 Fab (FIG. 22) show an influence of anti-CD90 Fab concentration on overall cancer cell killing efficacy. This effect of anti-CD90 Fabs was confirmed by cytokine secretion (FIG. 25) as well as activation (FIG. 28, FIG. 30 I-P) and exhaustion (FIG. 29, FIG. 30 A-H) markers expressed by CAR T cells.

REFERENCES

Lamers, C., Sleijfer, S., van Steenbergen, S., van Elzakker, P., van Krimpen, B., Groot, C., Vulto A., den Bakker M., Oosterwijk E. Debets R., Gratama, J. (2013). Treatment of metastatic renal cell carcinoma with CAIX CAR-engineered T cells: clinical evaluation and management of on-target toxicity. Mol Ther., 21(4), S. 904-912. doi: 10.1038/mt.2013.17

Lanitis, E., Poussin, M., Klattenhoff, A., Song, D., Sandaltzopoulos, R., June C. H., & Powell Jr., D. (2013). Chimeric antigen receptor T cells with dissociated signaling domains exhibit focused anti-tumor activity with reduced potential for toxicity in vivo. Cancer Immunol Res., 1(1), 43-53.

Matulonis, U., Sood, A., Fallowfield, L., Howitt, B., Sehouli, J., & Karlan, B. (2016). Ovarian Cancer. Nat Rev Disease Primers. doi:10.1038/nrdp.2016.61

Zhao, J., Song, Y., & Liu, D. (2019). Clinical trials of dual-target CAR T cells, donor-derived CART cells, and universal CART cells for acute lymphoid leukemia. J Hematol Oncol, 12(17). https://doi.org/10.1186/s13045-019-0705-x

The invention claimed is:

1. An in vitro combination comprising:
   a) an antigen binding domain specific for CD90 and
   b) an antigen binding domain specific for CD326
   for use in treatment of human cancer comprising cancerous cells that co-express CD90 and CD326.

2. The in vitro combination according to claim 1, wherein said combination further comprises:
   a) a tagged first polypeptide having the antigen binding domain specific for CD90,
   b) a tagged second polypeptide having the antigen binding domain specific for CD326, wherein the tag of the first polypeptide and the tag of the second polypeptide are identical, and
   c) an immune cell comprising a chimeric antigen receptor (CAR), the CAR comprising:
      i) an antigen binding domain specific for said tag of the first and second polypeptides,
      ii) a transmembrane domain, and
      iii) an intracellular signaling domain comprising a primary signaling domain and at least one costimulatory domain.

3. The in vitro combination of claim 2, wherein the concentration of said tagged first polypeptide is below the activation threshold of said CAR expressed in said immune cell, wherein the concentration of said tagged second polypeptide is below the activation threshold of said CAR expressed in said immune cell, wherein the combined concentrations of the tagged first polypeptide and the tagged second polypeptide is above the activation threshold of said CAR expressed in said immune cell.

4. The in vitro combination of claim 3, wherein the concentration of said tagged first polypeptide is at least 10% below the concentration that is needed when the CAR is activated solely by said tagged first polypeptide, i.e. without the presence of said tagged second polypeptide, and wherein the concentration of said tagged second polypeptide is at least 10% below the concentration that is needed when the CAR is activated solely by said tagged second polypeptide, i.e. without the presence of said tagged first polypeptide.

5. The in vitro combination according to claim 1, wherein said combination further comprises an immune cell comprising a first CAR and a second CAR,
   the first CAR comprising:
   i) the first antigen binding domain specific for CD90 or CD326,
   ii) a transmembrane domain, and
   iii) a first intracellular signaling domain,
   wherein said first intracellular signaling domain is a primary signaling domain comprising an immunoreceptor tyrosine-based activation motif (ITAM), wherein said first intracellular signaling domain does not comprise a costimulatory domain,
   and the second CAR comprising:
   i) the second antigen binding domain specific for CD326 if the first antigen binding domain of the first CAR is specific for CD90, or the second antigen binding domain specific for CD90 if the first antigen binding domain of the first CAR is specific for CD326,
   ii) a transmembrane domain, and
   iii) a second intracellular signaling domain,
   wherein said second intracellular signaling domain comprises one or more co-stimulatory signaling domains,
   and wherein said immune cell becomes maximally cytotoxic only when said first signaling domain and said second signaling domain are both activated by said CD90 and CD326, respectively.

6. The in vitro combination according to claim 1, wherein said combination further comprises an immune cell comprising a first CAR and a second CAR,
   the first CAR comprising:
   i) the first antigen binding domain specific for a tag of a tagged polypeptide, wherein said polypeptide has an antigen binding domain specific for CD90 or CD326,
   ii) a transmembrane domain, and
   iii) a first intracellular signaling domain,
   wherein said first intracellular signaling domain is a primary signaling domain comprising an immunoreceptor tyrosine-based activation motif (ITAM), wherein said first intracellular signaling domain does not comprise a costimulatory domain,
   and the second CAR comprising:
   i) the second antigen binding domain specific for CD326 if said tagged polypeptide specifically binds to CD90, or the second antigen binding domain specific for CD90 if said tagged polypeptide specifically binds to CD326,
   ii) a transmembrane domain, and
   iii) a second intracellular signaling domain,
   wherein said second intracellular signaling domain comprises one or more co-stimulatory signaling domains,
   and wherein said immune cell becomes maximally cytotoxic only when said first signaling domain is activated by said tag and said second signaling domain is activated by said CD90 or CD326,
   and wherein said combination further comprises said tagged polypeptide.

7. The in vitro combination according to claim 1, wherein said combination further comprises an immune cell comprising a first CAR and a second CAR,
   the first CAR comprising:
   i) the first antigen binding domain specific for CD90 or CD326,
   ii) a transmembrane domain, and
   iii) a first intracellular signaling domain,
   wherein said first intracellular signaling domain is a primary signaling domain comprising an immunoreceptor tyrosine-based activation motif (ITAM), wherein said first intracellular signaling domain does not comprise a costimulatory domain,
   and the second CAR comprising:
   i) the second antigen binding domain specific for a tag of a tagged polypeptide wherein said polypeptide has an antigen binding domain specific for CD326 if the first antigen binding domain of the first CAR is specific for CD90, or the second antigen binding domain specific for a tagged polypeptide, wherein said polypeptide has an antigen binding domain specific for CD90 if the first antigen binding domain of the first CAR is specific for CD326,
   ii) a transmembrane domain, and
   iii) a second intracellular signaling domain,
   wherein said second intracellular signaling domain comprises one or more co-stimulatory signaling domains,
   and wherein said immune cell becomes maximally cytotoxic only when said first signaling domain is activated by said CD90 or CD326 and said second signaling domain is activated by said tag,
   and wherein said combination comprises said tagged polypeptide.

8. The in vitro combination according to claim 1, wherein said combination further comprises an immune cell comprising a first CAR and a second CAR,

US 12,630,645 B2

45 the first CAR comprising:
i) the first antigen binding domain specific for a first tag of a first tagged polypeptide, wherein said first polypeptide has an antigen binding domain specific for CD90 or CD326,
ii) a transmembrane domain, and
iii) a first intracellular signaling domain,
wherein said first intracellular signaling domain is a primary signaling domain comprising an immunoreceptor tyrosine-based activation motif (ITAM), wherein said first intracellular signaling domain does not comprise a costimulatory domain,
and the second CAR comprising:
i) the second antigen binding domain specific for a second tag of a second tagged polypeptide, wherein said second polypeptide has an antigen binding domain specific for CD326 if said first tagged polypeptide specifically binds to CD90, or the second antigen binding domain specific for a second tagged polypeptide wherein said second polypeptide has an antigen binding domain specific for CD90 if said first tagged polypeptide specifically binds to CD326,
ii) a transmembrane domain, and
iii) a second intracellular signaling domain,
wherein said second intracellular signaling domain comprises one or more co-stimulatory signaling domains,
and wherein said immune cell becomes maximally cytotoxic only when said first signaling domain and said second signaling domain are both activated by said first tag and said second tag, respectively,
and wherein said combination comprises said first tagged polypeptide and said second tagged polypeptide.
9. The in vitro combination according to claim 1, for use in treatment of a human ovarian cancer comprising cancerous cells that co-express CD90 and CD326.
10. A method of treating a subject having a human cancer comprising cancerous cells that co-express CD90 and CD326, wherein the method comprises:
a) administering to said subject a tagged first polypeptide having an antigen binding domain specific for CD90, and
b) administering to said subject a tagged second polypeptide having an antigen binding domain specific for CD326, wherein the tag of the first polypeptide and the tag of the second polypeptide are identical, and
c) administering to said subject an immune cell comprising a chimeric antigen receptor (CAR), the CAR comprising:
i) an antigen binding domain specific for said tag of the first and second polypeptides,

ii) a transmembrane domain, and
iii) an intracellular signaling domain comprising a primary signaling domain and at least one costimulatory domain, thereby treating the subject having said human cancer.
11. The method of claim 10, wherein said human cancer is an ovarian cancer.
12. The method of claim 10, wherein the concentration of said tagged first polypeptide is below the activation threshold of said CAR expressed in said immune cell, wherein the concentration of said tagged second polypeptide is below the activation threshold of said CAR expressed in said immune cell, wherein the combined concentrations of the tagged first polypeptide and the tagged second polypeptide is above the activation threshold of said CAR expressed in said immune cell.
13. The method of claim 12, wherein the concentration of said tagged first polypeptide is at least 10% below the concentration that is needed when the CAR is activated solely by said tagged first polypeptide, i.e. without the presence of said tagged second polypeptide, and wherein the concentration of said tagged second polypeptide is at least 10% below the concentration that is needed when the CAR is activated solely by said tagged second polypeptide, i.e. without the presence of said tagged first polypeptide.
14. The method of claim 10, wherein said antigen binding domain specific for CD90 of the tagged polypeptide comprises SEQ ID NO: 1 and SEQ ID NO: 2, and wherein said an antigen binding domain specific for CD326 comprises SEQ ID NO: 3 and SEQ ID NO: 4.
15. An in vitro combination comprising an antigen binding domain specific for CD90 and an antigen binding domain specific for CD326, wherein the in vitro combination comprises:
a) a tagged first polypeptide having the antigen binding domain specific for CD90;
b) a tagged second polypeptide having the antigen binding domain specific for CD326, wherein the tag of the first polypeptide and the tag of the second polypeptide are identical; and
c) an immune cell comprising a chimeric antigen receptor (CAR), the CAR comprising:
i) an antigen binding domain specific for the tag of the first polypeptide and the tag of the second polypeptide;
ii) a transmembrane domain, and
iii) an intracellular signaling domain comprising a primary signaling domain and at least one costimulatory domain.

* * * * *